United States Patent
Kondo et al.

[11] Patent Number: 5,993,690
[45] Date of Patent: Nov. 30, 1999

[54] ORGANOSILICON COMPOUND, LIQUID CRYSTAL COMPOSITION, AND LIQUID-CRYSTAL DISPLAY ELEMENT

[75] Inventors: Tomoyuki Kondo; Shuichi Matsui; Norihisa Hachiya; Etsuo Nakagawa, all of Chiba, Japan

[73] Assignee: Chisso Corporation, Osaka, Japan

[21] Appl. No.: 09/000,409

[22] PCT Filed: Jul. 26, 1996

[86] PCT No.: PCT/JP96/02103

§ 371 Date: Jan. 26, 1998

§ 102(e) Date: Jan. 26, 1998

[87] PCT Pub. No.: WO97/05144

PCT Pub. Date: Feb. 13, 1997

[30] Foreign Application Priority Data

Jul. 27, 1995 [JP] Japan ..................... 7-211211

[51] Int. Cl.⁶ .......... C09K 19/54; C09K 19/52; C07F 7/04
[52] U.S. Cl. ........... 252/299.6; 556/428; 252/299.01
[58] Field of Search ............ 252/299.01, 299.6; 556/428

[56] References Cited

U.S. PATENT DOCUMENTS

| | | | |
|---|---|---|---|
| 4,674,842 | 6/1987 | Van De Venne | 349/123 X |
| 4,730,904 | 3/1988 | Pauluth et al. | 349/123 X |
| 5,259,987 | 11/1993 | McCardle et al. | 252/299.01 |
| 5,277,838 | 1/1994 | Haas et al. | 252/299.01 |
| 5,348,684 | 9/1994 | Hemmerling et al. | 252/299.61 |
| 5,550,272 | 8/1996 | Lewis et al. | 556/479 |

FOREIGN PATENT DOCUMENTS

| | | |
|---|---|---|
| 61-286393 | 12/1986 | Japan . |
| 4-29993 | 1/1992 | Japan . |
| 6-9653 | 1/1994 | Japan . |
| 6-312959 | 11/1994 | Japan . |
| 7-2878 | 1/1995 | Japan . |
| 7-2879 | 1/1995 | Japan . |

OTHER PUBLICATIONS

Chem. Abstract 118:124627, 1992.
Nagai et al., J. Organomettalic Chem., 35, pp. 81–89, 1972.
Corey et al., Organomettalics, vol. 12(4). 1121–30, 1993.

*Primary Examiner*—C. H. Kelly
*Attorney, Agent, or Firm*—Wenderoth, Lind & Ponack, L.L.P.

[57] ABSTRACT

An object of the present invention is to provide organosilicon compounds having an excellent miscibility with other liquid crystal materials, low viscosity, and improved threshold voltage; to provide liquid crystal compositions comprising the organosilicon compound; and to provide liquid crystal display devices comprising the liquid crystal composition. The organosilicon compounds are expressed by the general formula (1)

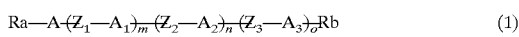

$$Ra-A-(Z_1-A_1)_m-(Z_2-A_2)_n-(Z_3-A_3)_o-Rb \quad (1)$$

wherein at least one of Ra, Rb, $Z_1$, $Z_2$, and $Z_3$ has $-SiH_2-$; Ra represents hydrogen atom or an alkyl group having 1 to 20 carbon atoms; at least one $-CH_2-$ in the alkyl group may be replaced by $-SiH_2-$, $-O-$, $-S-$, $-CO-$, $-CH=CH-$, $-C\equiv C-$, or 1,3-cyclobutylene; Rb represents a group selected from Ra, a halogen atom, or CN; each of A, $A_1$, $A_2$, and $A_3$ represents a divalent cyclic group; $Z_1$, $Z_2$ and $Z_3$ independently represent a covalent bond or $-(CH_2)_p-$; at least one $-CH_2-$ in the $-(CH_2)_p-$ may be replaced by $-SiH_2-$, $-O-$, $-S-$, $-CO-$, $-CH=CH-$, or $-C\equiv C-$; p is an integer of 1 to 4; and m, n, and o are independently 0 or 1.

15 Claims, No Drawings

ORGANOSILICON COMPOUND, LIQUID CRYSTAL COMPOSITION, AND LIQUID-CRYSTAL DISPLAY ELEMENT

This application is a 371 of International Application No. PCT/JP96/02103 filed Jul. 26, 1996.

TECHNICAL FIELD

The present invention relates to an organosilicon compound and liquid crystal composition. More specifically, it relates to a novel compound having silanediyl group (—SiH$_2$—), a liquid crystal composition comprising the compound, and a liquid crystal display device comprising the liquid crystal composition.

BACKGROUND ART

Display devices comprising liquid crystalline compounds (the term "liquid crystalline compounds" is used in this specification as a general term for the compounds exhibiting a liquid crystal phase and for the compounds which do not exhibit a liquid crystal phase but are useful as a component of liquid crystal compositions) have widely been employed for the display of watches, tabletop calculators, word processors, or the likes. These display devices have employed the optical anisotropy and dielectric anisotropy of liquid crystalline compounds.

While liquid crystal phases include a nematic liquid crystal phase, smectic liquid crystal phase, and cholesteric liquid crystal phase, the nematic liquid crystal phase has most widely been employed. As display mode, dynamic scattering (DS) mode, deformation of aligned phase (DAP) mode, guest/host (GH) mode, twisted nematic (TN) mode, super twisted nematic (STN) mode, and thin film transistor (TFT) mode are known.

Liquid crystalline compounds used in these display modes must exhibit a liquid crystal phase in a wide temperature range with room temperature being its center, must be sufficiently stable under conditions in which display devices are used, and further must have characteristics sufficient to drive liquid crystal display devices. However, no liquid crystalline compounds which satisfy such requirements by a single compound have been found up to now. Accordingly, it is the actual circumstances that several or several tens of liquid crystalline compounds are mixed to prepare liquid crystal compositions having required characteristics. These liquid crystal compositions are required to be stable against moisture, light, heat, and air which usually exist under the conditions in which display devices are used; to be stable against electric field and electromagnetic radiation; and to be chemically stable against compounds to be mixed, in addition. Further, it is considered to be necessary that the liquid crystal compositions have an appropriate value of physical properties such as optical anisotropy ($\Delta n$) and dielectric anisotropy ($\Delta \epsilon$), depending on the display mode and the shape of display devices.

Further, it is important that each component in liquid crystal compositions has good miscibility to one another. Particularly, more reduction of consumptive electric power and more lowering of threshold voltage which largely contributes to the high speed response necessary for applying to a wider size of liquid crystal displays (E. Jakeman et al., Phys. Lett., 39A. 69 (1972)) are desired; and it is also important for the high speed response that the liquid crystal compositions have a low viscosity.

In order to achieve these purposes, various compounds have heretofore been developed. Among them, compounds which contain silyl group in the molecule and are expressed by the following formula (a), formula (b), or formula (c) are published by Laid-open Japanese Patent Publication Nos. Hei 6-9653, Hei 7-2878, or Hei 7-2879, respectively.

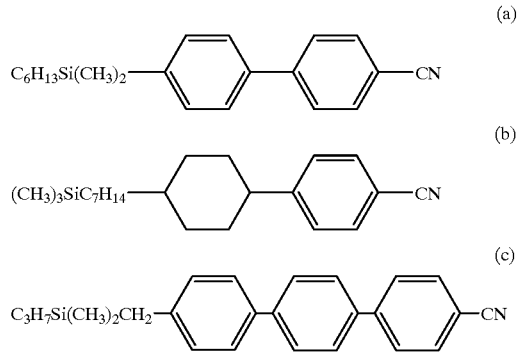

However, these compounds have a trialkylsilyl group formed by substituting three alkyl groups for all three hydrogen atoms linked to silicon atom in silyl group and thus do not have one, particularly two or more unsubstituted hydrogen atoms.

As will be understood from the results of the determination of physical properties conducted by the present inventors, for example, for a compound which has propyldimethylsilyl group and is expressed by the following formula (d), compounds having a trialkylsilyl group have such problems that their viscosity is remarkably high, and besides that their miscibility with other components of liquid crystal compositions is not sufficient.

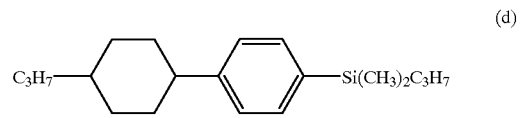

Results of the determination of physical properties of the compound of the formula (d) described above are shown below:

First, the phase transition temperature of a nematic phase-an isotropic phase (NI), and viscosity ($\eta$) at 20° C. were determined on a liquid crystal composition ZLI-1132 produced by Merck Co., Ltd. to be 72.6° C. and 26.7 mPa.s, respectively.

Then, 15 % by weight of the compound expressed by the formula (d) was added to 85 % by weight of the liquid crystal composition, and NI and $\eta$ of the composition thus obtained were determined to be lower than 15° C. and 39.7 mPa.s, respectively.

From the results, it can be understood that the viscosity of liquid crystal compositions prepared by using the compound expressed by the formula (d) remarkably increased and their NI lowered by more than 50° C. Further, the compound expressed by the formula (d) is inadequate for practical purposes since the compound added to the mother liquid crystal composition had a portion having a different NI and was poor in miscibility.

DISCLOSURE OF THE INVENTION

An object of the present invention is to solve the defects in the prior art described above. Another object of the present invention is to provide novel organosilicon compounds which are excellent in miscibility with other liquid crystal materials, have a low viscosity, and have a low threshold voltage; to provide liquid crystal compositions comprising the compound, and to provide liquid crystal display devices comprising the liquid crystal composition.

The present invention for achieving the objects described above is summarized as follows:

(1) An organosilicon compound expressed by the general formula (1)

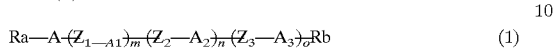

wherein at least one of Ra, Rb, $Z_1$, $Z_2$, and $Z_3$ has —$SiH_2$—; Ra represents hydrogen atom or an alkyl group having 1 to 20 carbon atoms; at least one —$CH_2$— in the alkyl group may be replaced by —$SiH_2$—, —O—, —S—, —CO—, —CH=CH—, —C≡C—, or 1,3-cyclobutylene, but in no case —O— and/or —S— continues; at least one hydrogen atom in Ra may be replaced by a halogen atom or CN; Rb represents a group selected from Ra, a halogen atom, or CN; each of A, $A_1$, $A_2$, and $A_3$ represents a divalent cyclic group and independently represents a cycloalkylene having 3 to 10 carbon atoms, cycloalkenylene having 4 to 10 carbon atoms, cycloalkadienylene having 5 to 10 carbon atoms, phenylene, bicycloalkylene having 4 to 10 carbon atoms, or group of divalent spiro ring having 7 to 12 carbon atoms; at least one —$CH_2$— in these rings may be replaced by —O—, —S—, or —NH—, and at least one —CH= in these rings may be replaced by —N=, respectively; at least one hydrogen atom on the rings may be replaced by a halogen atom or CN; $Z_1$, $Z_2$ and $Z_3$ independently represent a covalent bond or —$(CH_2)_p$—; at least one —$CH_2$— in the —$(CH_2)_p$— may be replaced by —$SiH_2$—, —O—, —S—, —CO—, —CH=CH—, or —C≡C—, but in no case —O— and/or —S— continues; at least one hydrogen atom in $Z_1$, $Z_2$, and $Z_3$ may be replaced by a halogen atom; p is an integer of 1 to 4; and m, n, and o are independently 0 or 1.

(2) The organosilicon compound recited in paragraph (1) above wherein m is 1, and both n and o are 0.

(3) The organosilicon compound recited in paragraph (1) above wherein both m and n are 1, and o is 0.

(4) The organosilicon compound recited in paragraph (1) above wherein all of m, n, and o are 1.

(5) The organosilicon compound recited in paragraph (2) above wherein A and $A_1$ are independently a cycloalkylene, cycloalkenylene, or 1,4-phenylene.

(6) The organosilicon compound recited in paragraph (3) above wherein A, $A_1$ and $A_2$ are independently a cycloalkylene, cycloalkenylene, or 1,4-phenylene.

(7) The organosilicon compound recited in paragraph (4) above wherein A, $A_1$, $A_2$, and $A_3$ are independently a cycloalkylene, cycloalkenylene, or 1,4-phenylene.

(8) A liquid crystal composition comprising at least one organosilicon compound recited in any one of paragraphs (1) to (7) above.

(9) A liquid crystal composition comprising, as a first component, at least one organosilicon compound recited in any one of paragraphs (1) to (7) above, and comprising, as a second component, at least one compound selected from the group consisting of the compounds expressed by any one of the general formulas (2), (3), and (4)

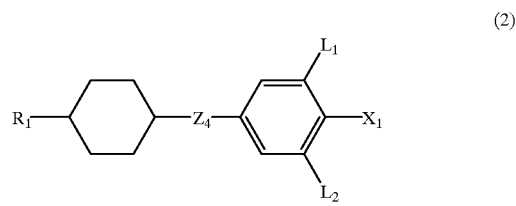

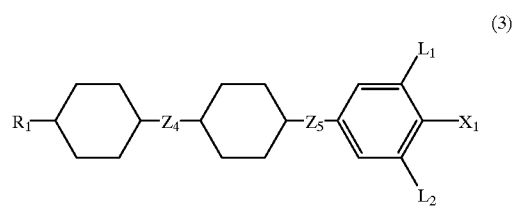

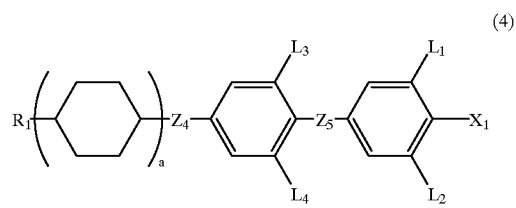

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$ and $L_4$ independently represent H or F; $Z_4$ and $Z_5$ independently represent —$(CH_2)_2$—, —CH=CH—, or a covalent bond; and a is 1 or 2.

(10) A liquid crystal composition comprising, as a first component, at least one organosilicon compound recited in any one of paragraphs (1) to (7) above, and comprising, as a second component, at least one compound selected from the group consisting of the compounds expressed by any one of the general formulas (5), (6), (7), (8), and (9)

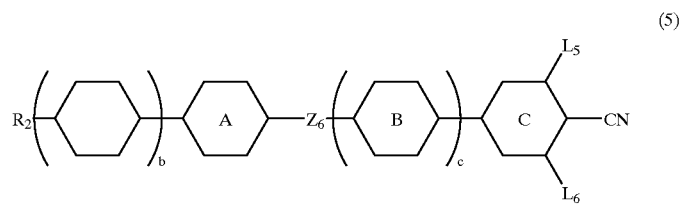

wherein $R_2$ represents F, an alkyl group having 1 to 10 carbon atoms, or an alkenyl group having 2 to 10 carbon atoms; at least one not-adjacent methylene group (—$CH_2$—) in the alkyl or alkenyl group may be replaced by oxygen atom (—O—); ring A represents trans-1,4-cyclohexylene group, 1,4-phenylene group, or 1,3-dioxane-2,5-diyl group; ring B represents trans-1,4-cyclohexylene group, 1,4- phenylene group, or pyrimidine-2,5-diyl group; ring C represents trans-1,4-cyclohexylene group or 1,4-phenylene group; $Z_6$ represents —$(CH_2)_2$—, —COO—, or a covalent bond; $L_5$ and $L_6$ independently represent H or F; and b and c are independently 0 or 1, (6)

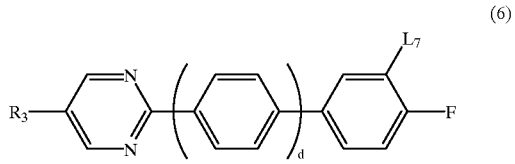

wherein $R_3$ represents an alkyl group having 1 to 10 carbon atoms; $L_7$ represents H or F; and d is 0 or 1,

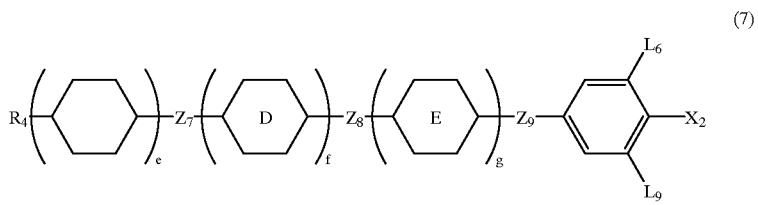

wherein $R_4$ represents an alkyl group having 1 to 10 carbon atoms; ring D and ring E independently represent trans-1, 4-cyclohexylene group or 1,4-phenylene group; $Z_7$ and $Z_8$ independently represent —COO— or a covalent bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$ provided that when $X_2$ represents $OCF_3$, $OCF_2H$, $CF_3$, $CF_2H$, or $CFH_2$, then both $L_8$ and $L_9$ represent H, and e, f, and g are independently 0 or 1, (8)

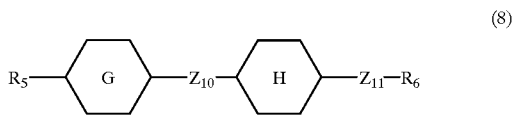

wherein $R_5$ and $R_6$ independently represent an alkyl group having 1 to 10 carbon atoms or an alkenyl group having 2 to 10 carbon atoms; at least one not-adjacent methylene group (—$CH_2$—) in the alkyl or alkenyl group may be replaced by oxygen atom (—O—); ring G represents trans-1,4-cyclohexylene group, 1,4-phenylene group, or pyrimidine-2,5-diyl group; ring H represents trans-1,4-cyclohexylene group or 1,4-phenylene group; $z_{10}$ represents —C≡C—, —COO—, —$(CH_2)_2$—, —CH=CH—C≡C—, or a covalent bond; and $Z_{11}$ represents —COO— or a covalent bond, group (—$CH_2$—) in the alkyl or alkenyl group may be replaced by oxygen atom (—O—); ring I represents trans-1,4-cyclohexylene group, 1,4-phenylene group, or pyrimidine-2,5-diyl group; ring J represents trans-1,4-cyclohexylene group, 1,4-phenylene group at least one hydrogen atom on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —$(CH_2)_2$—, or a covalent bond; $Z_{13}$ represents —CH=CH—, —C≡C—, —COO—, or a covalent bond, and h is 0 or 1.

(11) A liquid crystal composition comprising, as a first component, at least one organosilicon compound recited in any one of paragraphs (1) to (7) above, comprising, as a part of a second component, at least one compound selected from the group consisting of the compounds expressed by any one of the general formula (2), (3), and (4), and comprising, as other part of the second component, at least one compound selected from the group consisting of the compounds expressed by any one the general formulas (5), (6), (7), (8), and (9)

(12) A liquid crystal display device comprising the liquid crystal composition recited in any one of paragraphs (8) to (11) above.

Organosilicon compounds of the present invention expressed by the general formula (1) are excellent in miscibility with other liquid crystal materials, have a low viscosity, and have a low threshold voltage.

These organosilicon compounds are sufficiently stable chemically and physically under conditions in which liquid crystal display devices are usually employed. Besides, organosilicon compounds having desired physical properties can be obtained by selecting proper rings, substituents and/or bonding groups for the molecule constituting elements.

Accordingly, novel liquid crystal compositions having preferable characteristics can be provided when the compound of the present invention is used as component of liquid crystal compositions.

The organosilicon compounds of the present invention are expressed by the general formula (1) described above.

In the formula, Ra represents H, a straight chain or branched alkyl or alkoxy group having 1 to 20 carbon atoms. As the straight chain alkyl group, methyl, ethyl, propyl, butyl, pentyl, hexyl, heptyl, decyl, pentadecyl, and icosyl; as (9)

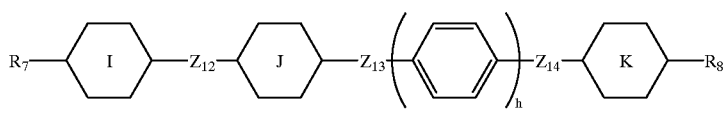

wherein $R_7$ and $R_8$ independently represent an alkyl group having 1 to 10 carbon atoms or an alkenyl group having 2 to 10 carbon atoms; at least one not-adjacent methylene the branched alkyl group, isopropyl, sec-butyl, tert-butyl, isopentyl, isohexyl, 3-ethyloctyl, 3,8-dimethyltetradecyl, and 5-ethyl-5-methylnonadecyl; and as branched alkoxy group, 2-methylpropoxy, 2-methylpentoxy, and 1-methylheptoxymethyl can specifically be mentioned, respectively. The branched alkyl groups or alkoxy groups may be ones exhibiting optical activity.

At least one —CH$_2$— in these alkyl groups may be replaced by —SiH$_2$—, —O—, —S—, —CO—, —CH=CH—, —C≡C—, or 1,3-cyclobutylene unless —O— and/or —S— continues. For instance, as examples of groups substituted with —SiH$_2$—, silanyl groups, alkylsilyl groups, alkoxysilyl groups, alkylsilylalkyl groups, slkoxysilylalkyl groups, alkyldisilanyl groups, alkyldisilanylalkyl groups, and alkyltrisilanyl groups; as examples of groups substituted with —O—, alkoxy groups and alkoxy alkyl groups; as examples of groups substituted with —S—, alkylthioalkyl groups; as examples of groups substituted with —CH=CH—, alkenyl groups, alkadienyl groups, alkenyloxy groups, and alkoxyalkenyl groups; and as examples of groups substituted with —C≡C—, alkynyl groups, alkynyloxy groups, and alkoxyalkynyl groups can be mentioned, respectively.

At least one hydrogen atom in the alkyl groups described above may be replaced by a halogen atom, and as their examples, halogen substituted alkyl groups, halogen substituted alkoxy groups, halogen substituted alkenyl groups, and halogen substituted alkynyl groups can be mentioned.

Among these, preferable groups are specifically mentioned as follows:

As alkyl groups in which at least one —CH$_2$— is replaced by —SiH$_2$—, alkylsilyl groups such as methylsilyl, ethylsilyl, propylsilyl, butylsilyl, pentylsilyl, and nonylsilyl, alkylsilylalkyl groups such as methylsilylmethyl, methylsilylethyl, methylsilylpropyl, methylsilylbutyl, methylsilylheptyl, ethylsilylmethyl, ethylsilylethyl, ethylsilylpropyl, ethylsilylhexyl, propylsilylmethyl, propylsilylethyl, propylsilylpropyl, butylsilylmethyl, butylsilylethyl, butylsilylpropyl, pentylsilylmethyl, hexylsilylmethyl, hexylsilylethyl, heptylsilylmethyl, and octylsilylmethyl, alkoxysilyl groups such as methoxysilyl, ethoxysilyl, propoxysilyl, butoxysilyl, pentyloxysilyl, and oxtyloxysilyl, silanyl groups such as silanyl, disilanyl, trisilanyl, tetrasilanyl, pentasilanyl, and decasilanyl, alkyldisilanyl groups such as methyldisilanyl, ethyldisilanyl, propyldisilanyl, butyldisilanyl, and pentyldisilanyl, alkyltrisilanyl groups such as methyltrisilanyl, ethyltrisilanyl, propyltrisilanyl, and hexyltrisilanyl, alkyldisilanylalkyl groups such as methylnonasilanyl, methyldisilanylmethyl, methyldisilanylethyl, methyldisilanylpentyl, ethyldisilanylmethyl, ethyldisilanylethyl, ethyldisilanylbutyl, ethyldisilanylhexyl, propyldisilanylmethyl, butyldisilanylpentyl, pentyldisilanylmethyl, hexyldisilanylethyl, and heptyldisilanylmethyl, alkyltrisilanylalkyl groups such as methyltrisilanylmethyl, methyltrisilanylpentyl, ethyltrisilanylmethyl, ethyltrisilanylpropyl, propyltrisilanylmethyl, propyltrisilanylbutyl, butyltrisilanylmethyl, pentyltrisilanylmethyl, and hexyltrisilanylmethyl, and groups such as methylhexasilanylmethyl, ethylheptasilanylmethyl, methyloctasilanylmethyl, 2-fluoroethylsilyl, 3,3-difluoropropylsilyl, and 1,2,3,3-tetrafluoropropylsilyl.

As groups in which —CH$_2$— in the group is replaced by —O—, alkoxy groups such as methoxy, ethoxy, propoxy, butoxy, pentyloxy, and nonyloxy, and alkoxyalkyl groups such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl, and octyloxymethyl can be mentioned.

Further, the following groups can be mentioned:

Alkylthioalkyl groups such as methylthiomethyl, methylthioethyl, methylthioethyl, methylthiopropyl, methylthiobutyl, methylthiooctyl, ethylthiomethyl, ethylthioethyl, ethylthioheptyl, propylthiomethyl, propylthioethyl, propylthiopropyl, propylthiopentyl, hexylthiomethyl, and heptylthioethyl, groups such as methylcarbonyl, ethylcarbonyl, propylcarbonyl, methoxycarbonyl, ethoxycarbonyl, propoxycarbonyl, butoxycarbonyl, heptyloxycarbonyl, 2-oxopropyl, 2-oxobutyl, 3-oxobutyl, 2-oxopentyl, 4-oxopentyl, 3-oxohexyl, 5-oxohexyl, 2-oxoheptyl, 3-oxoheptyl, 6-oxoheptyl, 2-oxooctyl, 4-oxooctyl, 7-oxooctyl, 3-oxononyl, 6-oxononyl, 8-oxononyl, 2-oxodecyl, 5-oxodecyl, and 9-oxodecyl, alkenyl groups such as vinyl, propenyl, butenyl, pentenyl, hexenyl, and decenyl, alkoxyalkenyl groups such as methoxypropenyl, ethoxypropenyl, pentyloxypropenyl, methoxybutenyl, ethoxybutenyl, pentyloxybutenyl, methoxypentenyl, propoxypentenyl, methoxyhexenyl, propoxyhexenyl, methoxyheptenyl, and methoxyoctenyl, alkenyloxy groups such as propenyloxy, butenyloxy, pentenyloxy, octenyloxy, and propenyloxymethyl, groups such as propenyloxyethyl, propenyloxybutyl, butenyloxymethyl, butenyloxyethyl, butenyloxypentyl, pentenyloxymethyl, pentenyloxypropyl, hexenyloxymethyl, hexenyloxyethyl, heptenyloxymethyl, and octenyloxymethyl, alkadienyl groups such as butadienyl, heptadienyl, hexadienyl, heptadienyl, octadienyl, and icosadienyl, halogen substituted alkenyl groups such as 3-fluoropropenyl, 4-fluoro-1-butenyl, 4-fluoro-2-butenyl, 5-fluoro-1-pentenyl, 5-fluoro-2-pentenyl, 5-fluoro-3-pentenyl, 6-fluoro-1-hexenyl, 6-fluoro-3-hexenyl, 7-fluoro-5-heptenyl, 2,2-difluorovinyl, 1,2-difluorovinyl, 2-chloro-2-fluorovinyl, 2-bromo-2-fluorovinyl, 2-fluoro-2-cyanovinyl, 3,3-difluoro-2-propenyl, 3-chloro-3-fluoro-1-propenyl, 2,3-difluoro-1-propenyl, 1,3-difluoro-2-propenyl, 1,3,3-trifluoro-2-propenyl, 1,2,4,4-tetrafluoro-3-butenyl, 5,5-difluoro-4-pentenyl, 3,3-difluorohexenyl, and 8,8-difluoro-7-octenyl, alkynyl groups such as ethynyl, propynyl, butynyl, pentynyl, and octynyl, alkynyloxy groups such as ethynyloxy, propynyloxy, butynyloxy, pentynyloxy, and tetradecynyloxy, alkoxyalkynyl groups such as methoxypropynyl, methoxypentynyl, ethoxybutynyl, propoxypropynyl, hexyloxyheptynyl, methoxymethylbutynyl, methoxypropylethynyl, and butoxymethylpropynyl, halogen substituted alkyl groups such as fluoromethyl, difluoromethyl, trifluoromethyl, 2-fluoroethyl, 1,2-difluoroethyl, 2-bromo-1,2-difluoroethyl, 3-fluoropropyl, 1,2,3,3-tetrafluoropropyl, 4-fluorobutyl, 1,1,2,4-tetrafluorobutyl, 5-fluoropentyl, 2,3,3,4,5-pentafluoropentyl, 6-fluorohexyl, 2,3,4,6-tetrafluorohexyl, 7-fluoroheptyl, and 8,8-difluorooctyl, and halogen substituted alkoxy groups such as difluoromethoxy, trifluoromethoxy, 1,1-difluoroethoxy, 2,2- difluoroethoxy, 2,2,2-trifluoroethoxy, 1,1,2,2-tetrafluoroethoxy, perfluoroethoxy, 1,1,2,3,3,3-hexafluoropropoxy, and perfluoropropoxy.

Next, while Rb is a group selected from the Ra described above, a group selected from halogen atoms including F, Cl, Br, and I, or CN, Rb is preferably those groups excluding Br and I from the viewpoint of stability and others.

While A, $A_1$, $A_2$, and $A_3$ represent a cycloalkylene having 3 to 10 carbon atoms at least one hydrogen atom on which ring may be replaced by a halogen atom or CN, a cycloalkenylene having 4 to 10 carbon atoms, a cycloalkadienylene having 5 to 10 carbon atoms, phenylene, a divalent group of a cyclic compound containing a hetero atom, a bicycloalkylene having 4 to 10 carbon atoms, or a divalent group of spiro ring having 7 to 12 carbon atoms, respectively, the following can specifically be mentioned:

As the cycloalkylenes described above, cyclopropylene, cyclobutylene, cyclopentylene, cyclohexylene, cycloheptylene, and cyclodecylene, as cycloalkenylenes, cyclopentenylene, cyclohexenylene, cycloheptenylene, and cyclononenylene, as cycloalkadienylenes, cyclohexadienylene, cyclopentadienylene, and cyclodecadienylene, as divalent groups of a ring compound containing a hetero atom, piperidinediyl, piperazinediyl, pyridinediyl, pyrazinediyl, pyrimidinediyl, pyridazinediyl, triazinediyl, tetrazinediyl, tetrahydropyrandiyl, dioxanediyl, and dithianediyl, as bicycloalkylenes, bicyclobutanediyl, bicyclopentanediyl, bicyclohexanediyl, bicycloheptanediyl, bicyclooctanediyl, and bicyclooctenediyl, and as divalent groups of a spiro ring, spiroheptanediyl, spirobicyclohexanediyl, spirooctanediyl, spirodecanediyl, cyclohexanespirobutanediyl, cyclohexenespirocyclobutanediyl, and cyclohexenespriocyclohexenediyl.

As more preferable groups among these, the followings can be mentioned:

As cycloalkylenes, 1,2-cyclopropylene, 1,3-cyclobutylene, and 1,4-cyclohexylene, as cycloalkenylenes, 1-cyclohexene-1,4-ylene, 2-cyclohexene-1,4-ylene, and 3-cyclohexene-1,4-ylene, as phenylenes, 1,4-phenylene, and a group in which at least one hydrogen atom on which ring is replaced by a halogen atom or CN, for example, 2-fluoro-1,4-phenylene, 3-fluoro-1,4-phenylene, 2,3-difluoro-1,4-phenylene, 3,5-difluoro-1,4-phenylene, 2,3,5-trifluoro-1,4-phenylene, 2-chloro-1,4-phenylene, 3-chloro-1,4-phenylene, 2,3-dichloro-1,4-phenylene, 3,5-dichloro-1,4-phenylene, 3-bromo-1,4-phenylene, 2-iodo-1,4-phenylene, 2-chloro-3-fluorophenylene, 3-fluoro-5-chlorophenylene, 2-cyano-1,4-phenylene, 3-cyano-1,4-phenylene, and 2,3-dicyano-1,4-phenylene, and as divalent groups of monocyclic compound containing a hetero atom, pyridine-2,5-diyl, pyrimidine-2,5-diyl, tetrahydropyran-2,5-diyl, and dioxane-2,5-diyl.

While $Z_1$, $Z_2$, and $Z_3$ represent a covalent bond or an alkylene having 1 to 4 carbon atoms at least one hydrogen atom in the alkylene may be replaced by a halogen atom, more preferably they represent a covalent bond, ethylene, or butylene. Further, whereas the methylene group in the alkylene may be replaced by —SiH$_2$—, —O—, —CH=CH—, or —C≡C—, in no case —O— and/or —S— continues at that time.

As such groups, the following can preferably be mentioned:

Groups, having —SiH$_2$— as substituent, such as 1,2-disilanediyl, 1,4-tetrasilanediyl, methylenesilanediyl, silanediylmethylene, methylenesilanediyltrimethylene, methylenesilanediylethylene, and ethylenesilanediylmethylene, groups, having —O— as substituent, such as oxymethylene, methylenoxy, oxytrimethylene, methylenoxyethylene, ethylenoxymethylene, and ester bond, groups, having —CH=CH— as substituent, such as vinylene, 1-butenylene, 2-butenylene, and 3-butenylene, groups, having —C≡C— as substituent, such as ethynylene, 1-butynylene, 2-butynylene, and 3-butynylene, groups formed by replacing at least one hydrogen atom in each of the groups mentioned above by a halogen atom, for example, fluoromethylenoxy, oxyfluoromethylene, difluoromethylenoxy, oxydifluoromethylene, 2,2-difluoroethylene, 1,2-difluorovinylene, 1-fluorovinylene, 1-bromo-2-fluorovinylene, 1-chloro-2-fluorovinylene, 1,2-difluoro-1-butenylene, 2,3-difluoro-2-butenylene, and 3,4-difluoro-3-butenylene, and 3-oxy-1-propenylene and 2-propenyloxy.

While the compounds of the present invention expressed by the general formula (1) and constituted by the groups selected from each of Ra, Rb, A to $A_3$, and $Z_1$ to $Z_3$ described above have preferable properties, the compounds more preferably do not have two or more rings containing a hetero atom.

Among such a group of compounds, a group of compounds having particularly preferable properties are expressed by one of the following formulas (1-1) to (1-59):

(1-1)

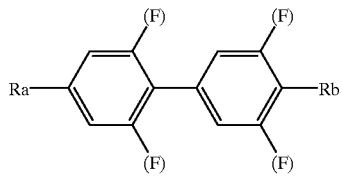

(1-2)
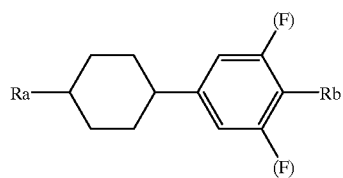
(1-3)
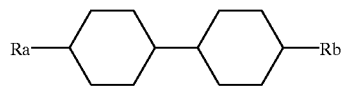
(1-4)
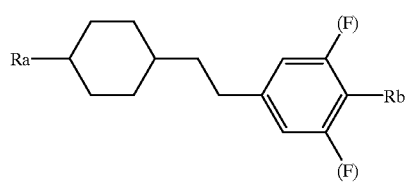
(1-5)
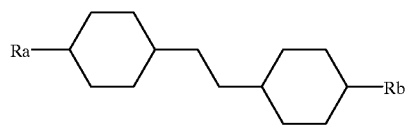
(1-6)
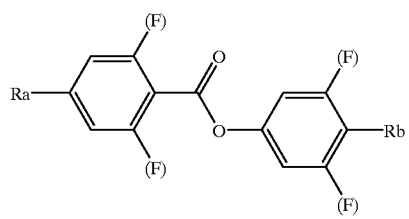
(1-7)
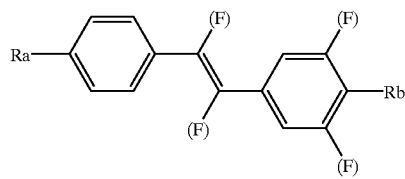
(1-8)
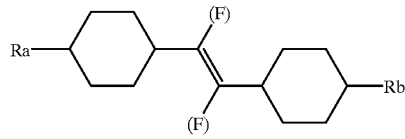
(1-9)
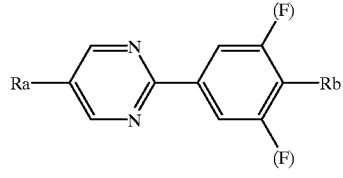
(1-10)
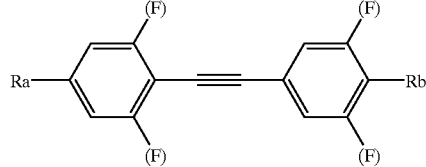

-continued
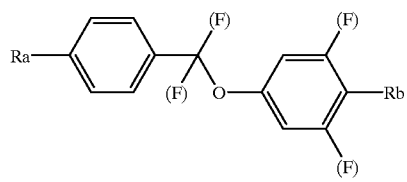
(1-11)
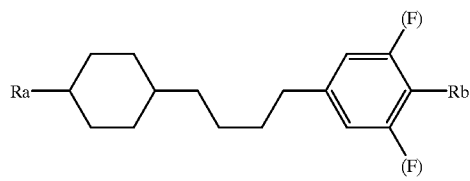
(1-12)
(1-13)
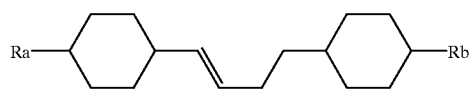
(1-14)
(1-15)
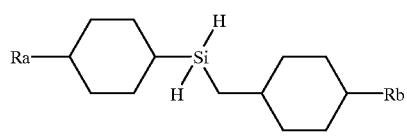
(1-16)
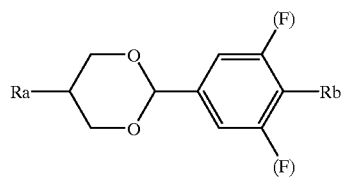
(1-17)
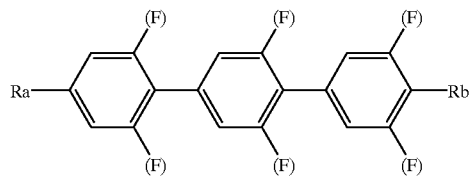
(1-18)
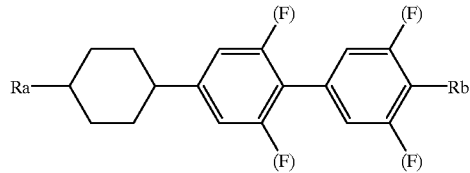
(1-19)

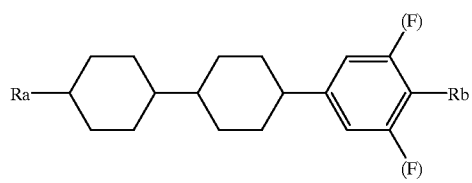 (1-20)
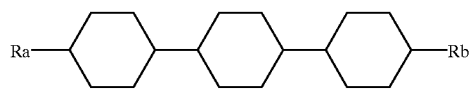 (1-21)
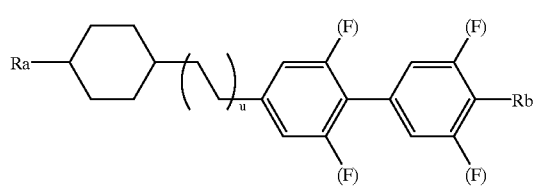 (1-22)
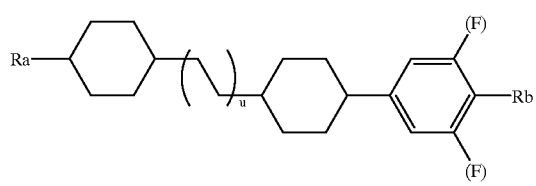 (1-23)
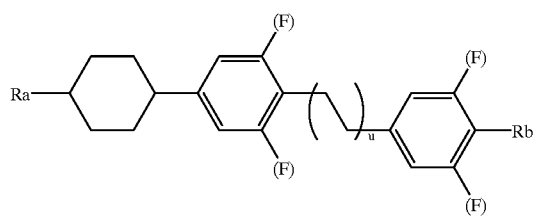 (1-24)
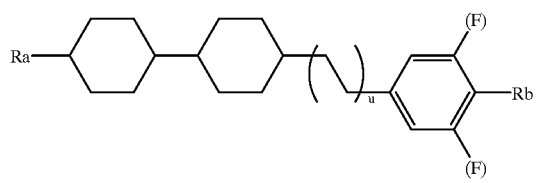 (1-25)
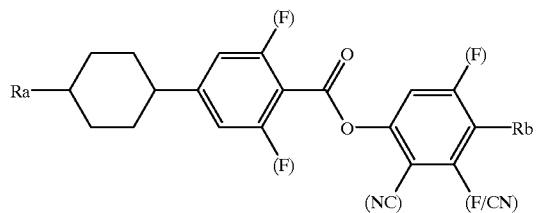 (1-26)
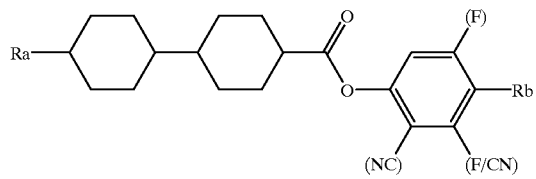 (1-27)

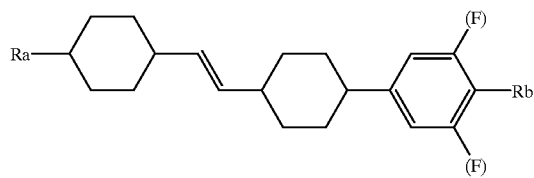 (1-28)
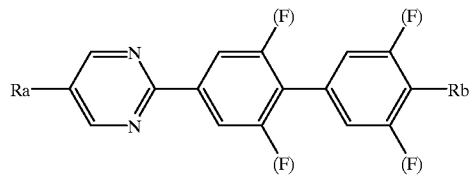 (1-29)
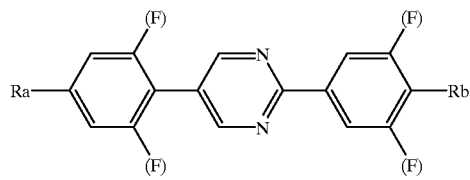 (1-30)
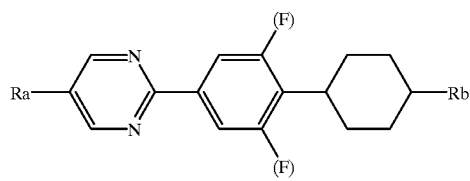 (1-31)
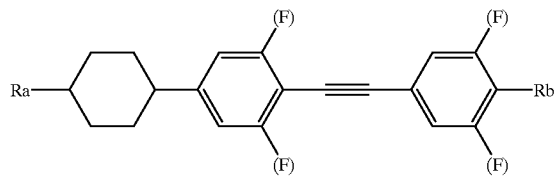 (1-32)
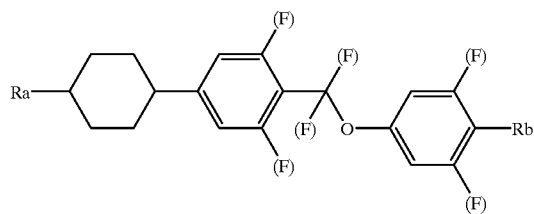 (1-33)
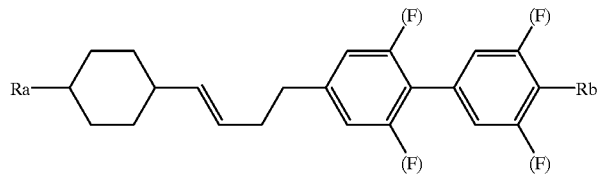 (1-34)
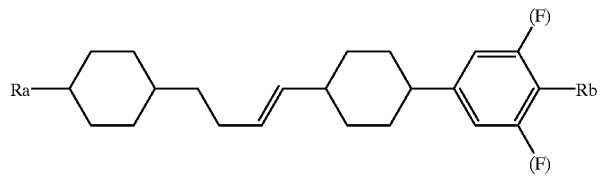 (1-35)

(1-36)
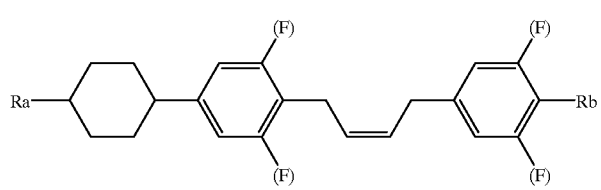
(1-37)
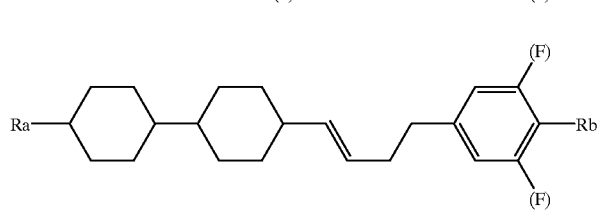
(1-38)
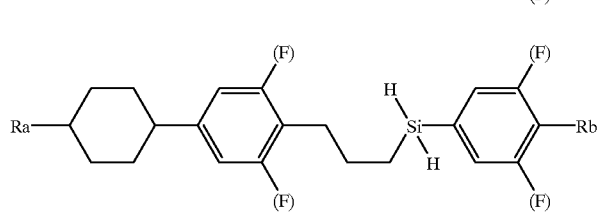
(1-39)
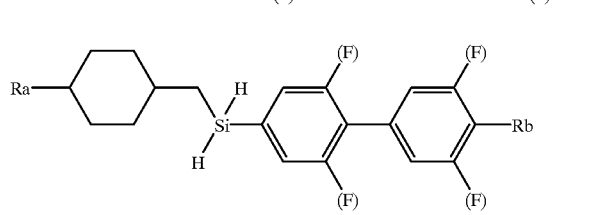
(1-40)
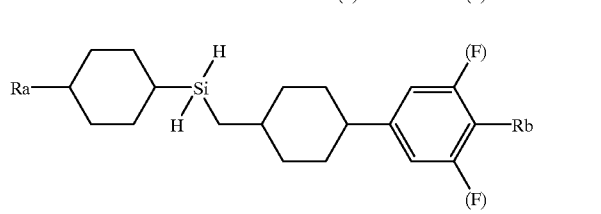
(1-41)
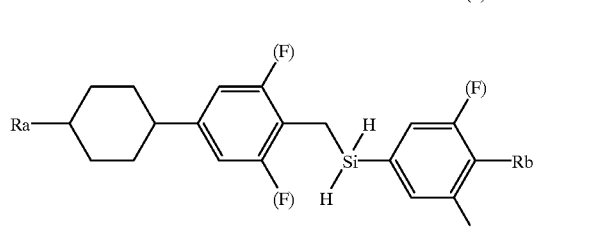
(1-42)
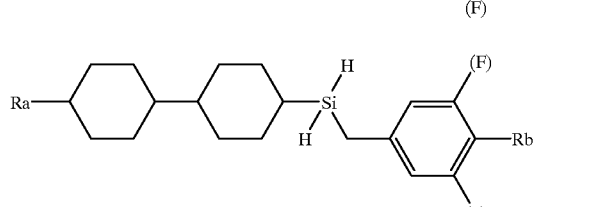
(1-43)
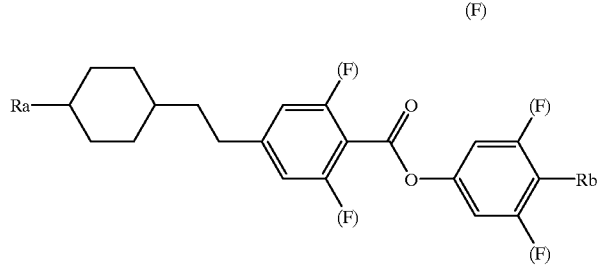

-continued
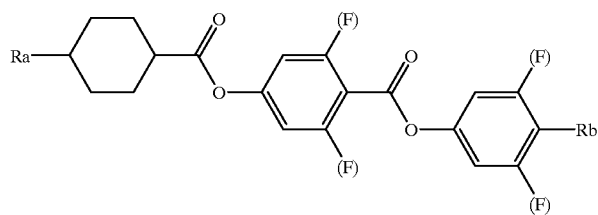
(1-44)
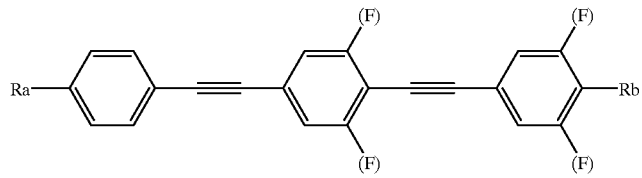
(1-45)
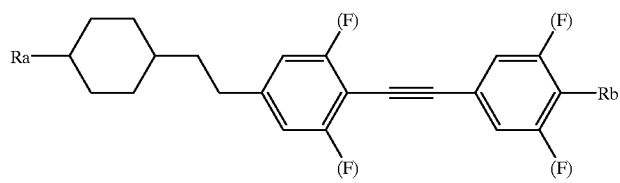
(1-46)
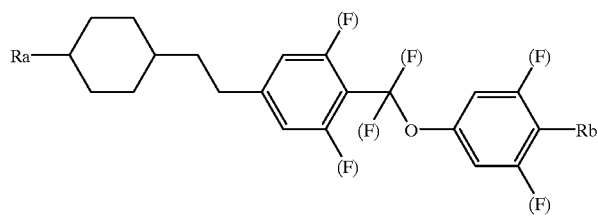
(1-47)
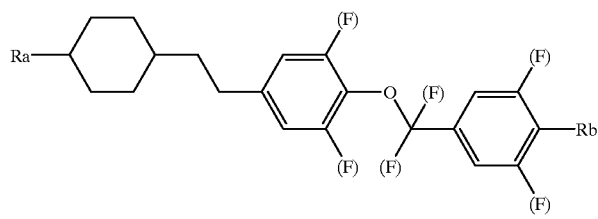
(1-48)
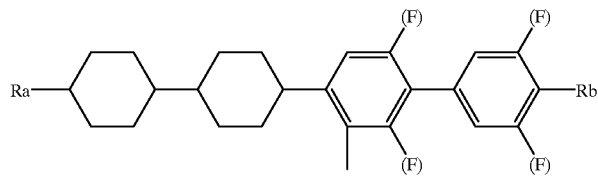
(1-49)
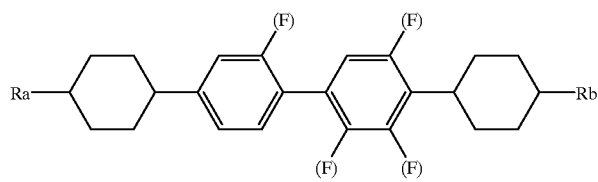
(1-50)

-continued
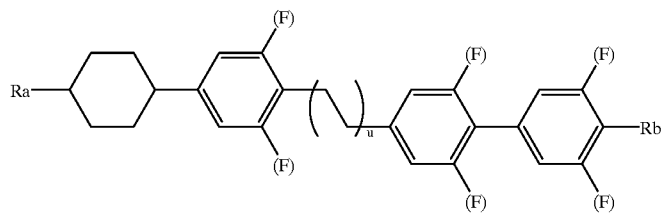
(1-51)
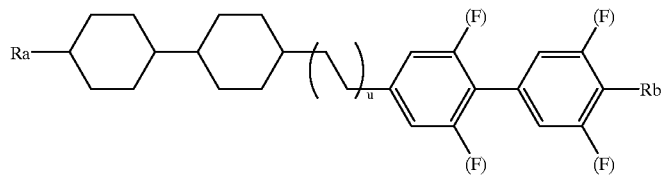
(1-52)
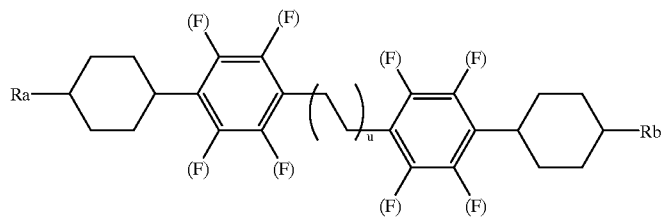
(1-53)
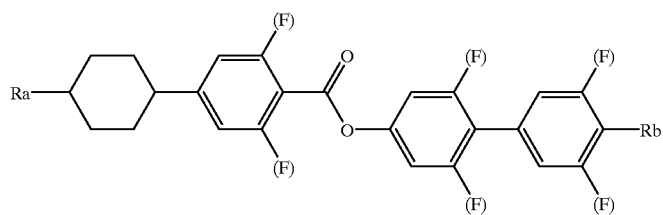
(1-54)
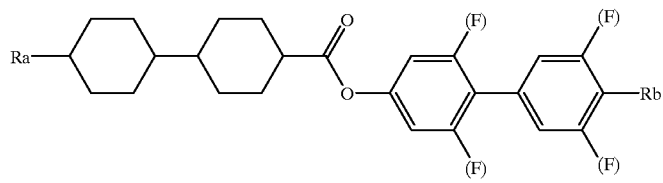
(1-55)
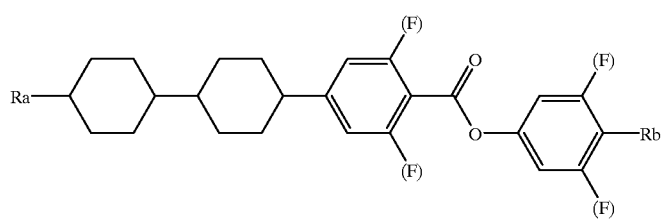
(1-56)
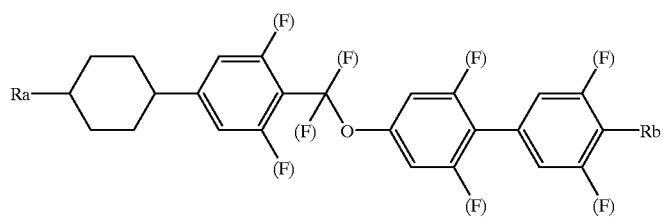
(1-57)

(1-58)

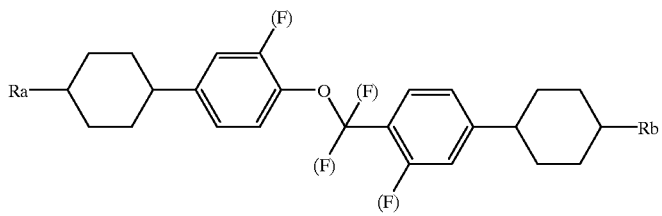

(1-59)

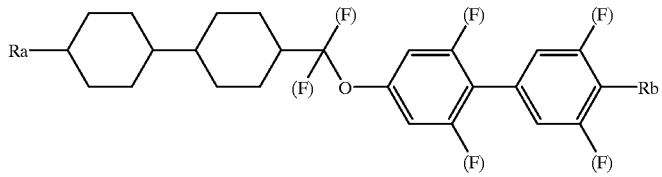

wherein Ra and Rb have the same meaning as that described above, u is 1 or 2, and hydrogen atom on the ring and/or in the bonding group may independently be replaced by a group shown in the parenthesis.

Compounds of the present invention expressed by the general formula (1) can be obtained by introducing a certain group at Ra, Rb, $Z_1$, $Z_2$, and $Z_3$, and the introduction of such groups can be carried out by a general method of organic synthesis heretofore known to the public.

Introduction of silanediyl group:

Silanediyl group can be introduced by a general known method of organic synthesis described in the literature, for example, E. W. Colvin et al., Silicon in Organic Synthesis, Butterworths, London (1981), W. P. Weber, Silicon Reagents for Organic Synthesis, Springer-Verlag, Berlin (1983), and E. W. Colvin, Silicon Reagents in Organic Synthesis, Academic Press, London (1988).

Some specific examples of the methods described in the literature are shown below:

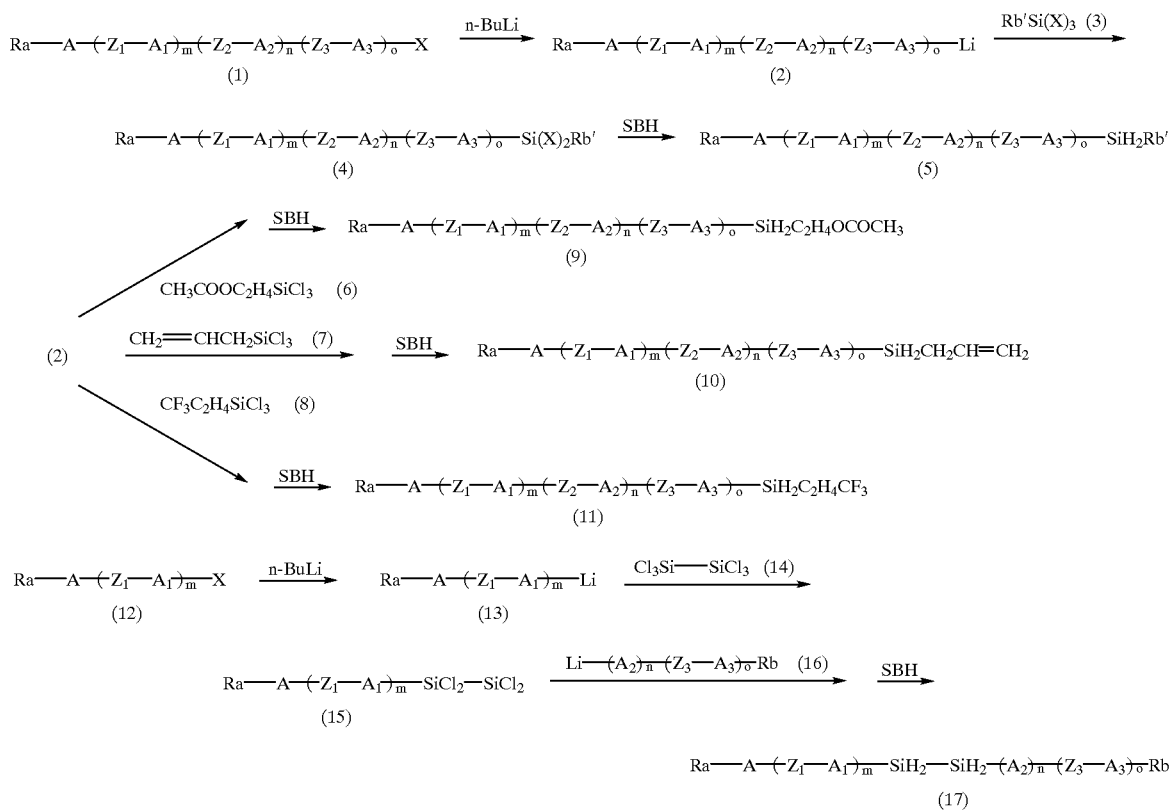

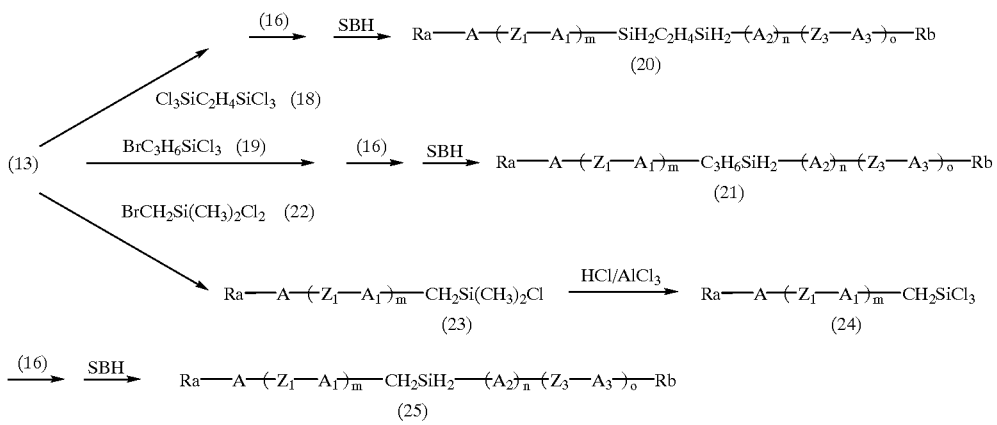

wherein Ra, Rb, m, n, o, A, $A_1$ to $A_3$, and $Z_1$ to $Z_3$ have the same meaning as that described above, X represents a halogen atom, and Rb' represents a residual group formed by taking off —$SiH_2$— from Rb.

That is, in a first method, after lithium reagent (2) was prepared from halide (1) in which a terminal group corresponding to Rb is a halogen including Br and I expressed by X, and Li, n-BuLi, or tert-BuLi, the lithium reagent (2) is reacted with alkylhalogenated silane (3) such as alkyltrichlorosilane to prepare compound (4). The compound (4) can be reduced with a reducing agent such as sodium boron hydride (SBH) and lithium aluminum hydride (LAH) to produce objective compound (5), as an example, in which X is converted to Rb(SiH$_2$Rb'). Further, organosilicon compound (9), (10), or (11) can be obtained by using a corresponding halogenated silane such as (6), (7), or (8) in place of the alkylhalogenated silane (3) mentioned above.

Also, the reaction can be carried out in the same manner even when a Grignard reagent prepared from the halide (1) and Mg is used instead of the lithium reagent (2) mentioned above.

In a second method, after lithium reagent (13) or a Grignard reagent was prepared from halide (12) by such a method as described above, the reagent is reacted with hexachlorodisilane (14) obtained by the same method as that described in Sakurai et al. (Tetrahedron Letters, 5493 (1966)) to convert it into compound (15). After reacted with lithium reagent (16) or a Grignard reagent, the compound (15) can be reduced to produce objective compound (17), as an example, having —$SiH_2$— at the center portion of the molecule.

Also, organosilicon compounds (20) and (21) each having —$SiH_2$— at the center portion of the molecule can be produced by using a corresponding halogenated silane such as (18) or (19) instead of the hexachlorodisilane (14) mentioned above.

Further, compound (23) is prepared by using halogenated silane (22) instead of the hexachlorodisilane (14) mentioned above. After the compound (23) was converted into trichlorosilane (24) by the method of Sakurai et al. described above and reacted with the lithium reagent (16), it can be reduced to produce objective compound (25), as an example, having —$SiH_2$— at the center portion of the molecule.

Besides; although an illustration is omitted in the specification, a silanediyl group can be introduced by subjecting an olefin or acetylene, and a substituted dihalogenated hydrosilane to a hydrosilylation in the presence of a radical initiator such as azobisisobutronitrile, benzoil peroxide, or di-tert-butyl peroxide, or a transition metal catalyst such as Pt, Rh, Pd, or Ni (B. A. Bluestein, Journal of the American Chemical Society, 83, 1000 (1961); R. A. Benkeser et al., Journal of the American Chemical Society, 83, 4385 (1961); J. L. Speier et al., Journal of the American Chemical Society, 79, 974 (1957)), and then reducing the halogen atom.

Introduction of groups (—CH=CH—, —C≡C—, —CO—, —O—) other than silanediyl group:

These groups can also be introduced by a general method of organic synthesis heretofore known to the public.

Group —CH=CH— can readily be introduced in the molecule of a compound, for instance, by the Wittig reaction (Organic Reactions, Volume 14, Chapter 3), Wittig-Schlosser Reaction (M. Schlosser et al., Angewandt Chemie, International Edition in English, 5, 126 (1966), or Wittig-Horner reaction (J. I. G. Cadogan, Organophosphorus Reagents in Organic Synthesis, Academic (1979).

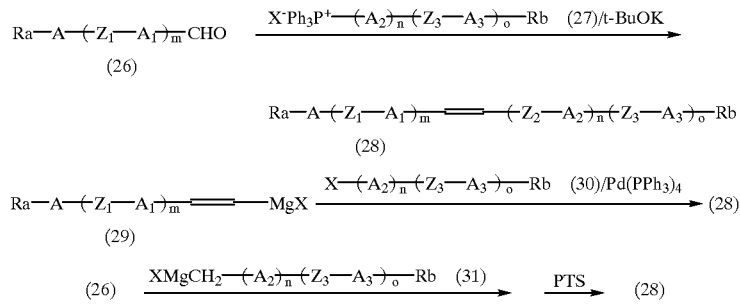

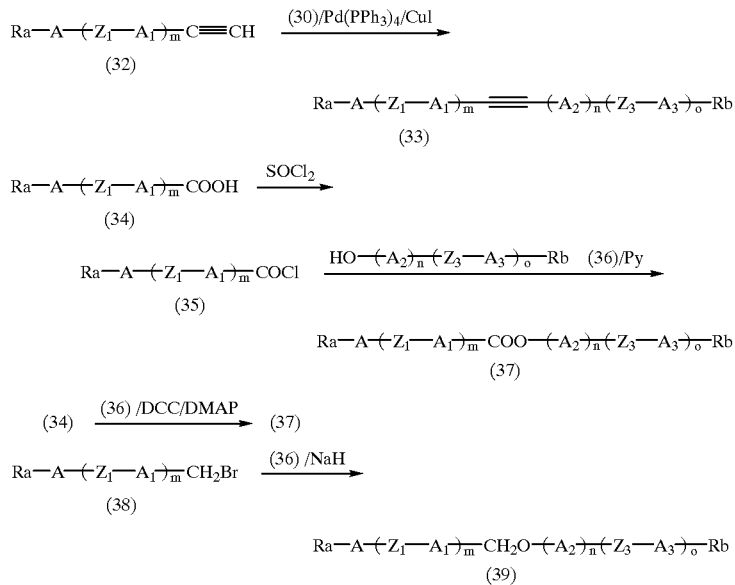

wherein Ra, Rb, Rb', m, n, o, A, $A_1$ to $A_3$, $Z_1$ to $Z_3$, and X have the same meaning as that described above.

That is, compound (28) in which —CH=CH— is introduced can be produced by reacting aldehyde (26) with phosphonium salt (27) in a solvent such as tetrahydrofuran and diethyl ether in the presence of a base such as potassium-tert-butoxide (t-BuOK) and n-butyl lithium. This reaction is preferably carried out at a temperature of room temperature to −50° C. under an atmosphere of an inert gas. Further, the compound thus obtained can be isomerized by reacting it with benzenesulfinic acid or p-toluenesulfinic acid. Alternatively, the compound (28) can be produced by a method (T. V. Lee et at., Tetrahedron Letters, 46, 921 (1990)) in which vinyl-Grignard reagent (29) and halide (30) are subjected to a coupling reaction in the presence of a catalyst such as $Pd(PPh_3)_4$, $PdCl_2(PPh_3)_2$, and $NiCl_2(dppp)$ or by a method in which the aldehyde (26) and Grignard reagent (31) are reacted and then heated to dehydrate in a solvent such as toluene and xylene in the presence of an acidic catalyst such as p-toluenesulfonic acid (PTS).

Compound (33) containing —C≡C— can be produced, for instance, by a method of W. Tao et al. (The Journal of Organic Chemistry, 55, 63 (1990)). That is, the compound (33) can be produced by reacting acetylene derivative (32) with the halide (30) mentioned above in an alkylamine solvent such as diethylamine and triethylamine in the presence of copper iodide and a Pd catalyst such as $Pd(PPh_3)_4$ and $PdCl_2(PPh_3)_2$. This reaction is preferably carried out in the temperature range from room temperature to the boiling point of the solvent under an atmosphere of an inert gas. Also, the compound (33) can also be produced by carrying out the Castro reaction (M. D. Raush et al., The Journal of Organic Chemistry, 34, 468 (1969)).

Compound (37) containing —COO— can be produced, for instance, by a method of E. J. Corey et al. (The Journal of Organic Chemistry, 38, 3223 (1973)). That is, the compound (37) can be produced by converting carboxylic acid (34) into acid halide (35) with a halogenating agent such as thionyl chloride in a solvent such as toluene and benzene or in the absence of a solvent, and then reacting the acid halide (35) with alcohol (36). This reaction is preferably carried out in the temperature range from room temperature to the boiling point of the solvent under an atmosphere of an inert gas. More desirably, the reaction is conducted, for accelerating the reaction, in the presence of a base such as pyridine, triethylamine (B. Iselin et al., Helvetica Chimica Acta, 40, 373 (1957)), dimethyl aniline (C. Raha, Organic Synthesis, IV, 263 (1963)), or tetramethylurea (M. S. Newman et al., Tetrahedron Letters, 3267 (1967)). Alternatively, the compound (37) can be produced by reacting the carboxylic acid (34) with the alcohol (36) in a solvent such as dichloromethane and chloroform in the presence of a dehydrating agent such as dicyclohexylcarbodiimide (DCC) and 4-dimethylaminopyridine (DMAP) (B. Neises et al., Organic Synthesis, 63, 183 (1985)).

Compound (39) containing —O— can be produced, for instance, by reacting halide (38) with the alcohol (36) mentioned above in a solvent such as dimethyl sulfoxide, dimethyl formamide, 1,2-dimethoxyethane, tetrahydrofuran, hexamethylphosphoric acid triamide, or toluene in the presence of a base such as sodium amide (J. B. Wright et al., Journal of the American Chemical Society, 70, 3098 (1948)), potassium carbonate (W. T. Olson et al., Journal of the American Chemical Society, 69, 2451 (1947)), triethylamine (R. L. Merker et al., The Journal of Organic Chemistry, 26, 5180 (1961)), sodium hydroxide (C. Wilkins, Synthesis, 1973, 156), potassium hydroxide (J. Rebek et al., The Journal of Organic Chemistry, 44, 1485 (1979)), barium oxide (Kawabe et al., The Journal of Organic Chemistry, 37, 4210 (1972)), sodium hydride (C. J. Stark, Tetrahedron Letters, 22, 2089 (1981) and K. Takai et al., Tetrahedron Letters, 21, 1657 (1980)).

At least one hydrogen atom in the compounds of the present invention in which a prescribed group is introduced may further be replaced by a halogen atom. The replacement may be carried out, for instance, by a method in which hydrogen atom on the ring is directly halogenated (H. Becker et al., Organikum, VEB, Deutscher Verlag der Wissenschaften, 189 (1973); Uemura et al., Bulletin of the Chemical Society of Japan, 47, 147 (1974); and D. D. Tanner et al., Journal of the American Chemical Society, 90, 808 (1968)) or by a method in which hydroxyl group is halogenated (G. A. Wiley et al., Journal of the American Chemical Society, 86, 964 (1964); E. J. Corey et al., The Journal of Organic Chemistry, 32, 4160 (1967); G. Hilgetag et al., Preparative Organic Chemistry, John Wiley, 217 (1975); H. Becker et al., Organikum, VEB, Deutscher Verlag der Wissenschften, 212 (1973); H. Steone et al., Organic Synthesis, IV, 323 (1963); and G. A. Olah et al., Synthesis, 653 (1974)).

An example of the former method is shown as follows:

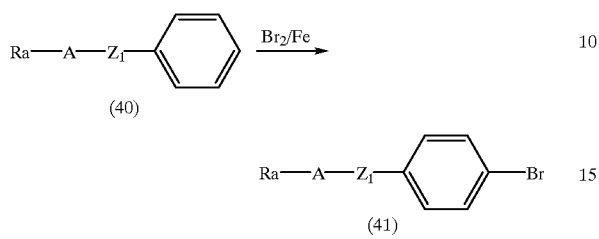

wherein Ra, A, and $Z_1$, have the same meaning as that described above.

That is, bromide (41) can be produced by reacting aromatic compound (40) with bromine in a solvent such as chloroform and carbon tetrachloride in the presence of a catalyst such as iron powder. This reaction is preferably carried out under an atmosphere of an inert gas at a temperature of −20 to 150° C.

While all of the reactions described above are known in the public, it is needless to say that other known reactions can further be used when necessary. Whereas the introduction of a silanediyl group is conducted at the final stage, in the reactions described above, it is possible to conduct the introduction at an initial stage and then conduct a reaction such as esterification to produce an objective compound. The time of the introduction may be properly selected.

While general methods for producing the compounds of the present invention have been described above, other methods wherein a silanediyl group is introduced particularly at a terminal portion are described in more detail below:

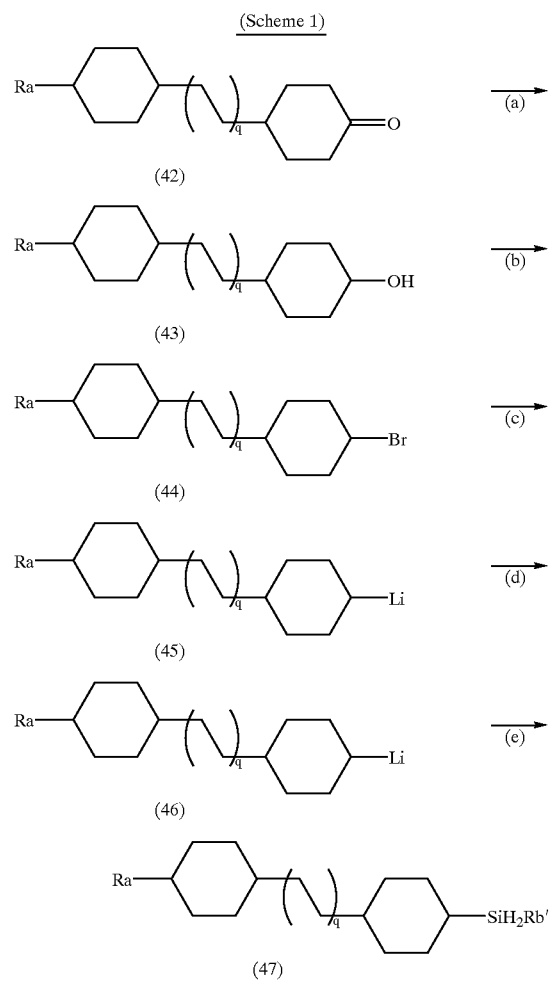

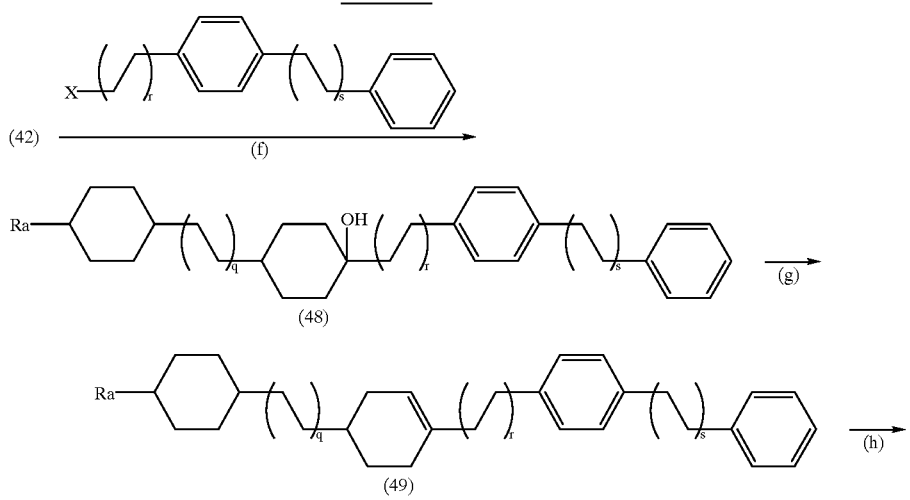

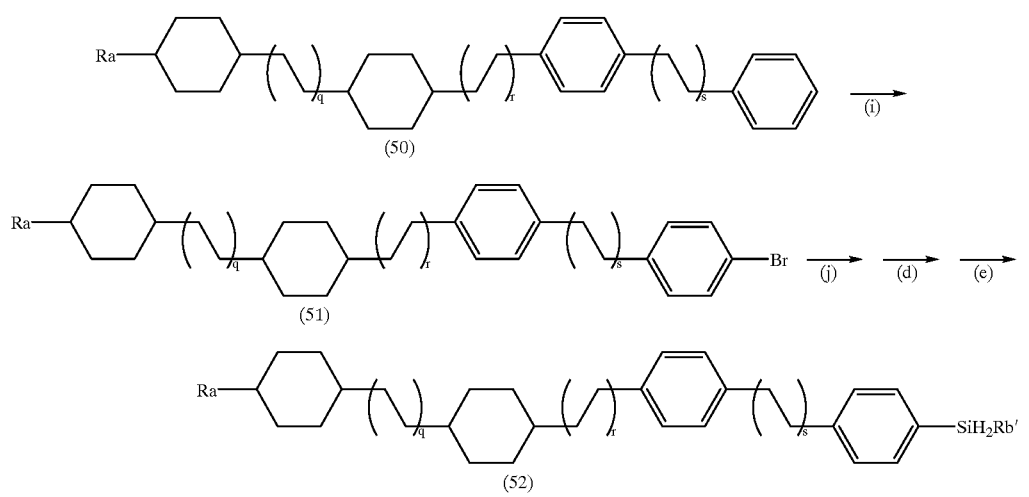
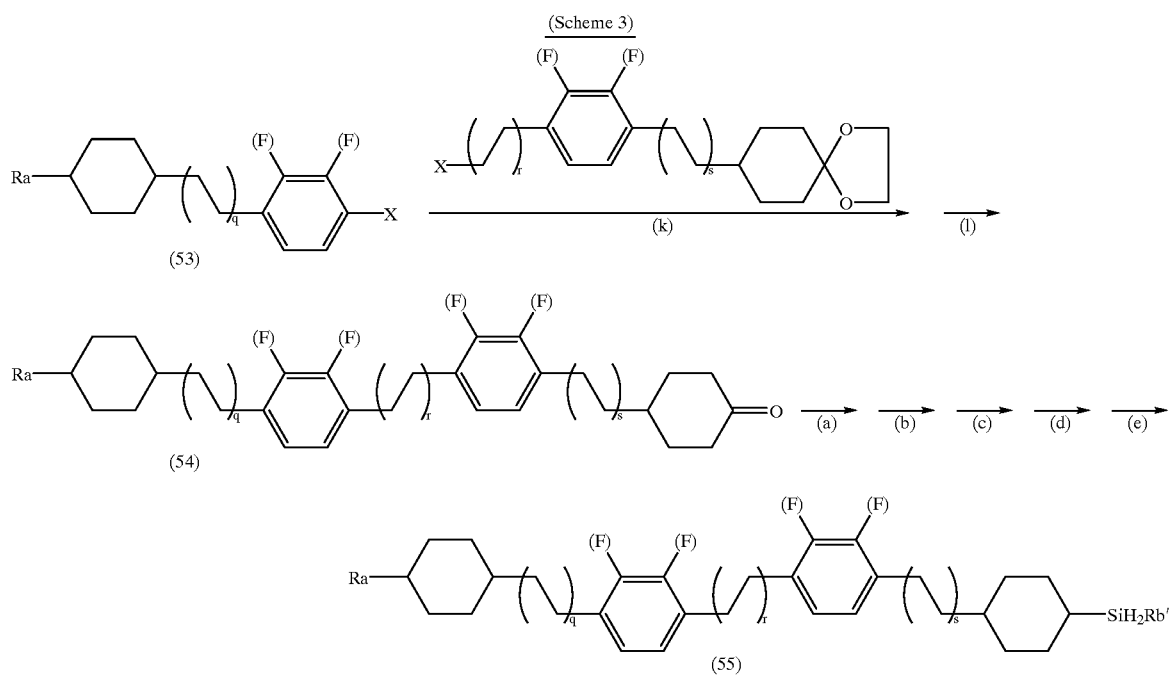
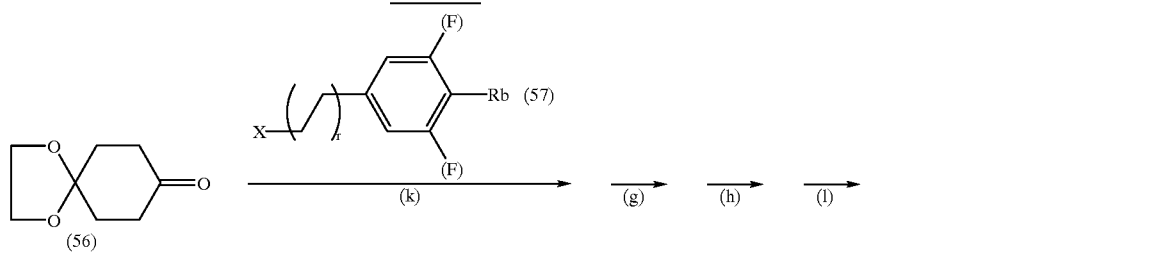

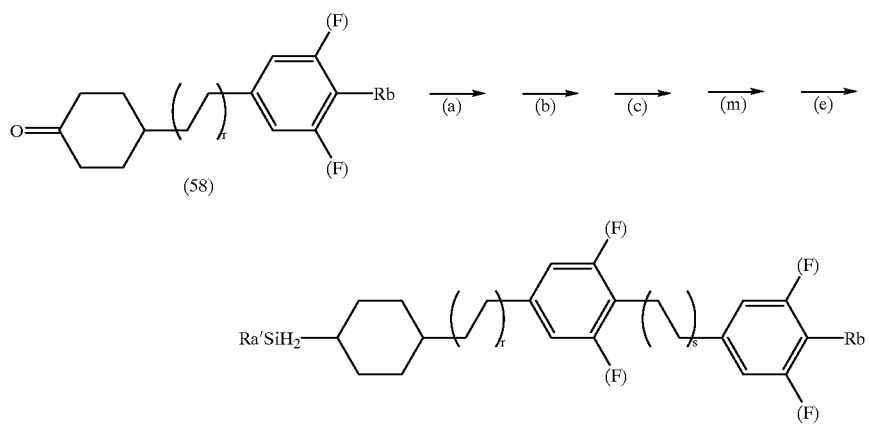
(Scheme 5)
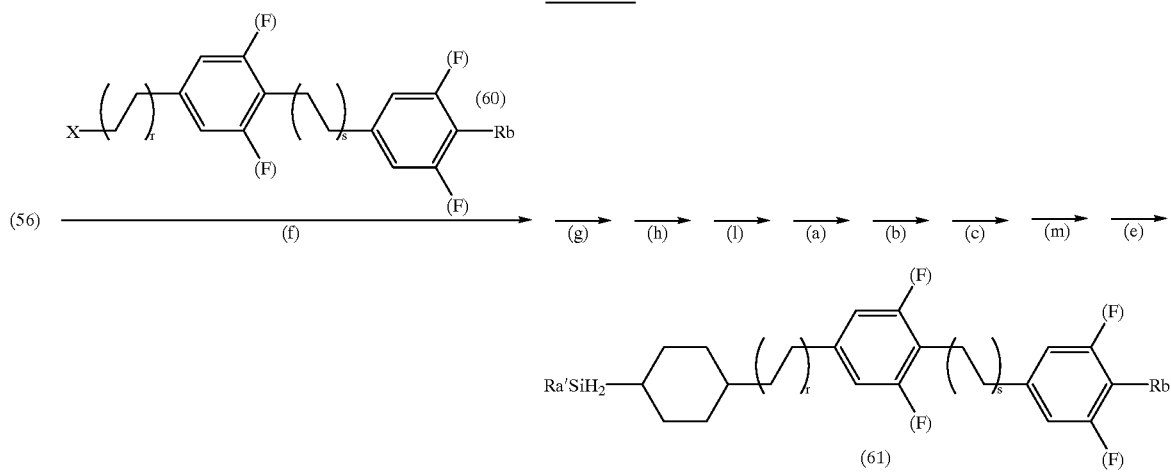
(Scheme 6)
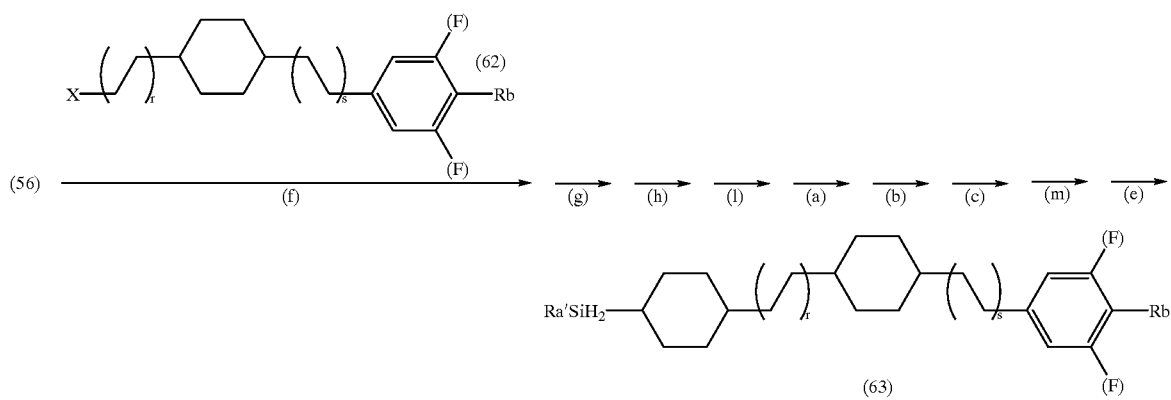

(Scheme 7)

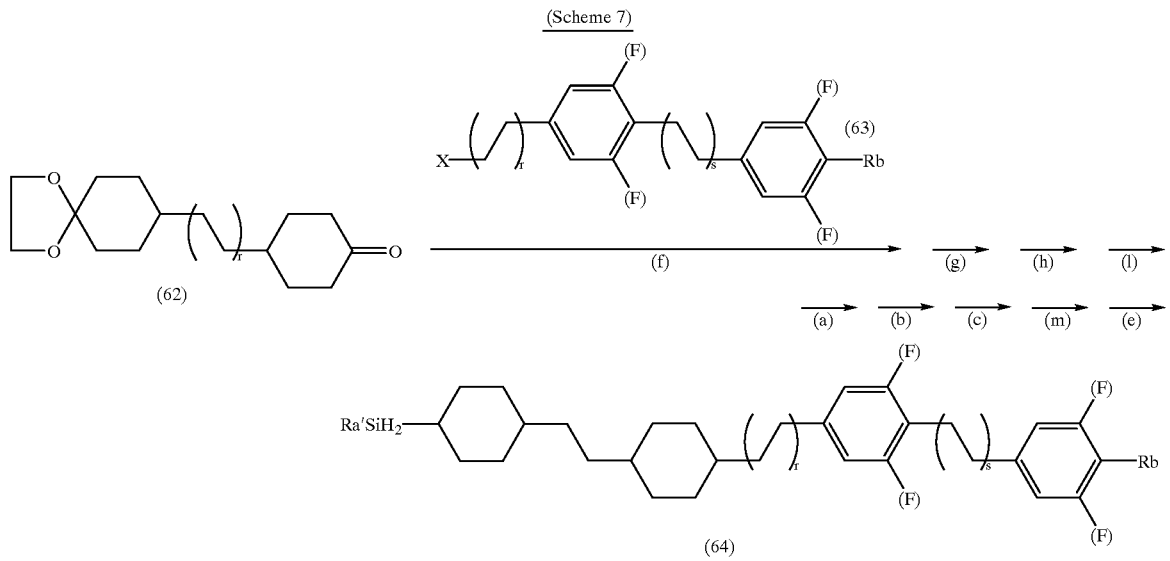

Reaction conditions:

(a) LAH
(b) Ph₃PBr₂
(c) Li/ultrasonic wave
(d) Rb'Si(X)₃
(e) SBH
(f) Halide/n-BuLi
(g) —— H₂O
(h) H₂ Pd C
(i) Br₂ SbCl₅
(j) n-BuLi
(k) Halide n-BuLi/ZnCl₂
(l) H⁺
(m) Ra'Si(X)₃ wherein Ra, Rb, Ra', Rb', and X have the same meaning as that described above, and $q$, $r$, and $s$ are independently an integer of 0 to 2

First, as shown in scheme 1, cyclohexanone derivative (42) is reduced with a reducing agent such as LAH, SBH, diisobutylaluminum hydride and sodium bis(2-methoxyethoxy)aluminum hydride to convert it into compound (43), and then converted into halide (44) by the method of G. A. Wiley et al. described above. The compound (44) is converted into lithium reagent (45) by a method of C. Petrier et al. (The Journal of Organic Chemistry, 50, 5761 (1985)), and then reacted with an alkyltrihalogenated silane to convert it into compound (46). The compound (46) can be reduced with a reducing agent such as SBH and LAH to obtain objective compound (47) as an example.

Next, as shown in scheme 2, the cyclohexanone derivative (42) described above is converted into compound (48) by a method of J. D. Buhler et al. (The Journal of Organic Chemistry, 38, 904 (1973)), and then heated to dehydrate in a solvent such as toluene and xylene in the presence of an acid catalyst such as p-toluenesulfonic acid to convert it into compound (49). The compound (49) is subjected to a catalytic hydrogenation in the presence of a catalyst such as Pd—C to converted it into compound (50), and then converted into halide (51) by the method of Uemura et al. described above. The compound (51) can be lithiated with a lithium reagent such as n-BuLi and tert-BuLi, and then subjected to a reaction with an alkyltrihalogenated silane and to a reduction to obtain objective compound (52) as an example.

As shown in scheme 3, halide (53) is converted into cyclohexanone derivative (54) by conducting a method of Hayashi et al. (Journal of the American Chemical Society, 106, 158 (1984)) and a deprotection. Reaction procedures (a) to (e) can be conducted in the same manner as in scheme 1 with the exception that the cyclohexanone derivative (54) is used in place of the cyclohexanone derivative (42) to obtain objective compound (55) as an example.

As shown in scheme 4, cyclohexanone derivative (56) is converted into cyclohexanone derivative (58) by conducting the method (f) of J. D. Buhler et al. in the same manner as in scheme 2, subjecting to a dehydration (g) and a catalytic hydrogenation (h), and then subjecting to a deprotection (l). The cyclohexanone derivative (58) can be subjected to reaction procedures (a) to (e) in the same manner as in scheme 1 with the exception that the cyclohexanone derivative (58) is used in place of the cyclohexanone derivative (42) and that procedure (m) is conducted instead of (d), to obtain objective compound (59) as an example.

As shown in scheme 5, objective compound (61) as an example can be obtained in the same manner as in scheme 4 with the exception that halide (60) is used in place of halide (57) used in procedure (f).

As shown in scheme 6, objective compound (63) as an example can be obtained in the same manner as in scheme 4 with the exception that halide (62) is used in place of halide (57) used in procedure (f).

Further, as shown in scheme 7, objective compound (64) as an example can be obtained by conducting the same procedures as in scheme 4 with the exception that cyclohexanone derivative (62) and halide (63) are used in place of cyclohexanone derivative (56) and halide (57), respectively.

Organosilicon compounds of the present invention thus obtained are excellent in miscibility with other liquid crystal materials and have a low viscosity compared with known compounds of a similar structure having a trialkylsilyl group. The organosilicon compounds have such unexpected good effects that the compounds have a low threshold voltage, and further, exhibit a comparatively low viscosity compared with the compounds of a similar structure having no silanediyl group. These organosilicon compounds of the present invention are sufficiently stable chemically and physically under conditions in which liquid crystal display devices are usually employed, and thus, are considerably excellent as constituent of nematic liquid crystal compositions.

Compounds of the present invention can preferably be used as constituent in the liquid crystal compositions even for TN mode, STN mode, or TFT mode.

Compounds of the present invention having two or three rings exhibit a low viscosity, and the compounds having three or four rings exhibit a high phase transition temperature to an isotropic phase.

Compounds having two or more cyclohexane rings in the molecule exhibit a high phase transition temperature to an isotropic phase, a low Δn, and a low viscosity, and the compounds having two or more aromatic rings exhibit a high Δn. Further, the compounds having a dioxane ring or pyrimidine ring exhibit a comparatively high Δ ε.

Compounds having a double bond in Ra and/or Rb exhibit a high ratio of elastic constants (bend elastic constant/splay elastic constant); and liquid crystal compositions exhibiting a steep change in their transmittance can be prepared when the compounds are used as compound for STN mode. Compounds in which Rb is a halogen atom or CN exhibit a high Δ ε.

It is possible to make Δ ε higher by replacing the hydrogen atom in the ring structure by fluorine atom, and the miscibility can be improved at the same time by the replacement.

Compounds having a double bond in $Z_1$, $Z_2$ and/or $Z_3$ exhibit about the same physical properties as those described above, and thus are preferable as compound for STN mode. Compounds having triple bond exhibit a high Δn, and compounds having difluoromethylenoxy (—CF$_2$O—) or oxydifluoromethylene (—OCF$_2$—) exhibit a comparatively high Δ ε and a low viscosity. Further, compounds having 1,2-difluorovinylene (—CF=CF—) exhibit a remarkably low viscosity.

Based on these facts, novel liquid crystalline compounds having desired physical properties can be obtained by properly selecting rings, substituents and/or bonding groups.

While the liquid crystal compositions provided by the present invention may comprise only a first component comprising at least one liquid crystalline compound expressed by the general formula (1), the compositions preferably comprise, as a second component, at least one compound selected from the group consisting of the compounds expressed by the general formula (2), (3), or (4) (hereinafter referred to as second A component) and/or at least one compound selected from the group consisting of the compounds expressed by the general formula (5), (6), (7), (8), or (9) (hereinafter referred to as second B component), in addition to the first component. More desirably, known compounds may be mixed, as a third component, to the compositions for the purpose of adjusting threshold voltage, temperature range of liquid crystal phase, optical anisotropy, dielectric anisotropy, and viscosity.

Among the second A component, as preferable examples of the compounds expressed by the general formula (2), the compounds of the formulas (2-1) to (2-15); as preferable examples of the compounds expressed by the general formula (3), the compounds of the formulas (3-1) to (3-48); and as preferable examples of the compounds expressed by the general formula (4), the compounds of the formulas (4-1) to (4-55) can be mentioned, respectively.

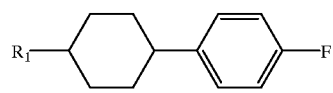
(2-1)

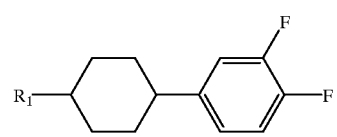
(2-2)

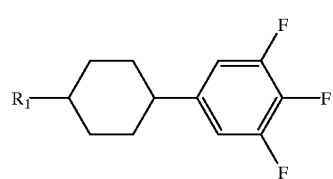
(2-3)

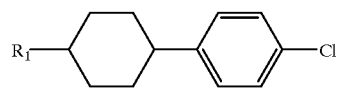
(2-4)

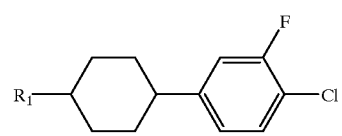
(2-5)

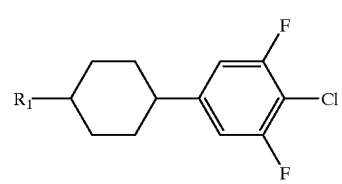
(2-6)

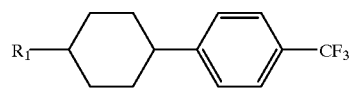
(2-7)

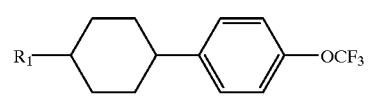
(2-8)

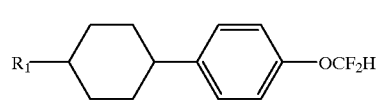
(2-9)

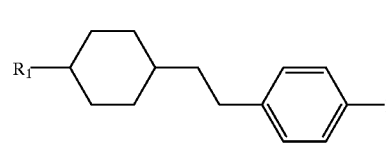
(2-10)

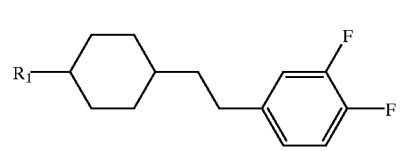
(2-11)

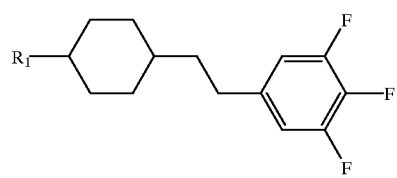 (2-12)
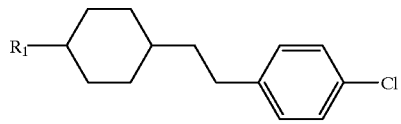 (2-13)
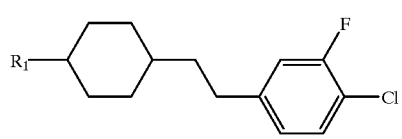 (2-14)
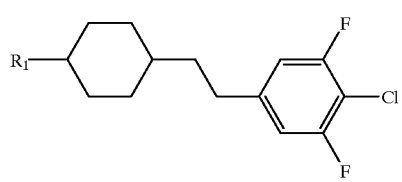 (2-15)
 (3-1)
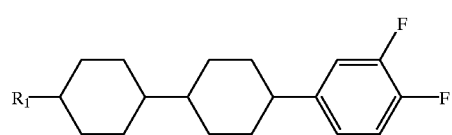 (3-2)
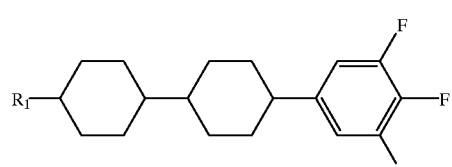 (3-3)
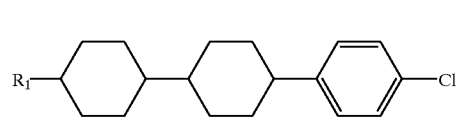 (3-4)
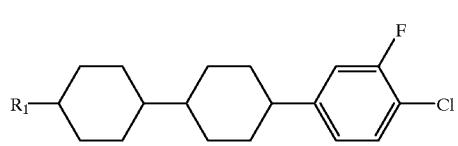 (3-5)
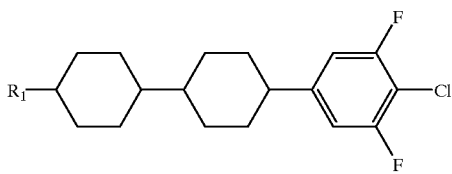 (3-6)
 (3-7)
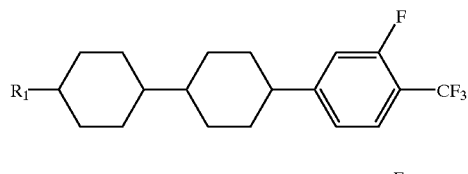 (3-8)
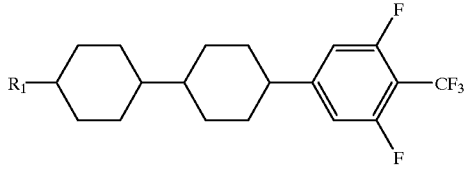 (3-9)
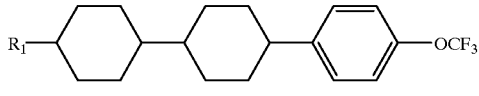 (3-10)
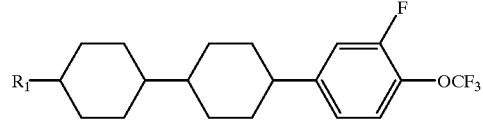 (3-11)
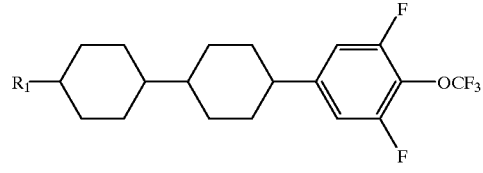 (3-12)
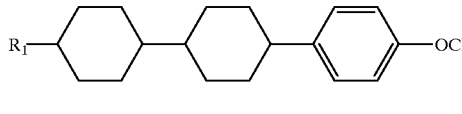 (3-13)
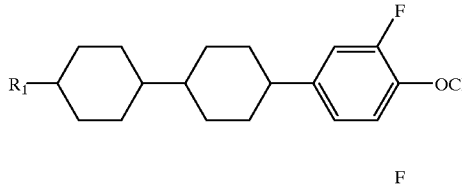 (3-14)
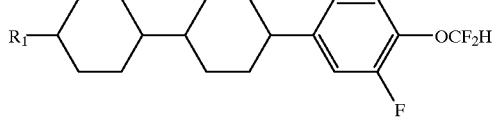 (3-15)

(3-16)
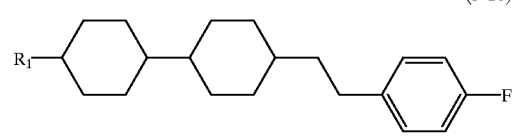
(3-17)
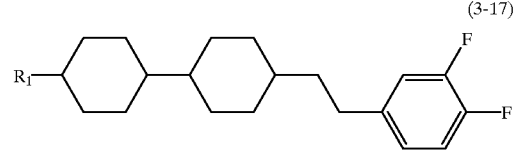
(3-18)
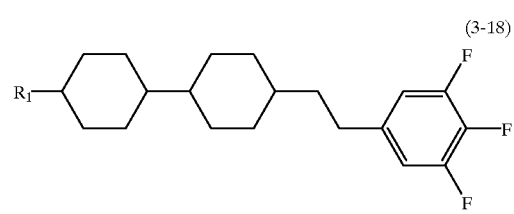
(3-19)
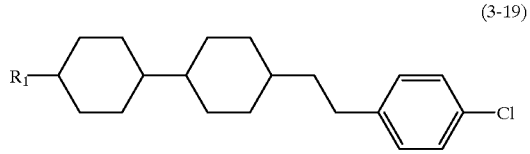
(3-20)
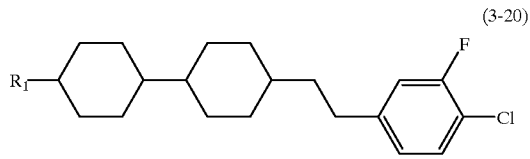
(3-21)
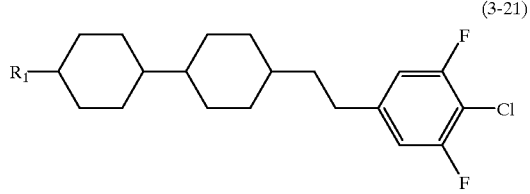
(3-22)
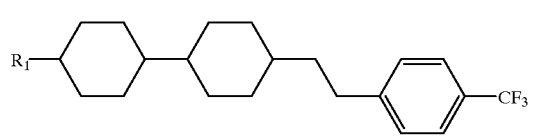
(3-23)
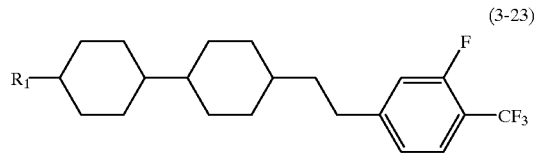
(3-24)
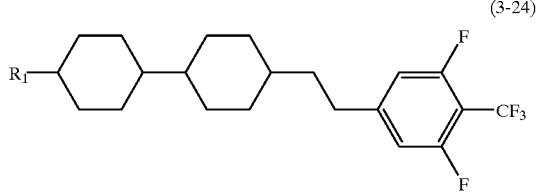
(3-25)
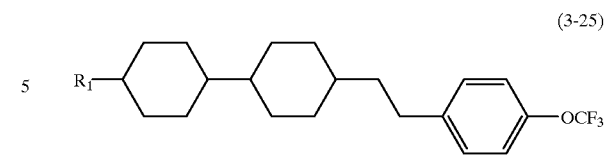
(3-26)
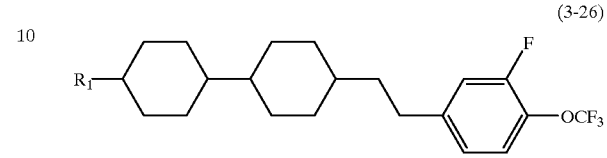
(3-27)
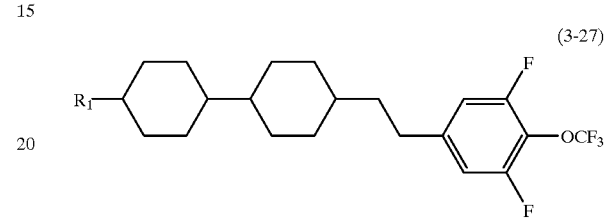
(3-28)
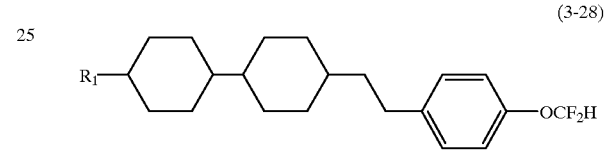
(3-29)
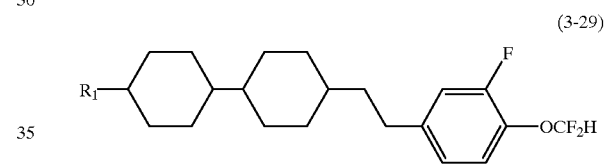
(3-30)
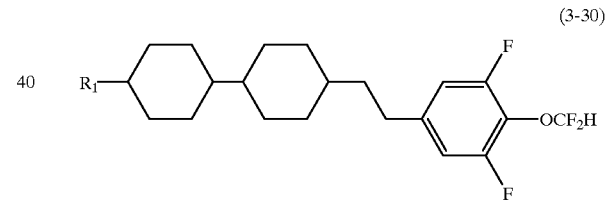
(3-31)
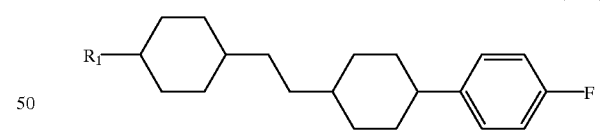
(3-32)
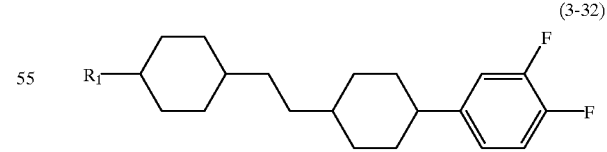
(3-33)
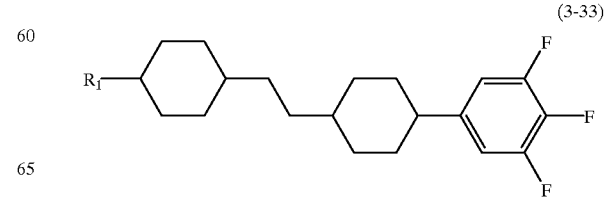

(3-34)
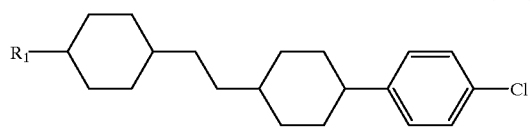
(3-35)
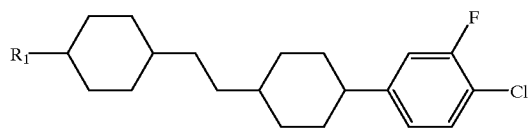
(3-36)
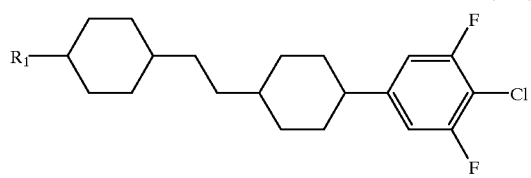
(3-37)
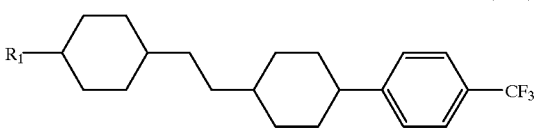
(3-38)
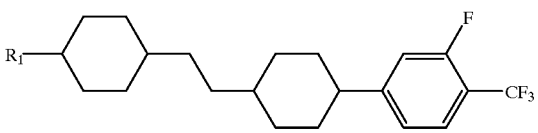
(3-39)
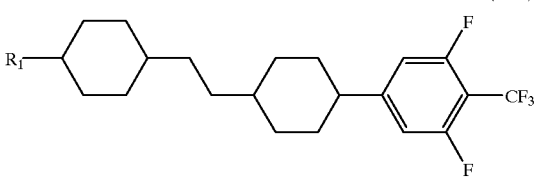
(3-40)
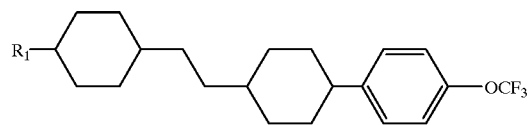
(3-41)
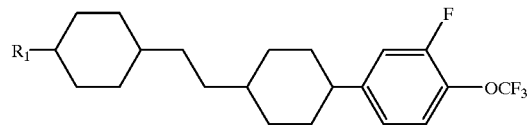
(3-42)
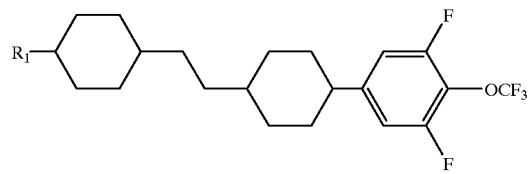
(3-43)
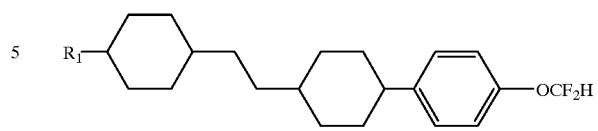
(3-44)
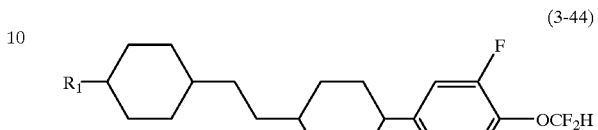
(3-45)
(3-46)
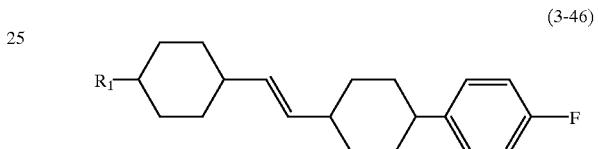
(3-47)
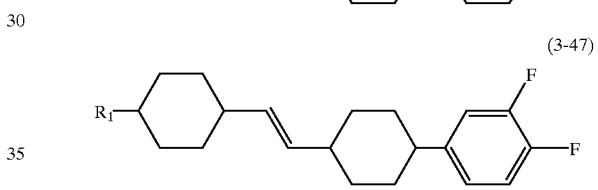
(3-48)
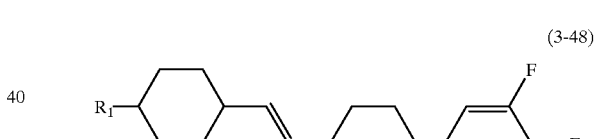
(4-1)
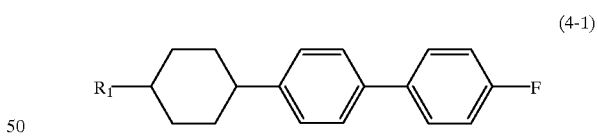
(4-2)
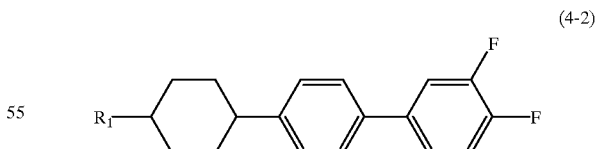
(4-3)
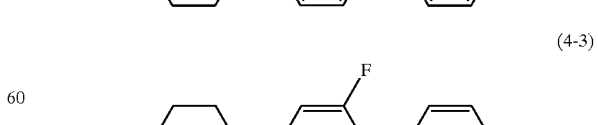

(4-4), (4-5), (4-6), (4-7), (4-8), (4-9), (4-10), (4-11), (4-12), (4-13), (4-14), (4-15), (4-16), (4-17), (4-18), (4-19), (4-20), (4-21)

(4-22) 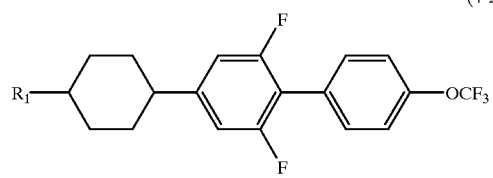
(4-23) 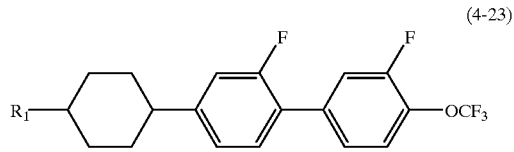
(4-24) 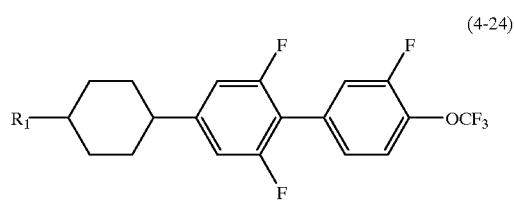
(4-25) 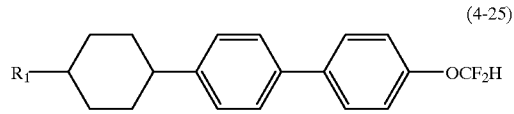
(4-26) 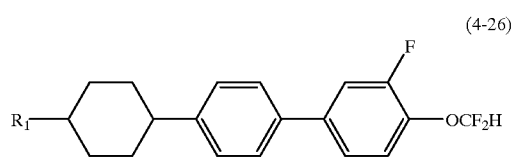
(4-27) 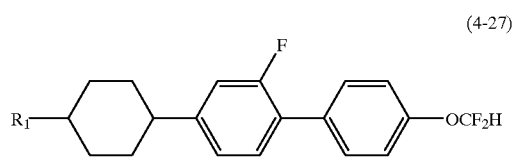
(4-28) 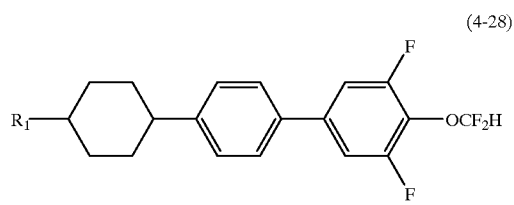
(4-29) 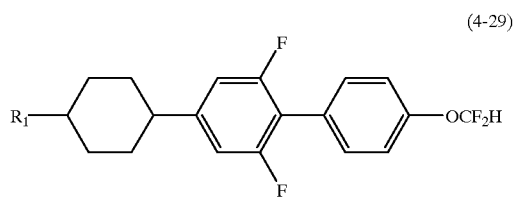
(4-30) 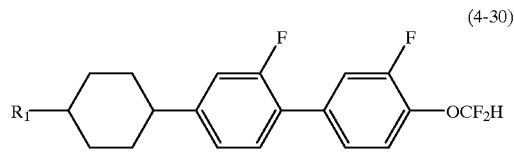
(4-31) 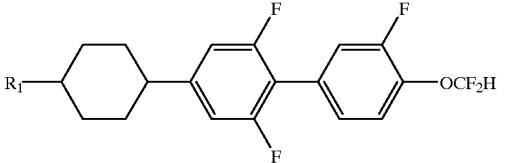
(4-32) 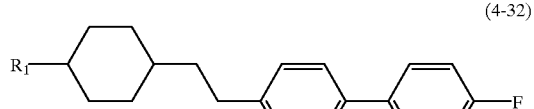
(4-33) 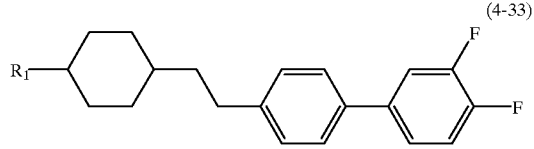
(4-34) 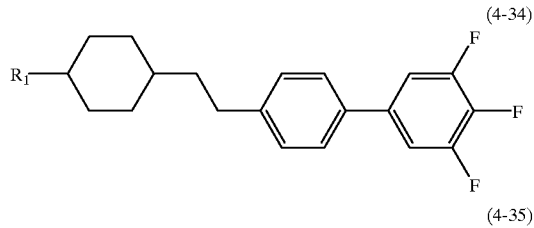
(4-35) 
(4-36) 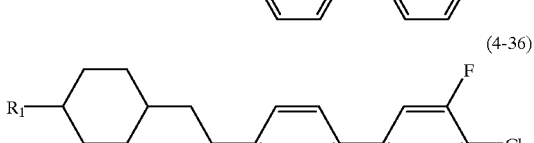
(4-37) 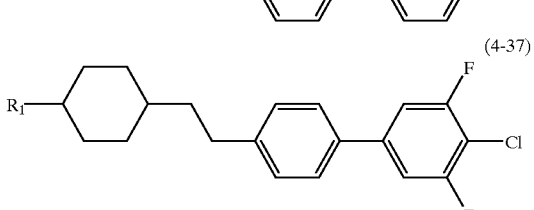
(4-38) 
(4-39) 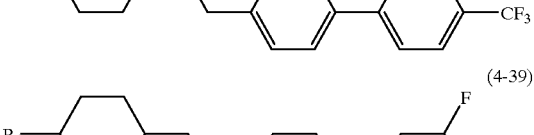
(4-40) 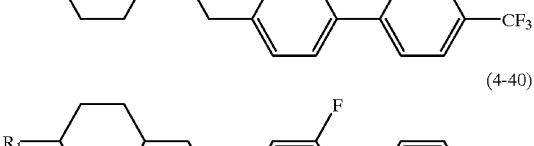

(4-41)
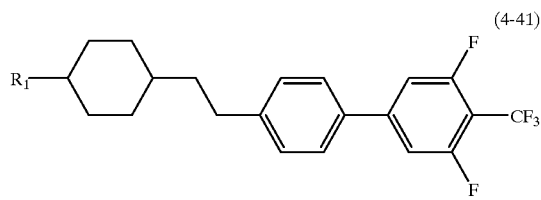

(4-42)
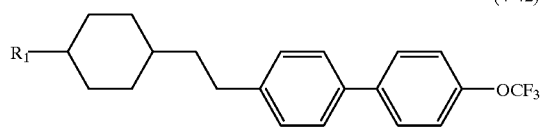

(4-43)
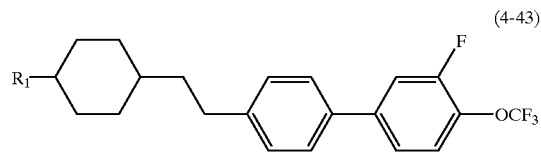

(4-44)
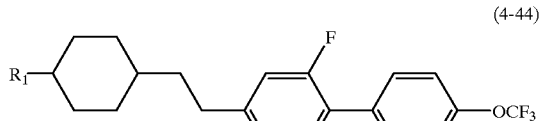

(4-45)
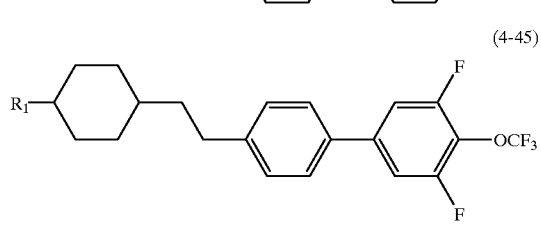

(4-46)
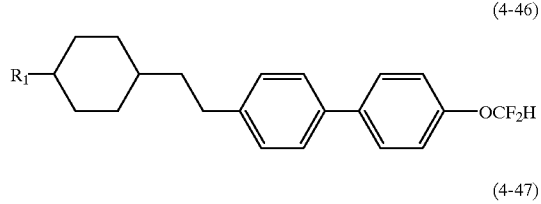

(4-47)
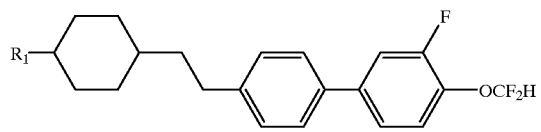

(4-48)
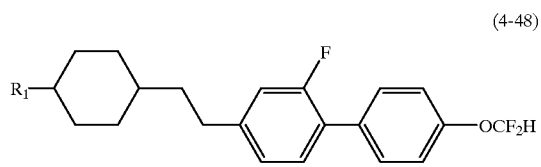

(4-49)
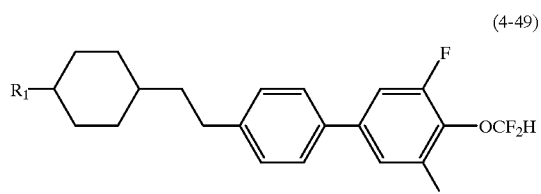

(4-50)
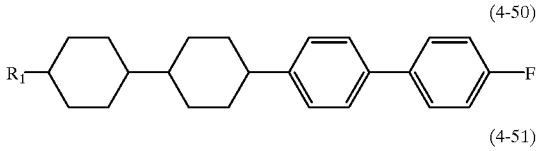

(4-51)
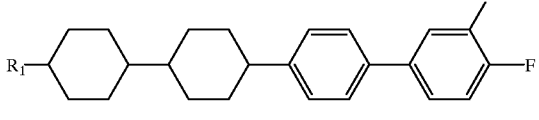

(4-52)
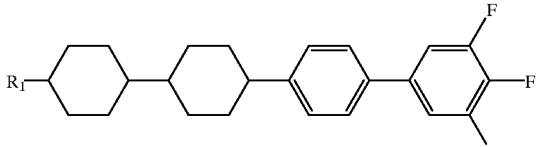

(4-53)
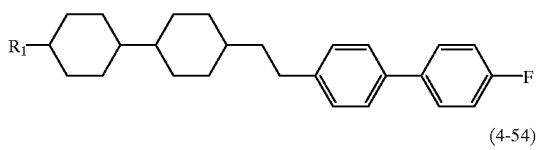

(4-54)
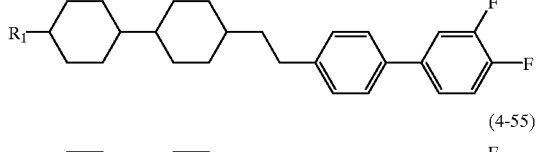

(4-55)
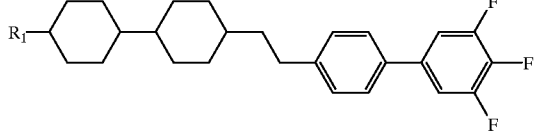

These compounds expressed by one of the general formulas (2) to (4) have a positive value of dielectric anisotropy and are remarkably excellent in heat stability and chemical stability.

Amount of the compounds to be used is suitably in the range of 1 to 99% by weight, preferably 10 to 97% by weight, and more desirably 40 to 95% by weight, based on the total amount of liquid crystal composition.

Next, among the second B component, as preferable examples of the compounds expressed by the general formula (5), (6), or (7), the compounds of the formulas (5-1) to (5-24), (6-1) to (6-3), and (7-1) to (7-17) can be mentioned, respectively.

(5-1)

(5-2)
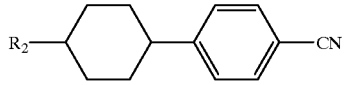

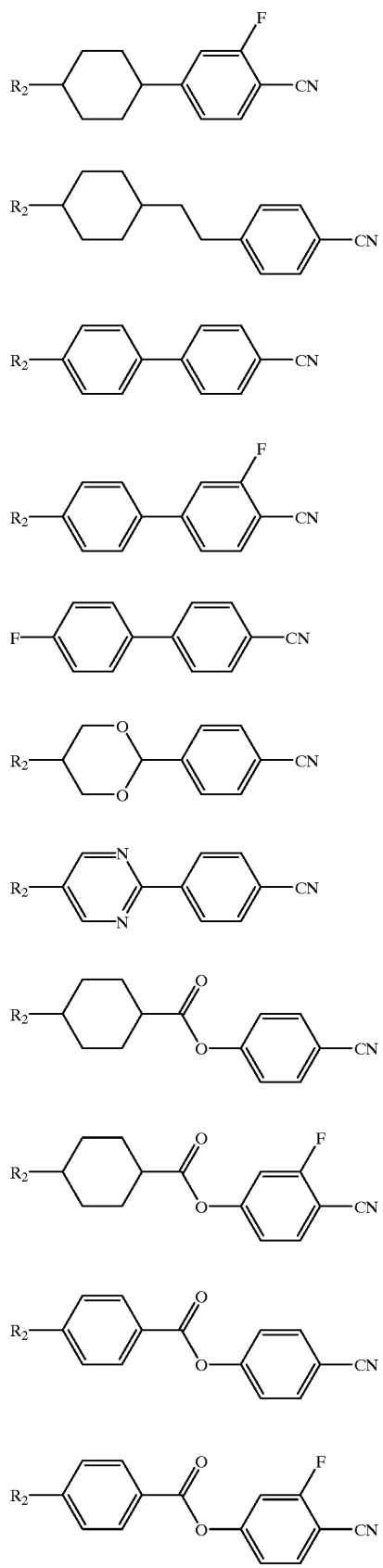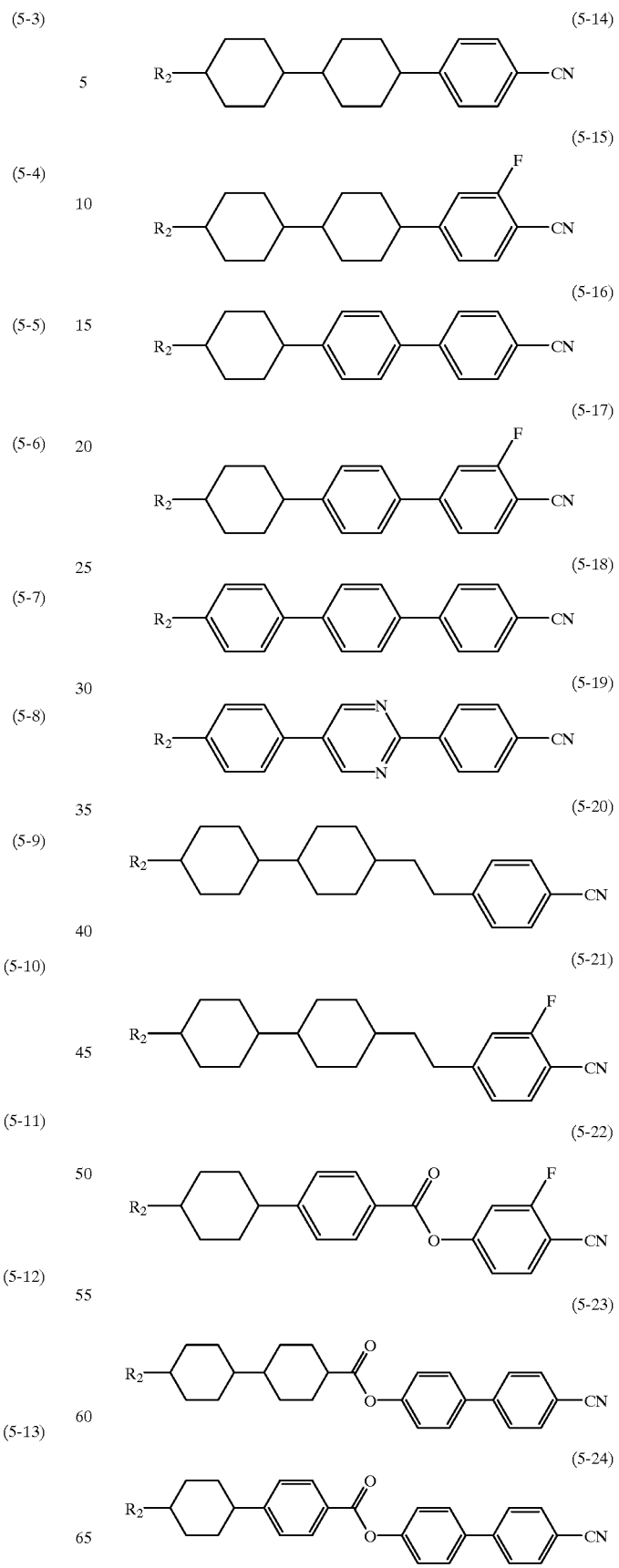

(6-1) 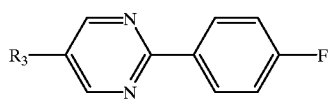
(6-2) 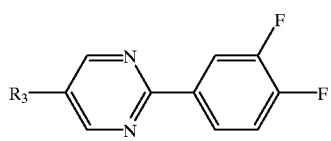
(6-3) 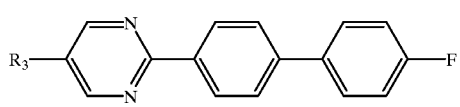
(7-1) 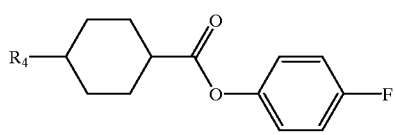
(7-2) 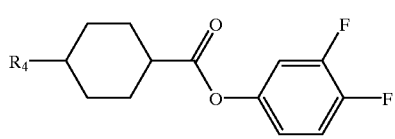
(7-3) 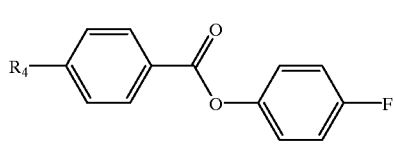
(7-4) 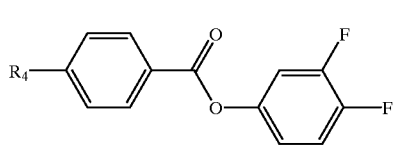
(7-5) 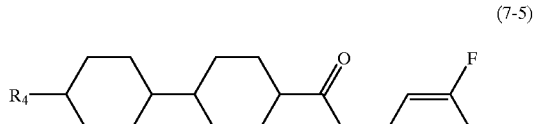
(7-6) 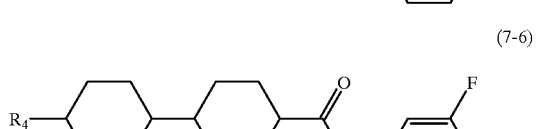
(7-7) 
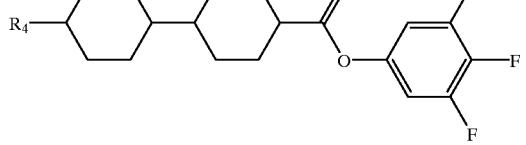
(7-8) 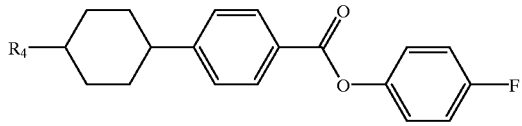
(7-9) 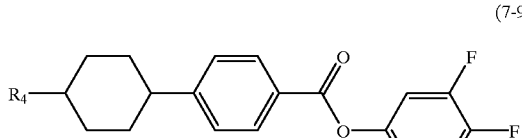
(7-10) 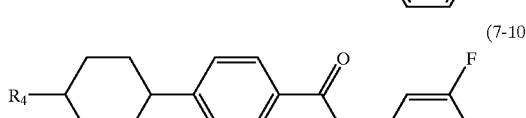
(7-11) 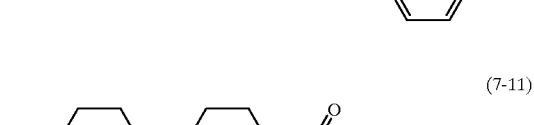
(7-12) 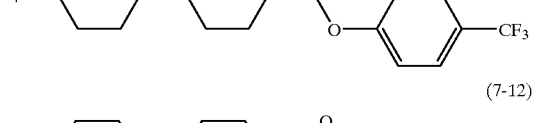
(7-13) 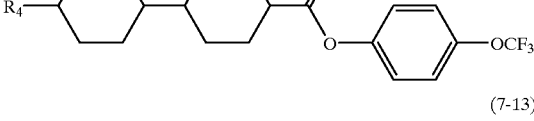
(7-14) 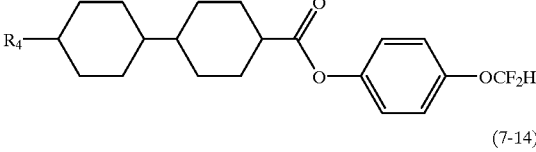
(7-15) 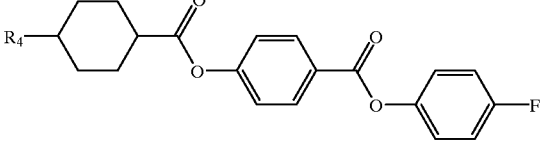
(7-16) 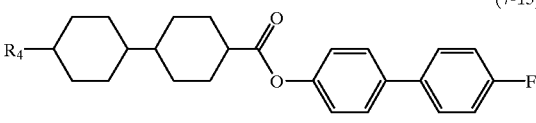
(7-17) 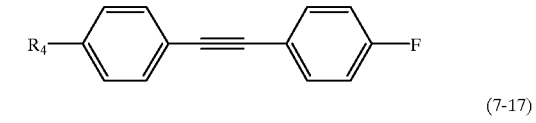
These compounds expressed by one of the general formulas (5) to (7) have a positive large value of dielectric anisotropy, and are used as component of liquid crystal compositions particularly for the purpose of lowering threshold voltage. They are used also for the purpose of adjusting viscosity, adjusting optical anisotropy, and expanding the temperature range of liquid crystal phase, and further, for the purpose of improving the steepness.

Besides, among the second B component, as preferable examples of compounds expressed by the general formula (8) or (9), the compounds of the formulas (8-1) to (8-8) and (9-1) to (9-12) can be mentioned, respectively.

(8-1)
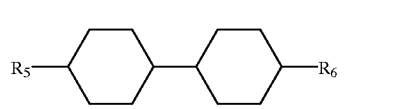

(8-2)
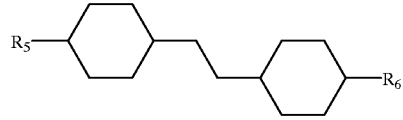

(8-3)
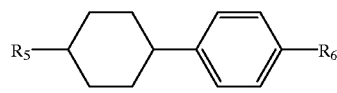

(8-4)
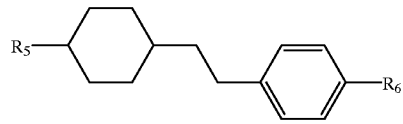

(8-5)
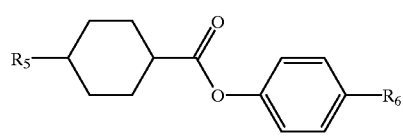

(8-6)
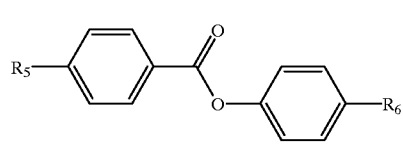

(8-7)
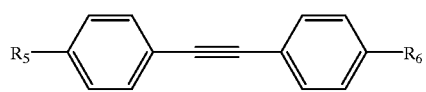

(8-8)
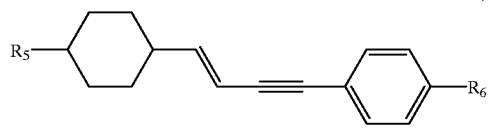

(9-1)
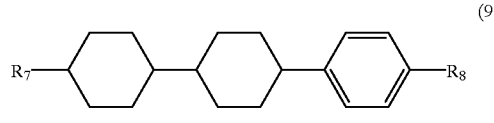

(9-2)

-continued (9-3)
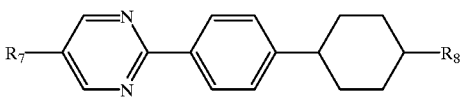

(9-4)
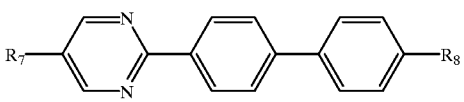

(9-5)
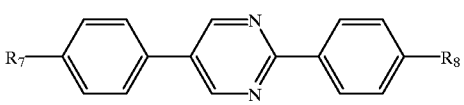

(9-6)
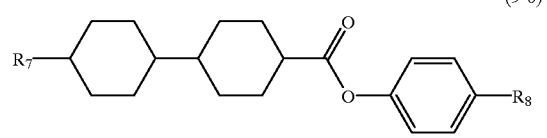

(9-7)

(9-8)
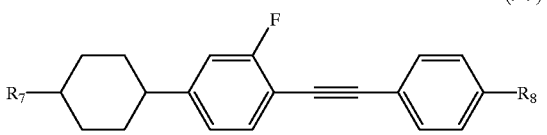

(9-9)
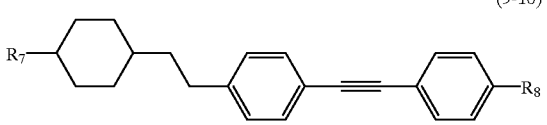

(9-10)
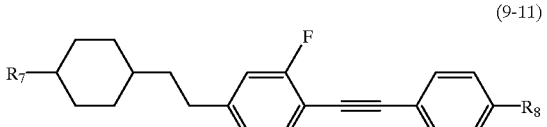

(9-11)
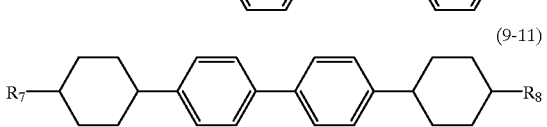

(9-11)
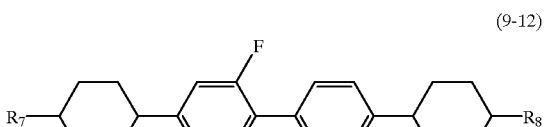

(9-12)
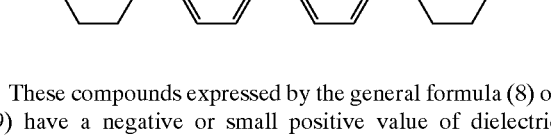

These compounds expressed by the general formula (8) or (9) have a negative or small positive value of dielectric constant. Among them, the compounds expressed by the general formula (8) are used, as component of liquid crystal compositions, principally for the purpose of reducing viscosity and adjusting optical anisotropy. The compounds expressed by the general formula (9) are used for the purpose of expanding the temperature range of liquid crystal phase and/or for the purpose of adjusting optical anisotropy.

Compounds expressed by one of the general formulas (5) to (9) described above are indispensable especially when liquid crystal compositions for displays of STN mode or displays of TN mode are produced. Amount of the compounds to be used is suitably in the range of 1 to 99% by weight, preferably 10 to 97% by weight, and more desirably 40 to 95% by weight, based on the total amount of liquid crystal composition, when liquid crystal compositions for displays of ordinary STN mode or TN mode are produced.

Liquid crystal compositions provided according to the present invention preferably comprise at least one liquid crystalline compound expressed by the general formula (1) in an amount of 0.1 to 99% by weight, to develop excellent characteristics.

The liquid crystal compositions are generally produced by a method which is known to the public by itself, for instance, by a method wherein various components are dissolved in one another at a high temperature. Besides, the compositions are improved and optimized depending on their intended uses by adding a suitable additive when necessary. Such additives are well known in the art and described in detail in the literature. Usually, a chiral dopant or likes which have an effect of inducing a helical structure of liquid crystals to adjust a required twisting angle, and avoiding reverse-twist are added.

Further, the liquid crystal compositions can be used as ones for guest-host (GH) mode when a dichroic dye such as merocyanine type, styryl type, azo type, azomethine type, azoxy type, quinophthalone type, anthraquinone type, or tetrazine type is added. The liquid crystal compositions of the present invention can be used, including for NCAP which is prepared by the microencapsulation of a nematic liquid crystal, and for polymer dispersed liquid crystal display devices (PDLCD) prepared by forming a polymer of three-dimensional reticulated structure in a liquid crystal, for example, polymer net work liquid crystal display devices (PNLCD); for liquid crystal compositions of an electrically controlled birefringence (ECB) mode or dynamic scattering (DS) mode.

As examples of liquid crystal compositions comprising the compound of the present invention, the following can be mentioned. In the following, No. of compounds is the same as that shown in Examples.

Composition Example 1

-continued

| Structure | Amount |
|---|---|
| C₃H₇–[pyrimidine]–[phenyl]–C₂H₅ | 2% by weight |
| C₅H₁₁–[cyclohexyl]–COO–[phenyl]–CH₃ | 4% by weight |
| C₃H₇–[cyclohexyl]–COO–[phenyl]–OC₄H₉ | 4% by weight |
| C₃H₇–[cyclohexyl]–COO–[phenyl]–OC₂H₅ | 4% by weight |
| C₄H₉–[cyclohexyl]–COO–[phenyl]–OC₄H₉ | 4% by weight |
| CH₃O–[phenyl]–COO–[phenyl]–C₂H₅ | 4% by weight |
| C₂H₅–[pyrimidine]–[phenyl]–[cyclohexyl]–C₃H₇ | 6% by weight |

Composition Example 2

| Structure | Amount |
|---|---|
| C₃H₇–[cyclohexyl]–[cyclohexyl]–[phenyl]–SiH₂C₂H₅ (No. 34) | 10% by weight |
| C₂H₅SiH₂C₂H₄–[phenyl]–[phenyl]–CN (No. 81) | 5% by weight |
| C₃H₇–[pyrimidine]–[phenyl]–C₃H₆SiH₂CH₃ (No. 33) | 3% by weight |
| C₃H₇–[cyclohexyl]–[phenyl]–[phenyl]–SiH₂C₂H₅ (No. 39) | 8% by weight |
| C₅H₁₁–[phenyl]–[phenyl]–CN | 5% by weight |
| C₃H₇–[cyclohexyl]–[phenyl]–OC₂H₅ | 7% by weight |
| C₃H₇–[cyclohexyl]–[phenyl]–OC₄H₉ | 10% by weight |
| C₃H₇–[pyrimidine]–[phenyl]–C₅H₁₁ | 4% by weight |

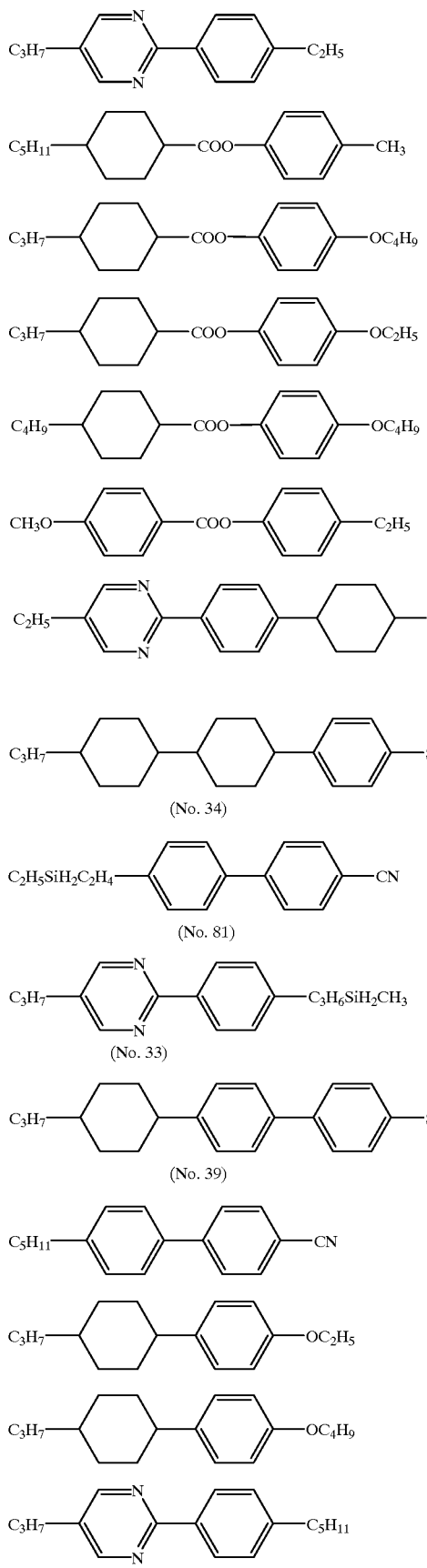
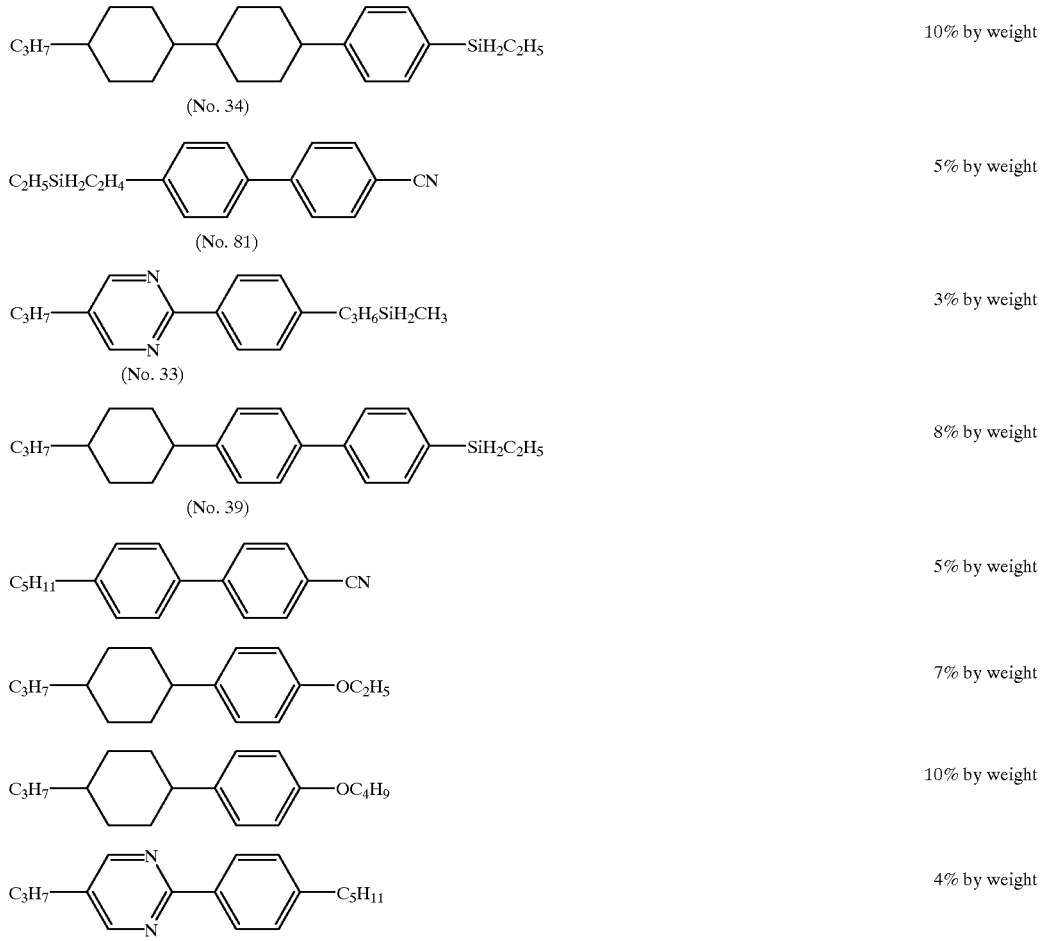

| Structure | Amount |
|---|---|
| C₄H₉–[pyrimidine]–[phenyl]–C₅H₁₁ | 5% by weight |
| C₆H₁₃–[pyrimidine]–[phenyl]–C₅H₁₁ | 7% by weight |
| C₆H₁₃–[pyrimidine]–[phenyl]–OC₅H₁₁ | 8% by weight |
| C₆H₁₃–[pyrimidine]–[phenyl]–OC₆H₁₃ | 8% by weight |
| C₃H₇–[cyclohexyl]–[cyclohexyl]–[phenyl]–CH₃ | 6% by weight |
| C₃H₇–[cyclohexyl]–[cyclohexyl]–[phenyl]–C₃H₇ | 4% by weight |
| C₃H₇–[cyclohexyl]–[cyclohexyl]–[phenyl]–OCH₃ | 3% by weight |
| C₃H₇–[cyclohexyl]–[cyclohexyl]–[phenyl]–F | 4% by weight |
| C₄H₉–[pyrimidine]–[phenyl]–[phenyl]–F | 3% by weight |

Composition Example 3

| Structure | Amount |
|---|---|
| C₂H₅SiH₂–[cyclohexyl]–[cyclohexyl]–[phenyl]–CN (No. 83) | 5% by weight |
| CH₂=C₂H₃SiH₂–[cyclohexyl]–[phenyl]–CN (No. 82) | 5% by weight |
| CH₃SiH₂CH₂–[cyclohexyl]–[phenyl]–CN (No. 114) | 5% by weight |
| C₃H₇–[cyclohexyl]–[cyclohexyl]–C₂H₄SiH₂CH₃ (No. 9) | 5% by weight |
| CH₃O–[phenyl]–C≡C–[phenyl]–SiH₂CH₃ (No. 27) | 5% by weight |
| CH₂=C₃H₅–[cyclohexyl]–[phenyl]–CN | 7% by weight |

-continued
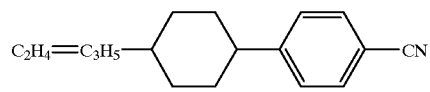 6% by weight
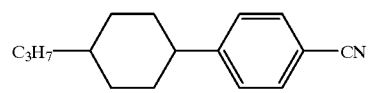 12% by weight
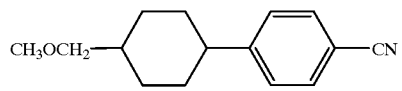 9% by weight
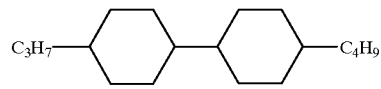 10% by weight
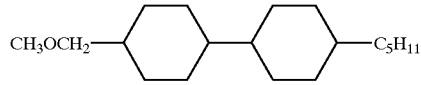 8% by weight
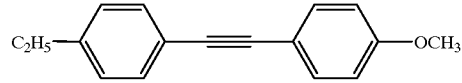 3% by weight
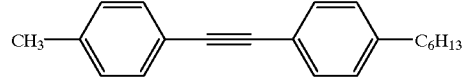 3% by weight
 3% by weight
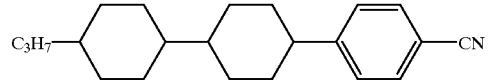 3% by weight
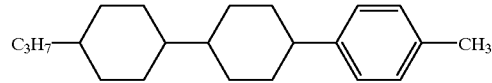 5% by weight
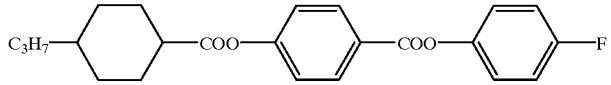 3% by weight
 3% by weight
Composition Example 4
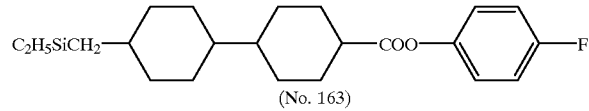
(No. 163)
5% by weight
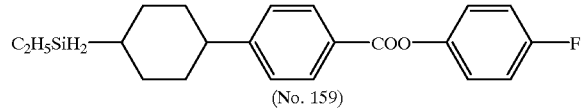
(No. 159)
3% by weight
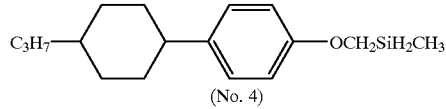
(No. 4)
5% by weight
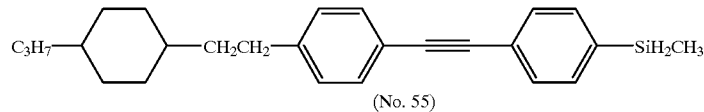
(No. 55)
4% by weight -continued
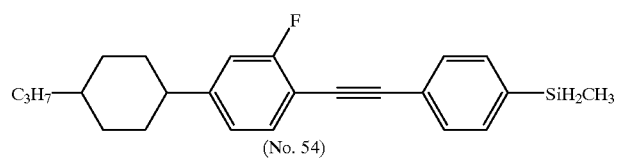
(No. 54)
2% by weight
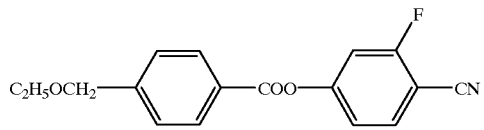
8% by weight
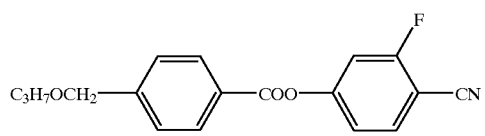
8% by weight
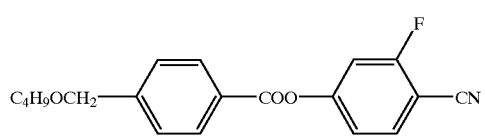
4% by weight
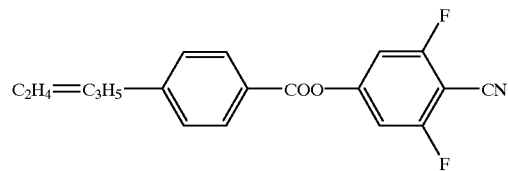
14% by weight
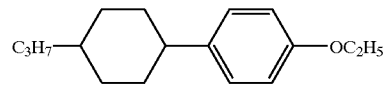
5% by weight
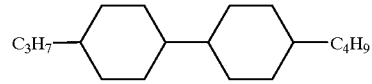
5% by weight
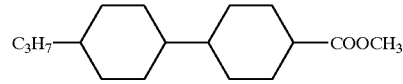
2% by weight
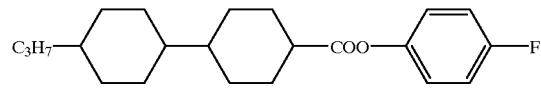
5% by weight
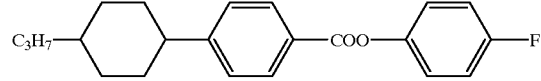
3% by weight
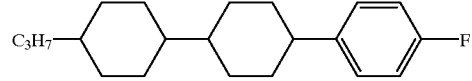
3% by weight
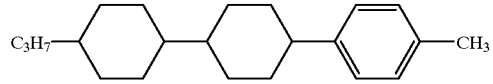
8% by weight
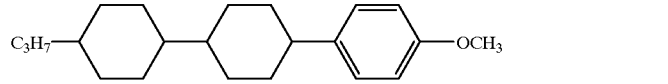
6% by weight
3% by weight -continued
 3% by weight
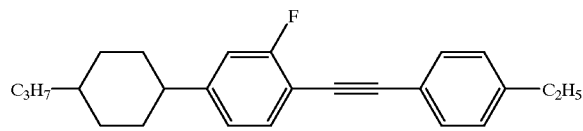 4% by weight
Composition Example 5
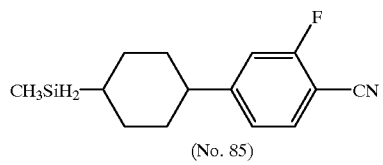 6% by weight
(No. 85)
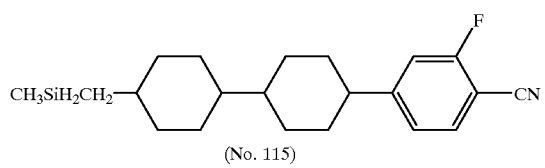 6% by weight
(No. 115)
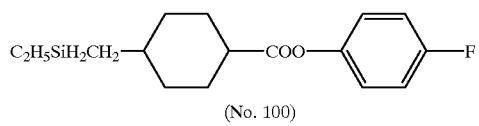 6% by weight
(No. 100)
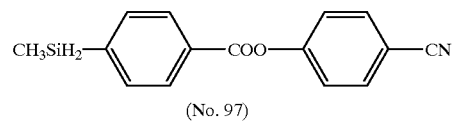 5% by weight
(No. 97)
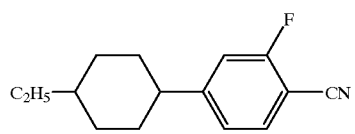 5% by weight
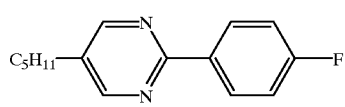 5% by weight
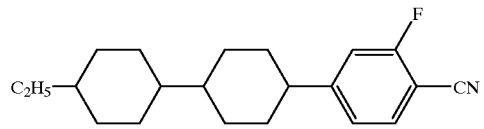 8% by weight
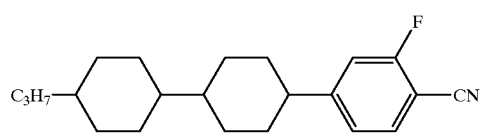 8% by weight
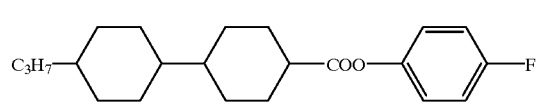 5% by weight
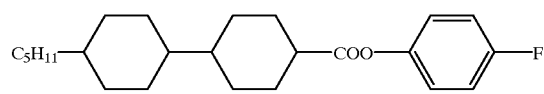 5% by weight
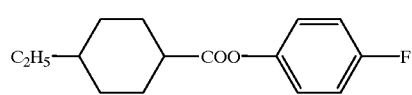 2% by weight

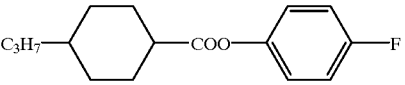 2% by weight
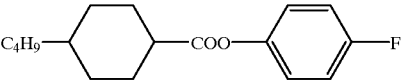 2% by weight
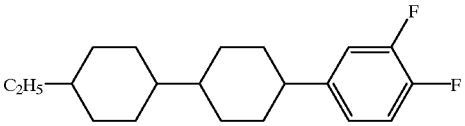 10% by weight
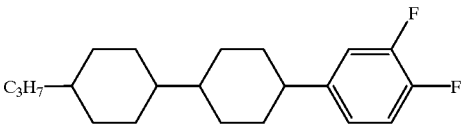 10% by weight
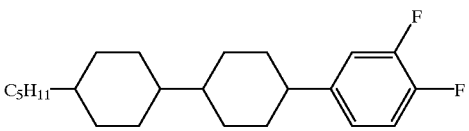 10% by weight
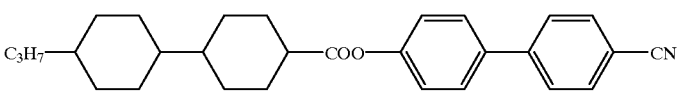 3% by weight
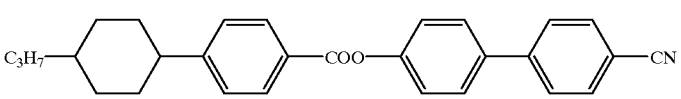 2% by weight
Composition Example 6
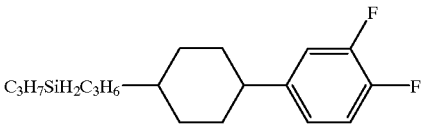 4% by weight
(No. 90)
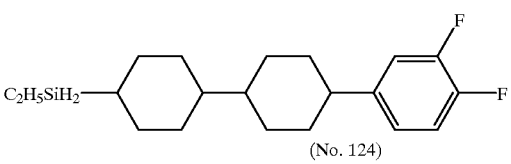 6% by weight
(No. 124)
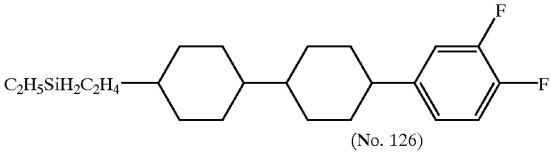 5% by weight
(No. 126)
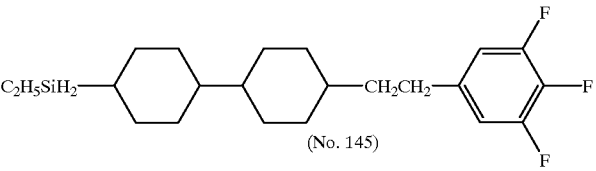 5% by weight
(No. 145)
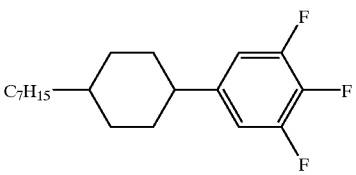 4% by weight -continued
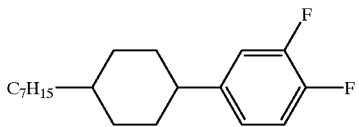 3% by weight
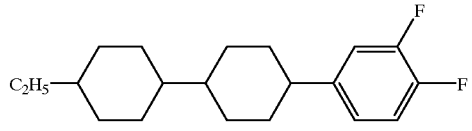 10% by weight
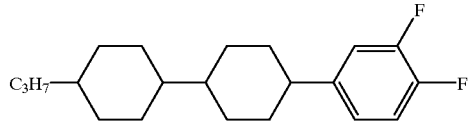 10% by weight
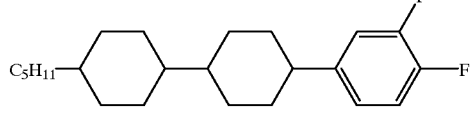 10% by weight
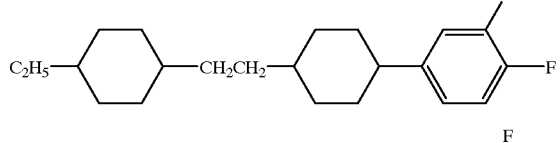 4% by weight
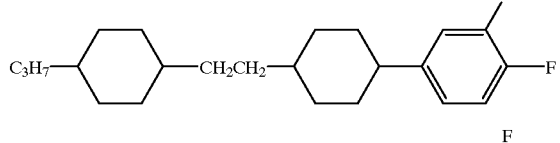 2% by weight
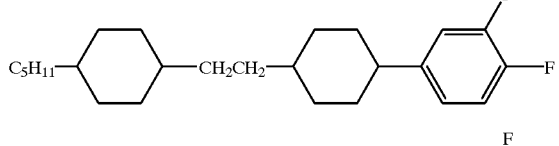 4% by weight
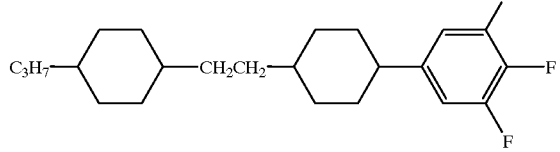 6% by weight
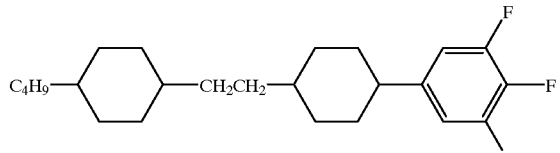 6% by weight
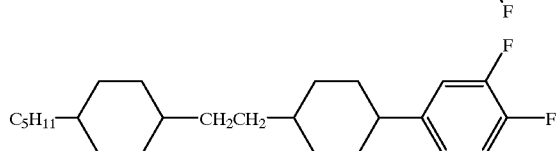 3% by weight
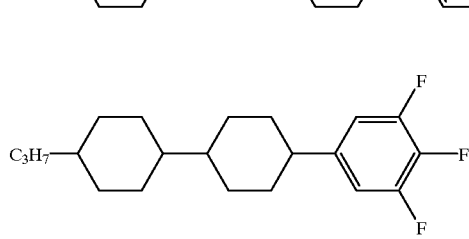 8% by weight

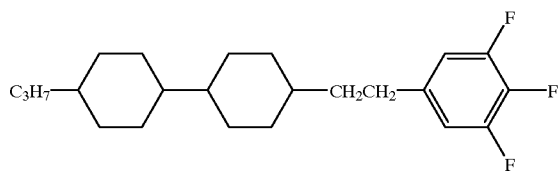
5% by weight
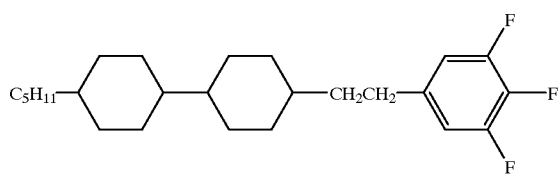
5% by weight
Composition Example 7
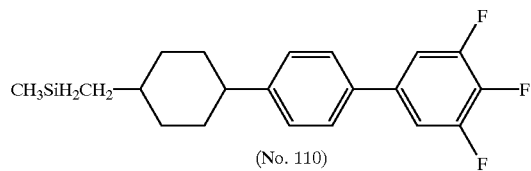
(No. 110)
10% by weight
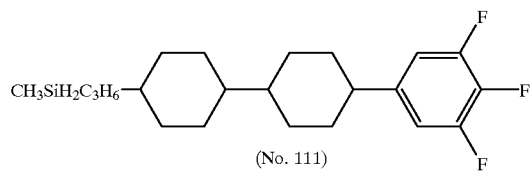
(No. 111)
5% by weight
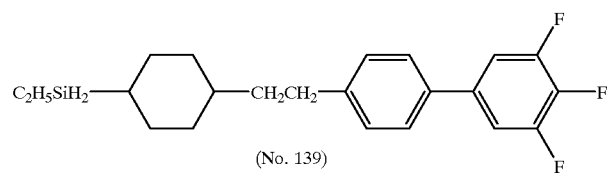
(No. 139)
8% by weight
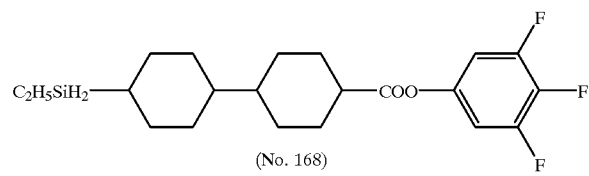
(No. 168)
8% by weight
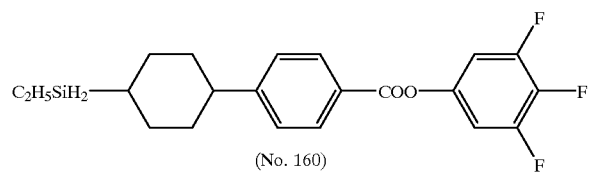
(No. 160)
3% by weight
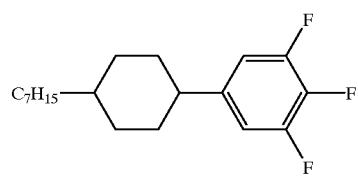
5% by weight
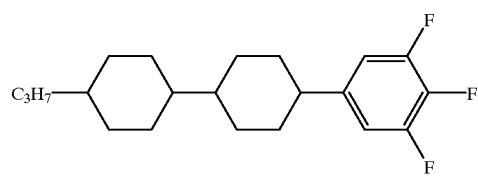
7% by weight

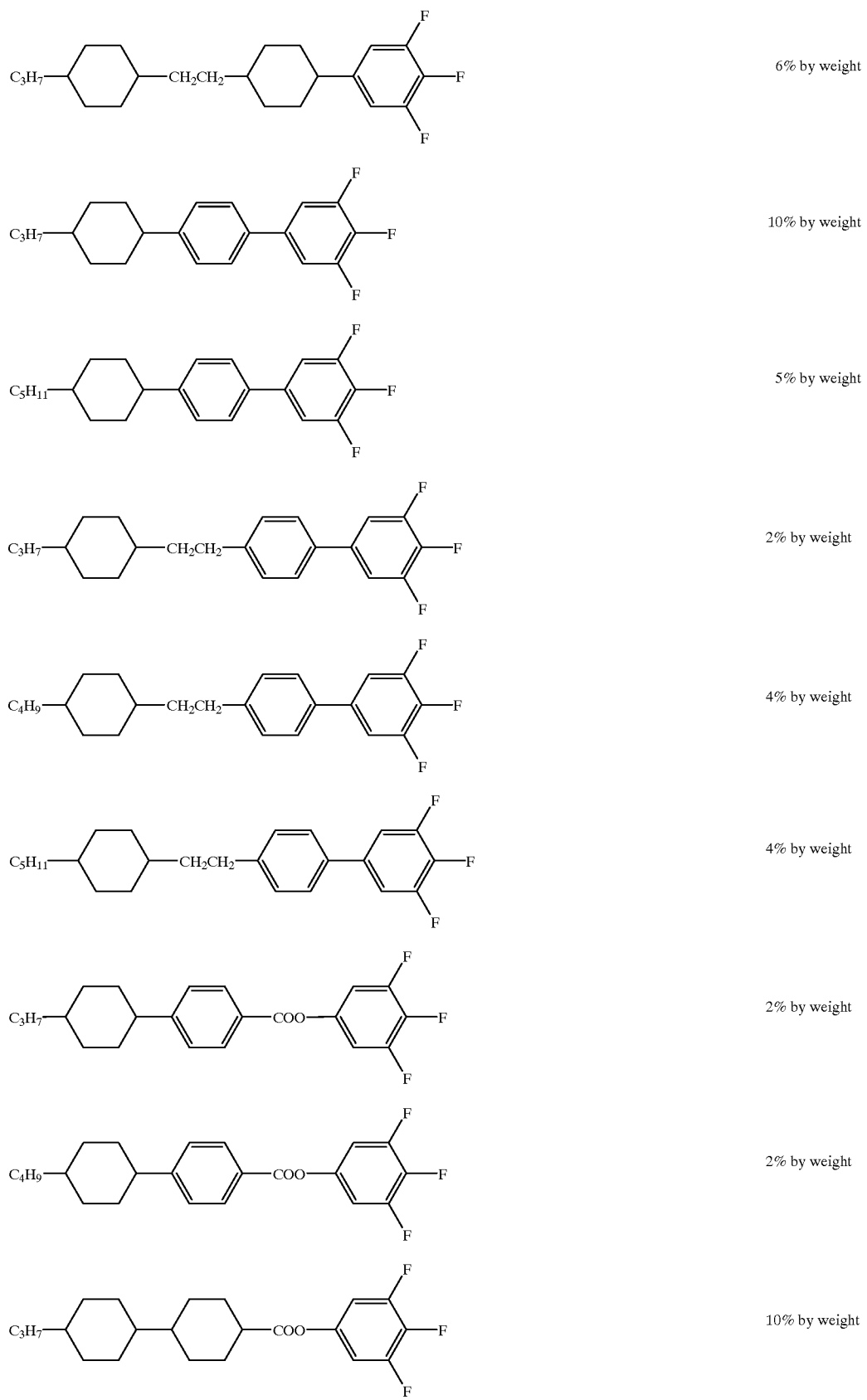
6% by weight
10% by weight
5% by weight
2% by weight
4% by weight
4% by weight
2% by weight
2% by weight
10% by weight

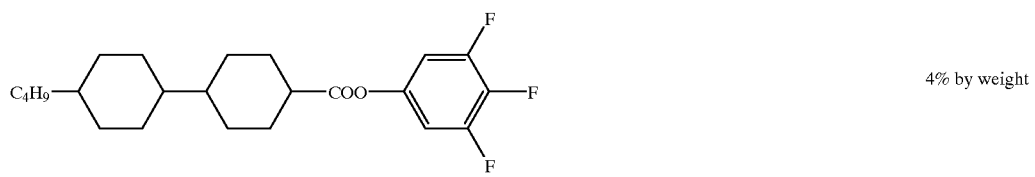
4% by weight
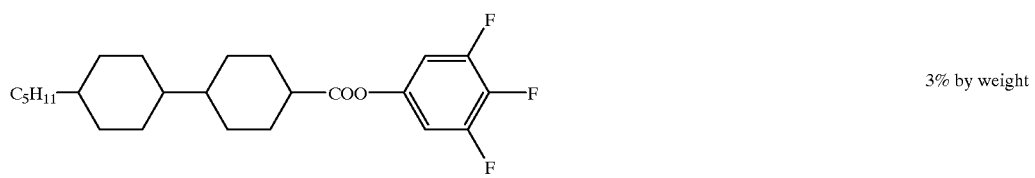
3% by weight
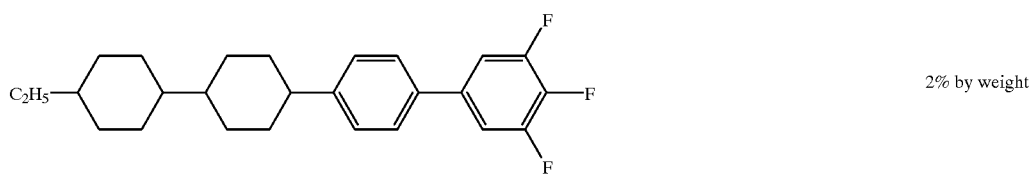
2% by weight
Composition Example 8
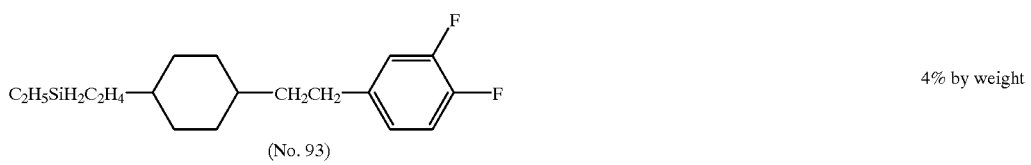
(No. 93)
4% by weight
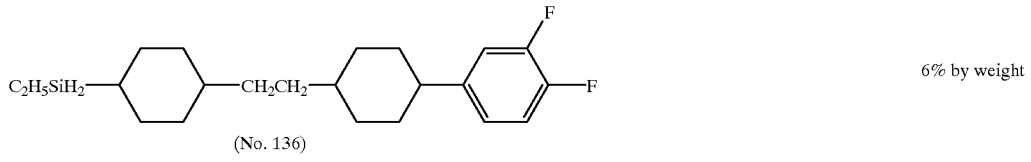
(No. 136)
6% by weight
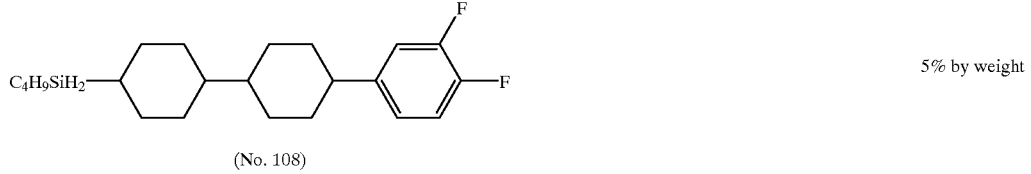
(No. 108)
5% by weight
10% by weight
2% by weight
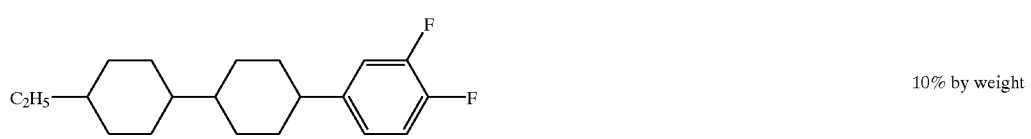
10% by weight
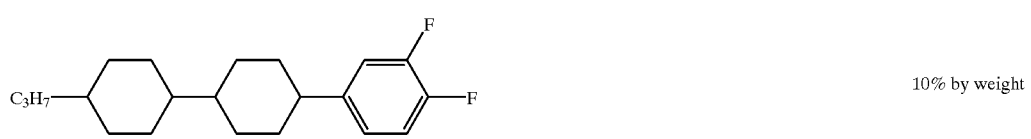
10% by weight -continued
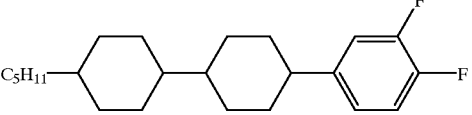 10% by weight
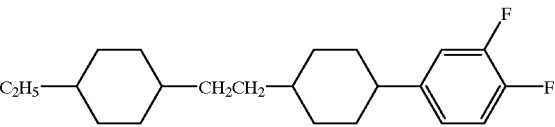 6% by weight
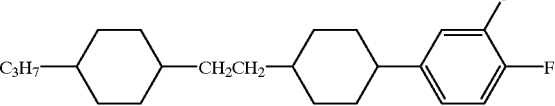 3% by weight
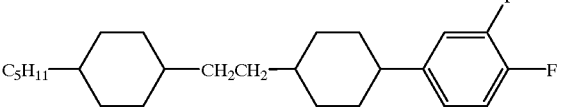 6% by weight
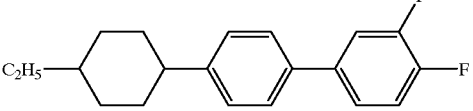 5% by weight
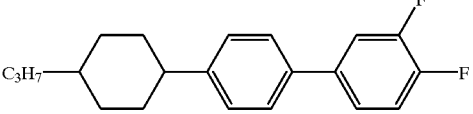 5% by weight
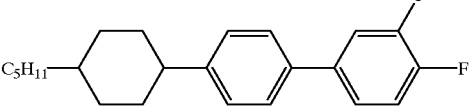 10% by weight
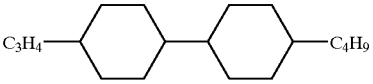 2% by weight
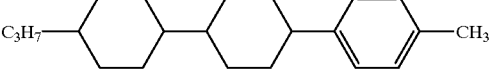 4% by weight
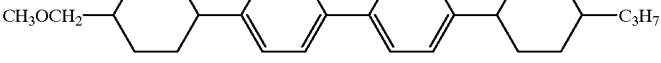 2% by weight
Composition Example 9
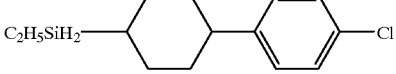 3% by weight
(No. 86)
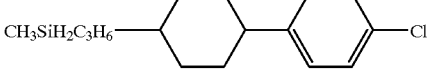 4% by weight
(No. 87)

-continued

CH₃SiH₂—[Cy]—[Cy]—[Ph]—Cl  (No. 117)    5% by weight

C₃H₇SiH₂CH₂—[Cy]—[Cy]—[Ph]—Cl  (No. 118)    5% by weight

C₃H₇SiH₂—[Cy]—[Ph(F)]—C≡C—[Ph]—C₃H₇  (No. 52)    3% by weight

C₃H₇—[Cy]—[Ph]—Cl    3% by weight

C₅H₁₁—[Cy]—[Ph]—Cl    3% by weight

C₇H₁₅—[Cy]—[Ph]—Cl    3% by weight

C₂H₅—[Cy]—[Ph]—[Ph(3,4-F₂)]    7% by weight

C₃H₇—[Cy]—[Ph]—[Ph(3,4-F₂)]    7% by weight

C₅H₁₁—[Cy]—[Ph]—[Ph(3,4-F₂)]    14% by weight

C₂H₅—[Cy]—[Cy]—[Ph]—Cl    4% by weight

C₄H₉—[Cy]—[Cy]—[Ph]—Cl    4% by weight

C₅H₁₁—[Cy]—[Cy]—[Ph]—Cl    4% by weight

C₃H₇—[Cy]—[Ph]—[Ph(3,4,5-F₃)]    15% by weight

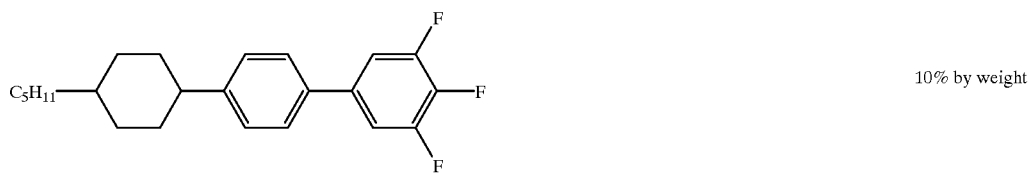
10% by weight
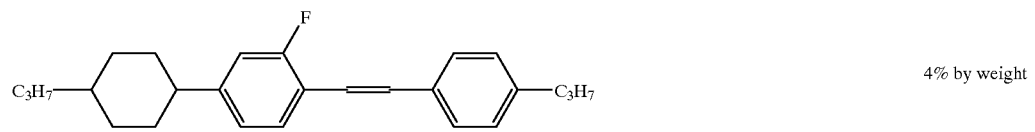
4% by weight
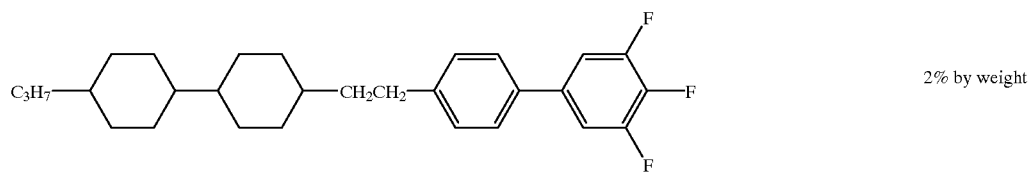
2% by weight
Composition Example 10
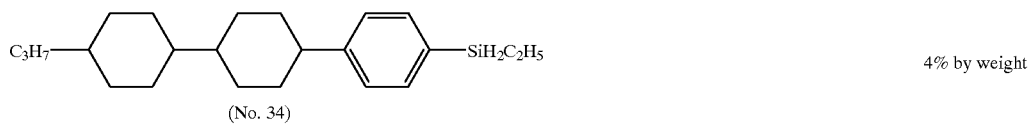
(No. 34)
4% by weight
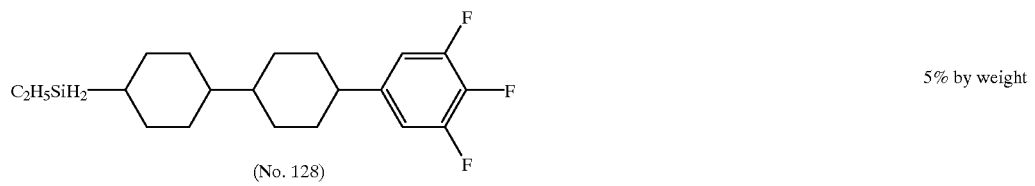
(No. 128)
5% by weight
(No. 91)
3% by weight
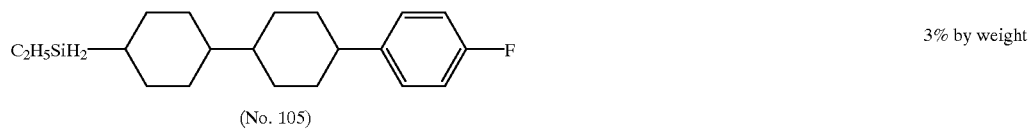
(No. 105)
3% by weight
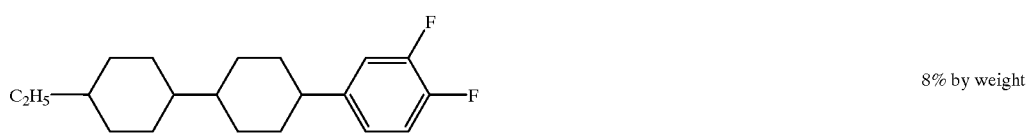
8% by weight
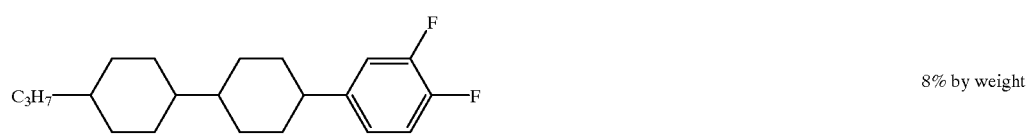
8% by weight
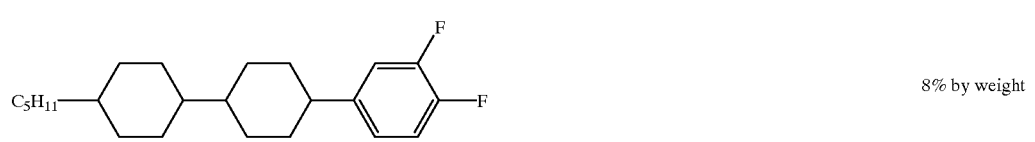
8% by weight -continued
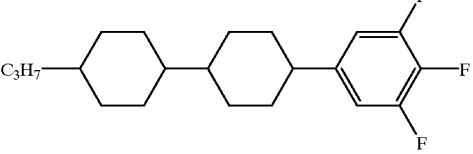 4% by weight
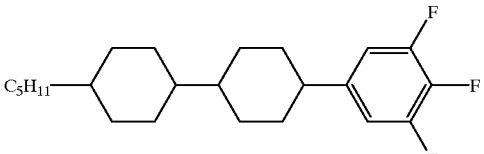 4% by weight
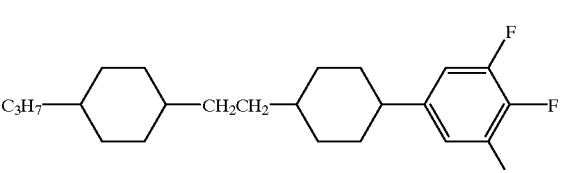 5% by weight
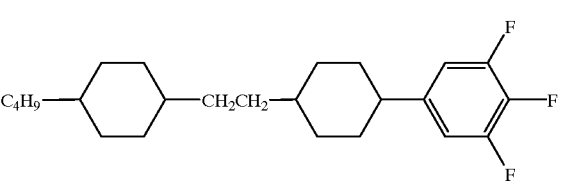 5% by weight
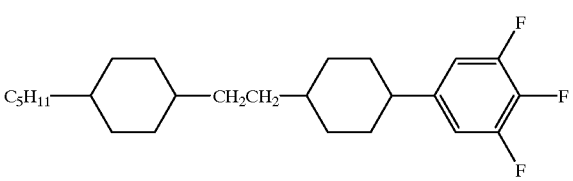 5% by weight
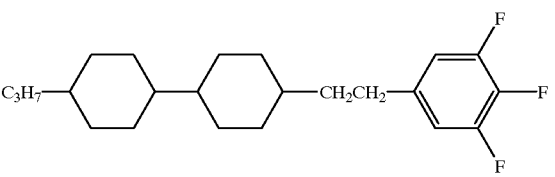 10% by weight
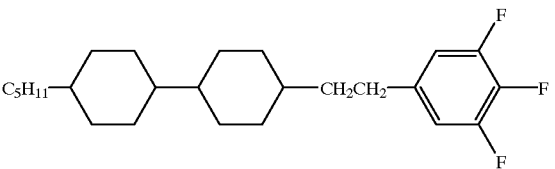 10% by weight
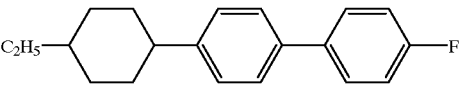 5% by weight
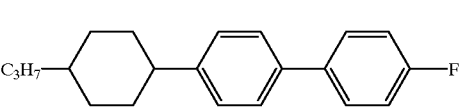 5% by weight
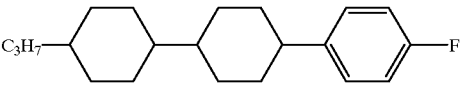 3% by weight
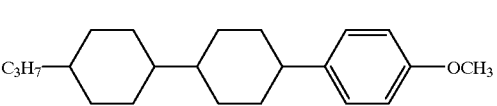 3% by weight -continued
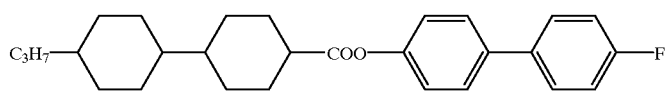 2% by weight
Composition Example 11
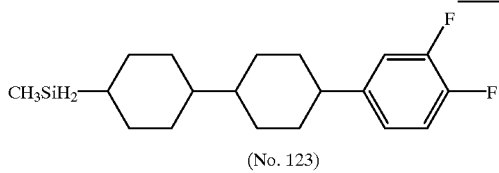 12% by weight
(No. 123)
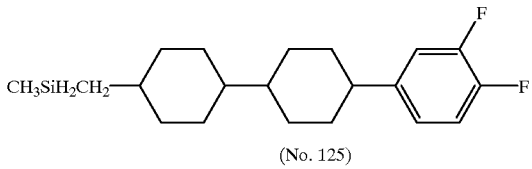 12% by weight
(No. 125)
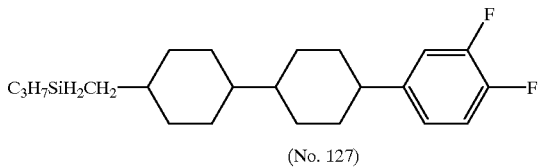 12% by weight
(No. 127)
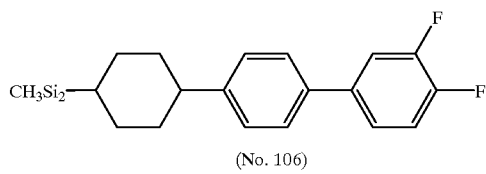 5% by weight
(No. 106)
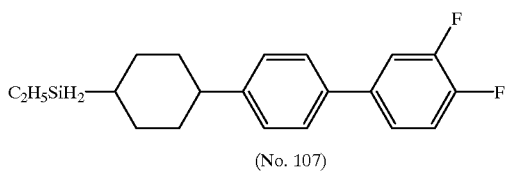 5% by weight
(No. 107)
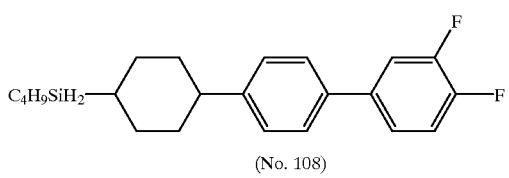 10% by weight
(No. 108)
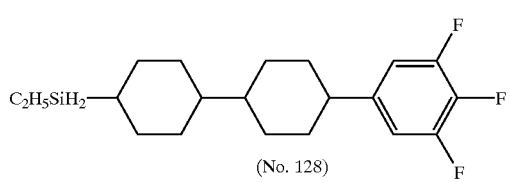 7% by weight
(No. 128)
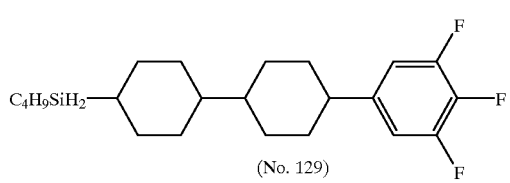 4% by weight
(No. 129)

-continued
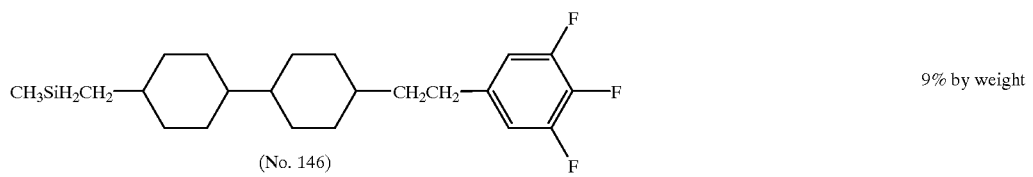
(No. 146)    9% by weight
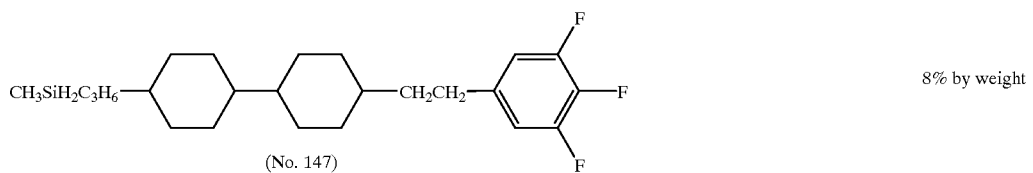
(No. 147)    8% by weight
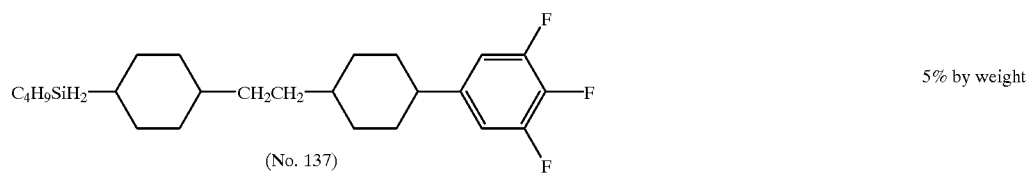
(No. 137)    5% by weight
(No. 3)    5% by weight
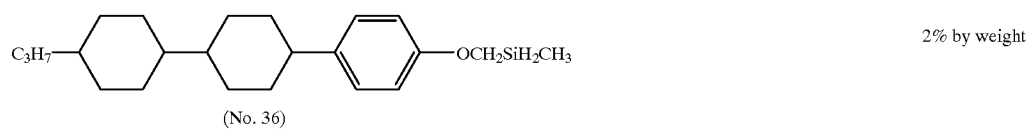
(No. 36)    2% by weight
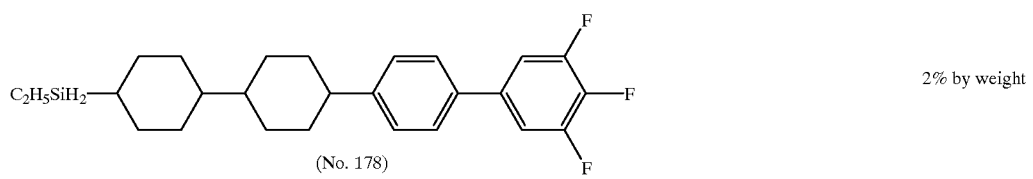
(No. 178)    2% by weight
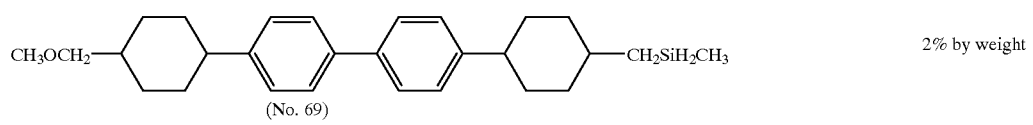
(No. 69)    2% by weight
Composition Example 12
(No. 88)    5% by weight
(No. 89)    5% by weight
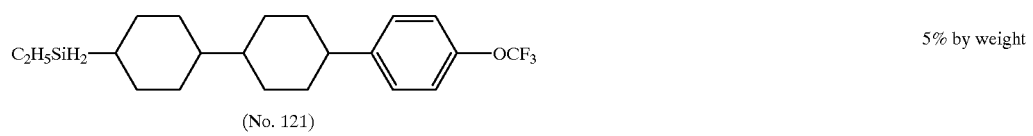
(No. 121)    5% by weight
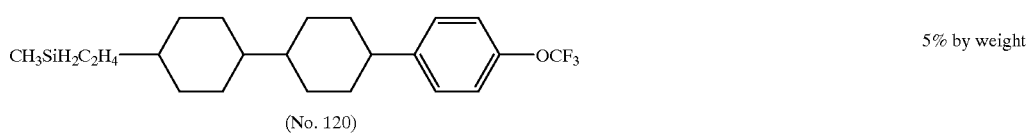
(No. 120)    5% by weight -continued
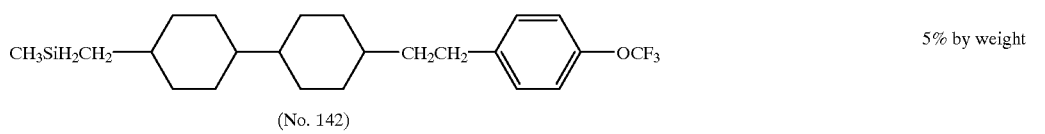
(No. 142) — 5% by weight
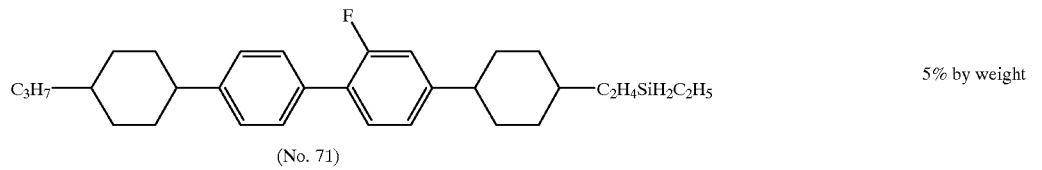
(No. 71) — 5% by weight
 10% by weight
 15% by weight
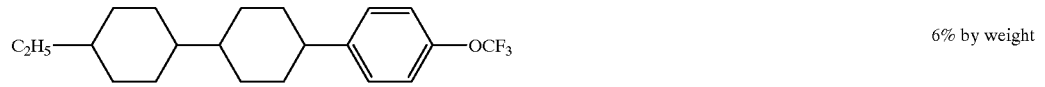 6% by weight
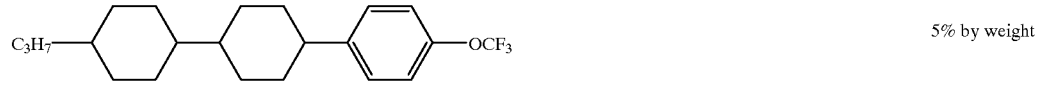 5% by weight
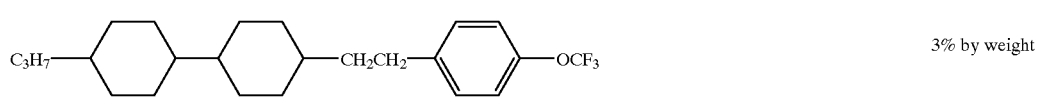 3% by weight
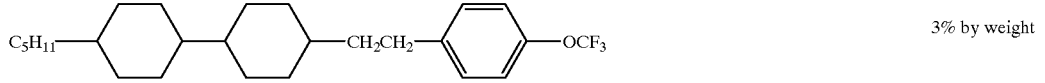 3% by weight
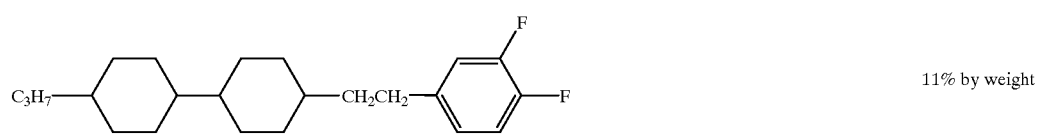 11% by weight
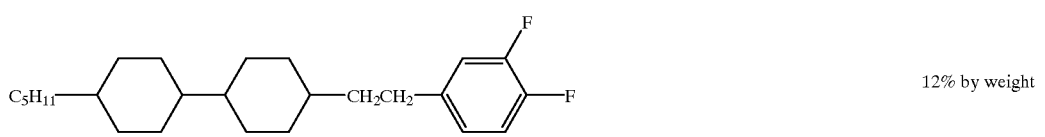 12% by weight
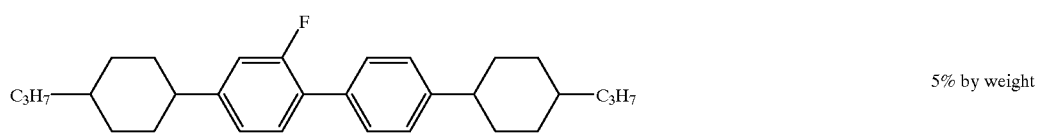 5% by weight
Composition Example 13
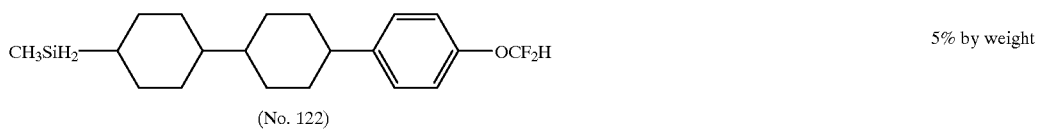
(No. 122) — 5% by weight
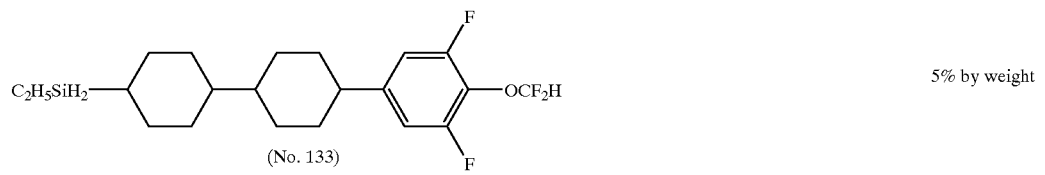
(No. 133) — 5% by weight -continued
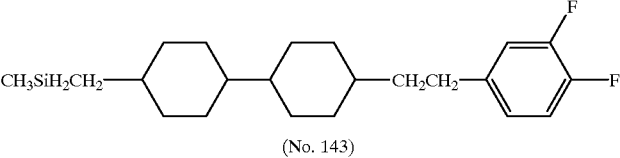 5% by weight
(No. 143)
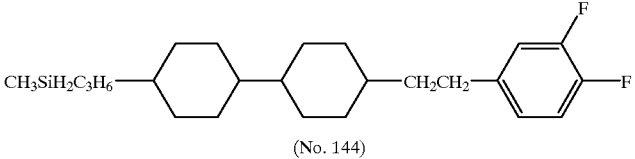 5% by weight
(No. 144)
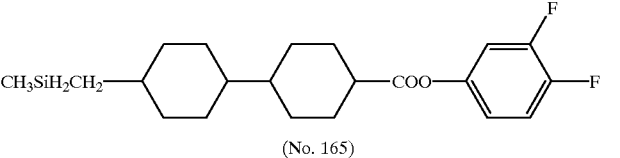 5% by weight
(No. 165)
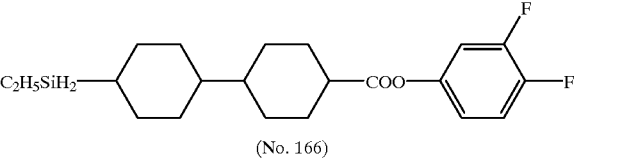 5% by weight
(No. 166)
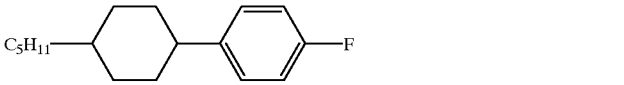 7% by weight
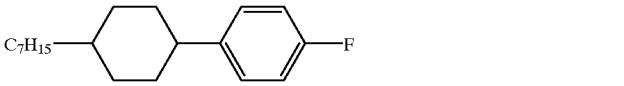 8% by weight
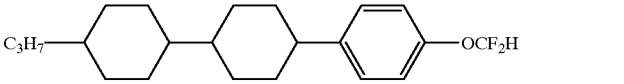 9% by weight
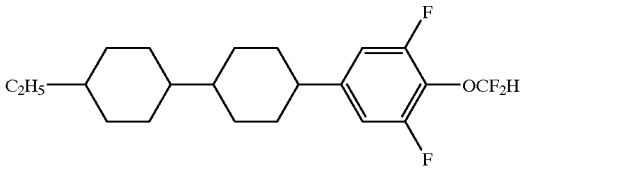 8% by weight
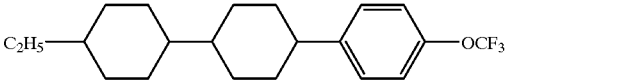 13% by weight
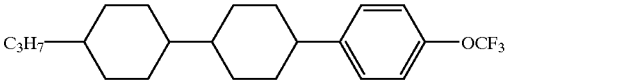 14% by weight
 6% by weight
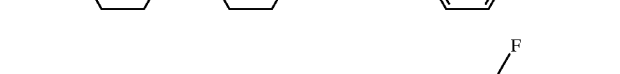 5% by weight -continued Composition Example 14

| Structure | Amount |
|---|---|
| C₂H₄=CHSiH₂—[Cy]—[Ph]—CN (No. 84) | 4% by weight |
| C₂H₅SiH₂CH₂—[Ph]—[Ph]—C₂H₅ (No. 2) | 5% by weight |
| C₂H₅SiH₂—[Cy]—CH₂CH₂—[Ph]—C₂H₅ (No. 18) | 5% by weight |
| CH₃SiH₂C₄H₈—[Cy]—[Ph]—CH₂CH₂—[Ph]—C₄H₉ (No. 48) | 5% by weight |
| C₂H₄=C₃H₅—[Cy]—[Cy]—[Ph]—CH₂SiH₂CH₃ (No. 42) | 4% by weight |
| CH₂=CH—[Cy]—[Ph]—CN | 8% by weight |
| C₂H₄=CH—[Cy]—[Ph]—CN | 3% by weight |
| C₃H₇—[Ph]—[Ph]—CN | 5% by weight |
| C₃H₇—[Ph]—[Ph]—CN | 5% by weight |
| C₃H₇—[Ph]—COO—[Ph]—CN | 5% by weight |
| C₂H₅—[Cy]—[Ph(F)]—CN | 5% by weight |
| C₄H₉—[Ph]—[Pyrimidine]—[Ph]—CN | 4% by weight |
| C₄H₉—[Ph]—[Pyrimidine]—[Ph]—C₅H₁₁ | 4% by weight |
| C₃H₇—[Cy]—CH₂CH₂—[Ph]—OC₂H₅ | 8% by weight |

10% by weight
10% by weight
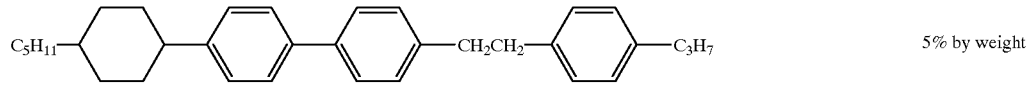
5% by weight
5% by weight
Composition Example 15
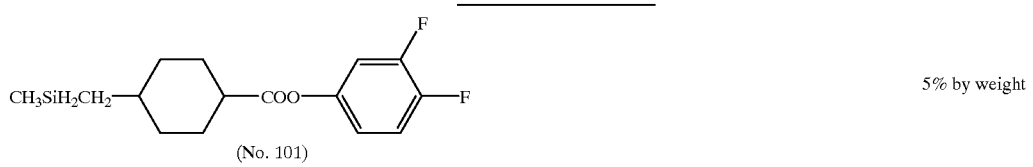
(No. 101)
5% by weight
(No. 98)
5% by weight
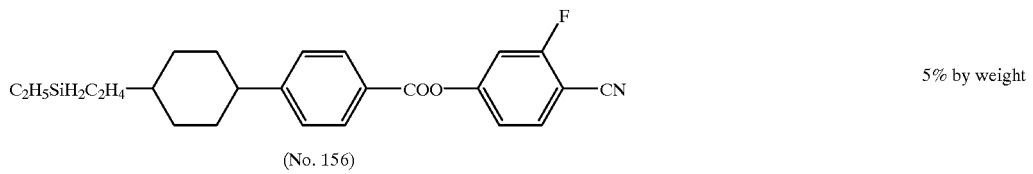
(No. 156)
5% by weight
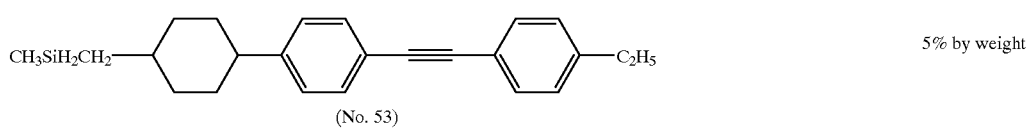
(No. 53)
5% by weight
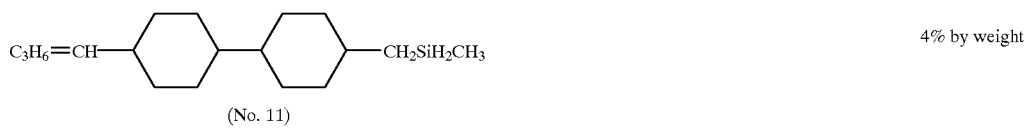
(No. 11)
4% by weight
(No. 10)
4% by weight
5% by weight
10% by weight -continued

| Structure | Weight % |
|---|---|
| C₃H₇—⌬—COO—⌬(F)—CN | 5% by weight |
| C₄H₉—⌬—COO—⌬(F)—CN | 8% by weight |
| C₅H₁₁—⬡—COO—⌬(F)—CN | 8% by weight |
| CH₃OC₃H₆—⬡—⌬(F)—CN | 6% by weight |
| C₃H₇—⬡—⬡—COO—⌬(F,F) | 5% by weight |
| C₅H₁₁—⬡—⬡—COO—⌬(F,F) | 5% by weight |
| C₂H₅—⬡—⌬—COO—⌬(F)—CN | 5% by weight |
| C₃H₇—⬡—⌬—COO—⌬(F)—CN | 5% by weight |
| C₄H₉—⬡—⌬—COO—⌬(F)—CN | 5% by weight |
| C₃H₇—⬡—⌬—C≡C—⌬—C₂H₅ | 5% by weight |

While further composition examples are shown below, the compounds in the composition examples are indicated by using the symbols defined in Table 1 below in which groups or structures shown in the column of left side terminal group, bonding group, ring structure, or right side terminal group correspond to the symbols shown on the same line in the same column of the Table, respectively.

TABLE 1

$$R-(A_1)-Z_1-\ldots-Z_n-(A_n)-X$$

| 1) Left side terminal group —R | Symbol | 3) Bonding group —Z₁—, —Zₙ— | Symbol |
|---|---|---|---|
| $C_nH_{2n+1}$— | n— | —$C_2H_4$— | 2 |

TABLE 1-continued $$R—(A_1)—Z_1—\ldots—Z_n—(A_n)—X$$

| 1) Left side terminal group —R | Symbol | 3) Bonding group —Z$_1$—, —Z$_n$— | Symbol |
|---|---|---|---|
| C$_n$H$_{2n+1}$O— | nO— | —C$_4$H$_8$— | 4 |
| C$_n$H$_{2n+1}$OC$_m$H$_{2m}$— | nOm— | —COO— | E |
| CH$_2$=CH— | V— | —C≡C— | T |
| CH$_2$=CHC$_n$H$_{2n}$— | Vn— | —CH=CH— | V |
| C$_n$H$_{2n+1}$CH=CHC$_m$H$_{2m}$— | nVm— | —CF$_2$O— | CF2O |
| C$_n$H$_{2n+1}$CH=CHC$_m$H$_{2m}$CH=CHC$_k$H$_{2k}$— | nVmVk— | —OCF$_2$— | OCF2 |

| 3) Ring structure —(A$_1$), —(A$_n$)— | Symbol | 4) Right side terminal group —X | Symbol |
|---|---|---|---|
|  | B | —F<br>—Cl | —F<br>—CL |
| 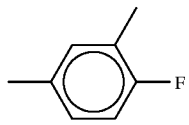 | B(F) | —CN<br>—CF$_3$ | —C<br>—CF3 |
| 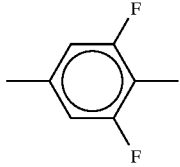 | B(F,F) | —OCF$_3$<br>—OCF$_2$H | —OCF3<br>—OCF2H |
|  | H | —C$_n$H$_{2n+1}$<br>—OC$_n$H$_{2n+1}$ | -n<br>—On |
| 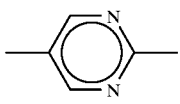 | Py | —COOCH$_3$<br>—C$_n$H$_{2n}$CH=CH$_2$ | -EMe<br>-nV |
| 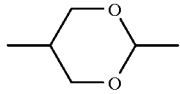 | D | —C$_m$H$_{2m}$CH=CHC$_n$H$_{2n+1}$<br>—SiH$_2$C$_n$H$_{2n+1}$ | -mVn<br>—Sin |
| 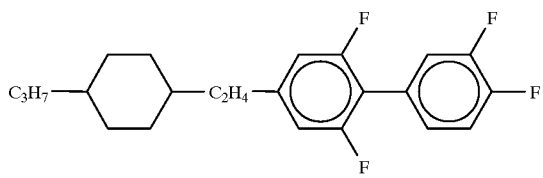 | Ch | | |

5) Examples of indication

Example 1

3-H2B(F,F)B(F)—F

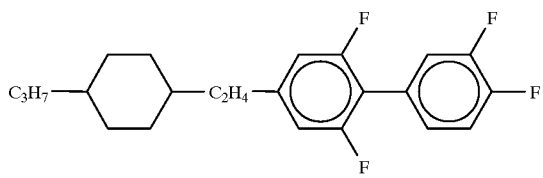

TABLE 1-continued $$R-(A_1)-Z_1-\ldots-Z_n-(A_n)-X$$

| 1) Left side terminal group —R | Symbol | 3) Bonding group $-Z_1-, -Z_n-$ | Symbol |
|---|---|---|---|

Example 2

3-HB(F)TB-2

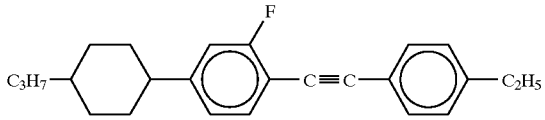

Example 3

1V2-BEB(F,F)—C

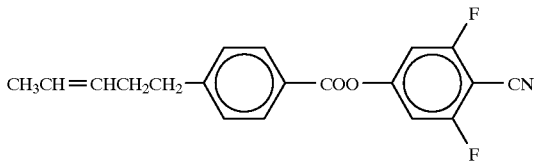

Composition Example 16

| | | |
|---|---|---|
| 3-HHB-Si2 | (No. 34) | 5.0% by weight |
| 1V2-BEB(F,F)-C | | 5.0% by weight |
| 3-HB-C | | 25.0% by weight |
| 1-BTB-3 | | 5.0% by weight |
| 2-BTB-1 | | 10.0% by weight |
| 3-HH-4 | | 11.0% by weight |
| 3-HHB-1 | | 11.0% by weight |
| 3-HHB-3 | | 4.0% by weight |
| 3-H2BTB-2 | | 4.0% by weight |
| 3-H3BTB-3 | | 4.0% by weight |
| 3-H2BTB-4 | | 4.0% by weight |
| 3-HB(F)TB-2 | | 6.0% by weight |
| 3-HB(F)TB-3 | | 6.0% by weight |

Composition Example 17

| | | |
|---|---|---|
| 4O-BB-Si3 | (No. 1) | 6.0% by weight |
| V2-HB-C | | 12.0% by weight |
| 1V2-HB-C | | 12.0% by weight |
| 3-HB-C | | 24.0% by weight |
| 3-HB(F)-C | | 5.0% by weight |
| 2-BTB-1 | | 2.0% by weight |
| 3-HH-4 | | 8.0% by weight |
| 2-HHB-C | | 3.0% by weight |
| 3-HHB-C | | 6.0% by weight |
| 3-HB(F)TB-2 | | 8.0% by weight |
| 3-H2BTB-2 | | 5.0% by weight |
| 3-H2BTB-3 | | 5.0% by weight |
| 3-H3BTB-4 | | 4.0% by weight |

Composition Example 18

| | | |
|---|---|---|
| 3-HHB-Si2 | (No. 34) | 6.0% by weight |
| 2O1-BEB(F)-C | | 5.0% by weight |
| 3O1-BEB(F)-C | | 15.0% by weight |
| 4O1-BEB(F)-C | | 13.0% by weight |
| 5O1-BEB(F)-C | | 13.0% by weight |
| 2-HHB(F)-C | | 15.0% by weight |
| 3-HHB(F)-C | | 15.0% by weight |
| 3-HB(F)TB-2 | | 4.0% by weight |
| 3-HB(F)TB-3 | | 4.0% by weight |
| 3-HB(F)TB-4 | | 4.0% by weight |
| 3-HHB-1 | | 4.0% by weight |
| 3-HHB-O1 | | 2.0% by weight |

Composition Example 19

| | | |
|---|---|---|
| 3-HHB-Si2 | (No. 34) | 4.0% by weight |
| 5-PyB-F | | 4.0% by weight |
| 3-PyB(F)-F | | 4.0% by weight |
| 2-BB-C | | 5.0% by weight |
| 4-BB-C | | 4.0% by weight |
| 5-BB-C | | 5.0% by weight |
| 2-PyB-2 | | 2.0% by weight |
| 3-PyB-2 | | 2.0% by weight |
| 4-PyB-2 | | 2.0% by weight |
| 6-PyB-O5 | | 3.0% by weight |
| 6-PyB-O6 | | 3.0% by weight |
| 6-PyB-O7 | | 3.0% by weight |
| 6-PyB-O8 | | 3.0% by weight |
| 3-PyBB-F | | 6.0% by weight |
| 4-PyBB-F | | 6.0% by weight |
| 5-PyBB-F | | 6.0% by weight |
| 3-HHB-1 | | 6.0% by weight |
| 3-HHB-3 | | 4.0% by weight |
| 2-H2BTB-2 | | 4.0% by weight |
| 2-H2BTB-3 | | 4.0% by weight |
| 2-H2BTB-4 | | 5.0% by weight |
| 3-H2BTB-2 | | 5.0% by weight |
| 3-H2BTB-3 | | 5.0% by weight |
| 3-H2BTB-4 | | 5.0% by weight |

Composition Example 20

| | | |
|---|---|---|
| 3-HHB-Si2 | (No. 34) | 7.0% by weight |
| 3-DB-C | | 10.0% by weight |
| 4-DB-C | | 10.0% by weight |
| 2-BEB-C | | 12.0% by weight |
| 3-BEB-C | | 4.0% by weight |
| 3-PyB(F)-F | | 6.0% by weight |
| 3-HEB-O4 | | 4.0% by weight |
| 4-HEB-O2 | | 6.0% by weight |
| 5-HEB-O1 | | 6.0% by weight |
| 3-HEB-O2 | | 5.0% by weight |
| 5-HEB-O2 | | 4.0% by weight |
| 5-HEB-5 | | 5.0% by weight |
| 4-HEB-5 | | 5.0% by weight |
| 1O-BEB-2 | | 4.0% by weight |
| 3-HHB-1 | | 3.0% by weight |
| 3-HHEBB-C | | 3.0% by weight |
| 3-HBEBB-C | | 3.0% by weight |

Composition Example 21

| | | |
|---|---|---|
| 5-HBEBB-C | | 3.0% by weight |
| 4O-BB-Si3 | (No. 1) | 2.0% by weight |
| 3-HHB-Si2 | (No. 34) | 5.0% by weight |
| 3-HB-C | | 18.0% by weight |
| 7-HB-C | | 3.0% by weight |
| 1O1-HB-C | | 10.0% by weight |
| 3-HB(F)-C | | 10.0% by weight |
| 2-PyB-2 | | 2.0% by weight |
| 3-PyB-2 | | 2.0% by weight |
| 4-PyB-2 | | 2.0% by weight |
| 1O1-HH-3 | | 7.0% by weight |
| 2-BTB-O1 | | 7.0% by weight |
| 3-HHB-1 | | 4.0% by weight |
| 3-HHB-F | | 4.0% by weight |
| 3-HHB-O1 | | 4.0% by weight |
| 3-HHB-3 | | 4.0% by weight |
| 3-H3BTB-2 | | 3.0% by weight |
| 3-H2BTB-3 | | 3.0% by weight |
| 2-PyBH-3 | | 4.0% by weight |
| 3-PyBH-3 | | 3.0% by weight |
| 3-PyBB-2 | | 3.0% by weight |

Composition Example 22

| | | |
|---|---|---|
| 4O-BB-Si3 | (No. 1) | 5.0% by weight |
| 3-HHB-Si2 | (No. 34) | 5.0% by weight |
| 2O1-BEB(F)-C | | 5.0% by weight |
| 3O1-BEB(F)-C | | 12.0% by weight |
| 5O1-BEB(F)-C | | 4.0% by weight |
| 1V2-BEB(F,F)-C | | 10.0% by weight |
| 3-HH-EMe | | 10.0% by weight |
| 3-HB-O2 | | 13.0% by weight |
| 3-HHEB-F | | 3.0% by weight |
| 5-HHEB-F | | 3.0% by weight |
| 3-HBEB-F | | 4.0% by weight |
| 2O1-HBEB(F)-C | | 2.0% by weight |
| 3-HBEB(F,F)-C | | 2.0% by weight |
| 3-HHB-F | | 4.0% by weight |
| 3-HHB-O1 | | 4.0% by weight |
| 3-HHB-3 | | 10.0% by weight |
| 3-HEBEB-F | | 2.0% by weight |
| 3-HEBEB-1 | | 2.0% by weight |

Composition Example 23

| | | |
|---|---|---|
| 4O-BB-Si3 | (No. 1) | 5.0% by weight |
| 3-HHB-Si2 | (No. 34) | 4.0% by weight |
| 2O1-BEB(F)-C | | 5.0% by weight |
| 3O1-BEB(F)-C | | 12.0% by weight |
| 5O1-BEB(F)-C | | 4.0% by weight |
| 1V2-BEB(F,F)-C | | 16.0% by weight |
| 3-HB-O2 | | 4.0% by weight |
| 3-HH-4 | | 2.0% by weight |
| 3-HHB-F | | 3.0% by weight |
| 3-HHB-1 | | 4.0% by weight |
| 3-HHB-O1 | | 4.0% by weight |
| 3-HBEB-F | | 4.0% by weight |
| 3-HHEB-F | | 7.0% by weight |
| 5-HHEB-F | | 7.0% by weight |
| 7-HEB-F | | 2.0% by weight |
| 3-H2BTB-2 | | 4.0% by weight |
| 3-H2BTB-3 | | 4.0% by weight |
| 3-H2BTB-4 | | 4.0% by weight |
| 3-HB(F)TB-2 | | 5.0% by weight |

Composition Example 24

| | | |
|---|---|---|
| 3-HHB-Si2 | (No. 34) | 3.0% by weight |
| 2-BEB-C | | 12.0% by weight |
| 3-BEB-C | | 4.0% by weight |
| 4-BEB-C | | 6.0% by weight |
| 3-HB-C | | 28.0% by weight |
| 3-HEB-O4 | | 12.0% by weight |
| 4-HEB-O2 | | 8.0% by weight |
| 5-HEB-O1 | | 8.0% by weight |
| 3-HEB-O2 | | 6.0% by weight |
| 5-HEB-O2 | | 5.0% by weight |
| 3-HHB-1 | | 4.0% by weight |
| 3-HHB-O1 | | 4.0% by weight |

Composition Example 25

| | | |
|---|---|---|
| 3-HHB-Si2 | (No. 34) | 5.0% by weight |
| 2-BEB-C | | 10.0% by weight |
| 5-BB-C | | 12.0% by weight |
| 7-BB-C | | 7.0% by weight |
| 1-BTB-3 | | 7.0% by weight |
| 2-BTB-1 | | 10.0% by weight |
| 1O-BEB-2 | | 10.0% by weight |
| 1O-BEB-5 | | 12.0% by weight |
| 2-HHB-1 | | 4.0% by weight |
| 2-HHB-F | | 4.0% by weight |
| 3-HHB-1 | | 7.0% by weight |
| 3-HHB-O1 | | 4.0% by weight |
| 3-HHB-3 | | 8.0% by weight |

Composition Example 26

| | | |
|---|---|---|
| 4O-BB-Si3 | (No. 1) | 4.0% by weight |
| 3-HHB-Si2 | (No. 34) | 6.0% by weight |
| 3-HB(F)-C | | 5.0% by weight |
| 2O1-BEB(F)-C | | 5.0% by weight |
| 3O1-BEB(F)-C | | 10.0% by weight |
| V-HB-C | | 10.0% by weight |
| 1V-HB-C | | 10.0% by weight |
| 2-BTB-O1 | | 10.0% by weight |
| 3-HB-O2 | | 4.0% by weight |
| V2-HH-3 | | 5.0% by weight |
| V-HH-4 | | 5.0% by weight |
| V-HHB-1 | | 10.0% by weight |
| 1V2-HBB-2 | | 10.0% by weight |
| 3-HHB-1 | | 6.0% by weight |

Composition Example 27

| | | |
|---|---|---|
| 3-HHB-Si2 | (No. 34) | 6.0% by weight |
| 2-HHB(F)-F | | 15.0% by weight |
| 3-HHB(F)-F | | 15.0% by weight |
| 5-HHB(F)-F | | 15.0% by weight |
| 2-HHB(F)-F | | 10.0% by weight |
| 3-H2HB(F)-F | | 5.0% by weight |
| 5-H2HB(F)-F | | 10.0% by weight |
| 2-HBB(F)-F | | 6.0% by weight |
| 3-HBB(F)-F | | 6.0% by weight |
| 5-HBB(F)-F | | 12.0% by weight |

Composition Example 28

| | | |
|---|---|---|
| 4O-BB-Si3 | (No. 1) | 4.0% by weight |
| 3-HHB-Si2 | (No. 34) | 5.0% by weight |
| 7-HB(F)-F | | 5.0% by weight |
| 5-H2B(F)-F | | 5.0% by weight |
| 3-HH-4 | | 5.0% by weight |
| 3-HB-O2 | | 5.0% by weight |
| 2-HHB(F)-F | | 10.0% by weight |
| 3-HHB(F)-F | | 10.0% by weight |
| 5-HHB(F)-F | | 10.0% by weight |
| 3-H2HB(F)-F | | 5.0% by weight |
| 2-HBB(F)-F | | 3.0% by weight |
| 3-HBB(F)-F | | 3.0% by weight |
| 5-HBB(F)-F | | 6.0% by weight |
| 2-H2BB(F)-F | | 5.0% by weight |
| 3-H2BB(F)-F | | 6.0% by weight |
| 3-HHB-1 | | 6.0% by weight |
| 3-HHB-O1 | | 5.0% by weight |
| 3-HHB-O3 | | 2.0% by weight |

Composition Example 29

| | | |
|---|---|---|
| 4O-BB-Si3 | (No. 1) | 4.0% by weight |
| 7-HB(F,F)-F | | 3.0% by weight |
| 3-HB-O2 | | 3.0% by weight |
| 2-HHB(F)-F | | 10.0% by weight |
| 3-HHB(F)-F | | 10.0% by weight |
| 5-HHB(F)-F | | 10.0% by weight |
| 2-HBB(F)-F | | 9.0% by weight |
| 3-HBB(F)-F | | 9.0% by weight |
| 5-HBB(F)-F | | 16.0% by weight |
| 2-HBB-F | | 4.0% by weight |
| 3-HBB-F | | 4.0% by weight |
| 5-HBB-F | | 3.0% by weight |
| 3-HBB(F,F)-F | | 5.0% by weight |
| 5-HBB(F,F)-F | | 10.0% by weight |

-continued

Composition Example 30

| | | |
|---|---|---|
| 3-HHB-Si2 | (No. 34) | 5.0% by weight |
| 7-HB(F,F)-F | | 4.0 by weight |
| 3-H2HB(F,F)-F | | 12.0% by weight |
| 4-H2HB(F,F)-F | | 10.0% by weight |
| 5-H2HB(F,F)-F | | 10.0% by weight |
| 3-HHB(F,F)-F | | 10.0% by weight |
| 4-HHB(F,F)-F | | 5.0% by weight |
| 3-HH2B(F,F)-F | | 10.0% by weight |
| 5-HH2B(F,F)-F | | 10.0% by weight |
| 3-HBB(F,F)-F | | 12.0% by weight |
| 5-HBB(F,F)-F | | 12.0% by weight |

Composition Example 31

| | | |
|---|---|---|
| 4O-BB-Si3 | (No. 1) | 2.0% by weight |
| 3-HHB-Si2 | (No. 34) | 2.0% by weight |
| 3-HB-CL | | 10.0% by weight |
| 5-HB-CL | | 4.0% by weight |
| 7-HB-CL | | 4.0% by weight |
| 1O1-HH-5 | | 3.0% by weight |
| 2-HBB(F)-F | | 8.0% by weight |
| 3-HBB(F)-F | | 8.0% by weight |
| 5-HBB(F)-F | | 14.0% by weight |
| 4-HHB-CL | | 8.0% by weight |
| 5-HHB-CL | | 8.0% by weight |
| 3-H2HB(F)-CL | | 4.0% by weight |
| 3-HBB(F,F)-F | | 10.0% by weight |
| 5-H2BB(F,F)-F | | 9.0% by weight |
| 3-HB(F)VB-2 | | 2.0% by weight |
| 3-HB(F)VB-3 | | 4.0% by weight |

Composition Example 32

| | | |
|---|---|---|
| 3-HHB-Si2 | (No. 34) | 4.0% by weight |
| 3-HHB(F,F)-F | | 9.0% by weight |
| 3-H2HB(F,F)-F | | 8.0% by weight |
| 4-H2HB(F,F)-F | | 8.0% by weight |
| 5-H2HB(F,F)-F | | 8.0% by weight |
| 3-HBB(F,F)-F | | 21.0% by weight |
| 5-HBB(F,F)-F | | 20.0% by weight |
| 3-H2BB(F,F)-F | | 10.0% by weight |
| 5-HHBB(F,F)-F | | 3.0% by weight |
| 5-HHEBB-F | | 2.0% by weight |
| 3-HH2BB(F,F)-F | | 3.0% by weight |
| 1O1-HBBH-4 | | 2.0% by weight |
| 1O1-HBBH-5 | | 2.0% by weight |

Composition Example 33

| | | |
|---|---|---|
| 4O-BB-Si3 | (No. 1) | 5.0% by weight |
| 5-HB-F | | 7.0% by weight |
| 6-HB-F | | 9.0% by weight |
| 7-HB-F | | 7.0% by weight |
| 2-HHB-OCF3 | | 7.0% by weight |
| 3-HHB-OCF3 | | 11.0% by weight |
| 4-HHB-OCF3 | | 7.0% by weight |
| 5-HHB-OCF3 | | 5.0% by weight |
| 3-HH2B-OCF3 | | 4.0% by weight |
| 5-HH2B-OCF3 | | 4.0% by weight |
| 3-HHB(F,F)-OCF3 | | 5.0% by weight |
| 3-HBB(F)-F | | 10.0% by weight |
| 5-HBB(F)-F | | 10.0% by weight |
| 3-HH2B(F)-F | | 3.0% by weight |
| 3-HB(F)BH-3 | | 3.0% by weight |
| 5-HBBH-3 | | 3.0% by weight |

Composition Example 34

| | | |
|---|---|---|
| 3-HHB-Si2 | (No. 34) | 4.0% by weight |
| 2-HHB(F)-F | | 2.0% by weight |
| 3-HHB(F)-F | | 2.0% by weight |
| 5-HHB(F)-F | | 2.0% by weight |
| 2-HBB(F)-F | | 6.0% by weight |
| 3-HBB(F)-F | | 6.0% by weight |
| 5-HBB(F)-F | | 10.0% by weight |
| 2-H2BB(F)-F | | 9.0% by weight |
| 3-H2BB(F)-F | | 9.0% by weight |
| 3-HBB(F,F)-F | | 25.0% by weight |
| 5-HBB(F,F)-F | | 19.0% by weight |
| 1O1-HBBH-4 | | 3.0% by weight |
| 1O1-HBBH-5 | | 3.0% by weight |

Composition Example 35

| | | |
|---|---|---|
| 3-HHB-Si2 | (No. 34) | 5.0% by weight |
| 3-H2HB(F,F)-F | | 6.0% by weight |
| 4-H2HB(F,F)-F | | 6.0% by weight |
| 5-H2HB(F,F)-F | | 6.0% by weight |
| 3-HH2B(F,F)-F | | 5.0% by weight |
| 3-HBB(F,F)-F | | 27.0% by weight |
| 5-HBB(F,F)-F | | 27.0% by weight |
| 3-HBEB(F,F)-F | | 4.0% by weight |
| 4-HBEB(F,F)-F | | 2.0% by weight |
| 5-HBEB(F,F)-F | | 2.0% by weight |
| 3-HHEB(F,F)-F | | 10.0% by weight |

BEST MODE FOR CARRYING OUT THE INVENTION

Now, the present invention will be described in more detail with reference to Examples. In each of the Examples, C represents a crystal, $S_A$ a smectic A phase, $S_B$ a smectic B phase, $S_X$ a smectic phase structure of which has not been identified, N a nematic phase, and I represents an isotropic phase, and the unit of all phase transition temperatures is °C.

EXAMPLE 1

Preparation of 4-propylsilyl-4'-butoxybiphenyl (Compound expressed by the general formula (1) wherein Ra represents $C_4H_9O$, Rb represents $C_3H_7SiH_2$, m is 1, both n and o are 0, both A and $A_1$ represent 1,4-phenylene, and $Z_1$ represents a covalent bond; Compound No. 1)

Diethyl ether in an amount of 400 ml and 10.0 g (33 mmol) of 4-bromo-4'-butoxybiphenyl were mixed. Under an atmosphere of nitrogen gas, 27 ml of a solution of n-BuLi (corresponding to 45 mmol) in hexane was added dropwise to the mixture so that the temperature of −50° C. was kept, and the mixture was stirred at the same temperature for 30 min. Then, the mixture was slowly warmed up and stirred at room temperature for 3 hours. Subsequently, the mixture thus obtained was added dropwise in a solution of 11.6 g (66 mmol) of propyltrichlorosilane in 10 ml of THF (tetrahydrofuran) so that the temperature of lower than −50° C. was kept, and then stirred at the same temperature for 30 min. Then, the solution was slowly warmed up and stirred at room temperature for 48 hours.

The solvent in the reaction mixture was distilled off under a reduced pressure, and the residue was distilled under a reduced condition of 182 to 203° C./1 mmHg to obtain 4.6 g of 4-propyldichlorosilyl-4'-butoxybiphenyl.

A solution of 3.0 g (8 mmol) of this compound in 15 ml of diethyl ether was added dropwise in a suspension of 0.6 g (16 mmol) of $LiAlH_4$ in 15 ml of diethyl ether at room temperature in 15 min and stirred at the same temperature for 10 hours. The reaction mixture was poured in 50 ml of a chilled 2N—HCl and then extracted with 100 ml of ethyl acetate. The organic layer thus obtained was washed with 6N—HCl (20 ml×3), 2N—NaOH (20 ml ×2), and water (30 ml×3) in turn, and then dried over anhydrous magnesium sulfate. The solvent was distilled off under a reduced pressure, and the residue was subjected to silica gel column chromatography (eluent: heptane) to obtain 1.0 g of a crude 4-propylsilyl-4'-butoxybiphenyl. This product was recrystallized from a mixed solvent of heptane/ethyl acetate to obtain 0.5 g (yield 7.8%) of the subject compound.

This compound exhibited a liquyid crystal phase, and its transition temperatures were as follows:

C lower than room temperature $S_X$ 77.8–78.2 $S_A$ 84.2–86.3 I

Each of the spectral data of the compound well supported its structure.

Mass analysis: 298 (M+)

$^1$H-NMR (CDCl$_3$, TMS internal standard) δ (ppm) 0.93–1.08 (m, 8H) 1.40–1.79 (m, 6H) 3.99 (t, 2H) 4.32 (t, 2H) 6.96–7.58 (m, 8H)

Following compounds (No. 2 to No. 33) are prepared by a method similar to that described in Example 1:

| No. | |
|---|---|
| 2 | 4-ethylsilylmethyl-4'-ethylbiphenyl |
| 3 | 4-ethoxy-1-(trans-4-ethylsilylcyclohexyl)benzene |
| 4 | 4-(trans-4-propylcyclohexyl)-1-methylsilylmethoxybenzene |
| 5 | 4-(trans-4-butoxymethylcyclohexyl)-1-ethylsilylmethylbenzene |
| 6 | 4-(trans-4-vinylcyclohexyl)-1-butylsilylbenzene |
| 7 | 4-(trans-4-(2-propenyloxy)cyclohexyl)-1-ethyldisilanylbenzene |
| 8 | trans,trans-4-propylsilyl-4'-propylbicyclohexane |
| 9 | trans,trans-4-methylsilylethyl-4'-propylbicyclohexane |
| 10 | trans,trans-4-propylsilyl-4'-vinylbicyclohexane |
| 11 | (E)-trans,trans-4-methylsilylmethyl-4'-(1-butenyl)bicyclohexane |
| 12 | trans,trans-4-(2-propenyl)silyl-4'-methoxymethylbicyclohexane |
| 13 | trans,trans-4-ethylsilyl-4'-(2,2-difluorovinyl)bicyclohexane |
| 14 | (E)-trans,trans-4-ethylsilyl-4'-(4-fluoro-1-butenyl)bicyclohexane |
| 15 | trans,trans-4-(2-propenyl)silyl-4'-(2-propenyl)bicyclohexane |
| 16 | 4-(2-(4-ethylphenyl)ethyl)-1-methylsilylpropylbenzene |
| 17 | 4-(2-(trans-4-octylcyclohexyl)ethyl)-1-pentylsilylpentylbenzene |
| 18 | 4-ethoxy-1-(2-(trans-4-ethylsilylcyclohexyl)ethyl)benzene |
| 19 | trans-4-(2-(trans-4-methoxybutylcyclohexyl)ethyl)-1-methylsilylethylcyclohexane |
| 20 | trans-4-(2-(trans-4-(3E-pentenyl)cyclohexyl)-1E-vinyl)-1-pentylsilylcyclohexane |
| 21 | 4-(2-(trans-4-(1E-propenyl)cyclohexyl)-1E-vinyl)-1-methoxyethylsilylcyclohexane |
| 22 | (E)-4-ethylsilyl-4'-pentyl-α,β-difluorostilbene |
| 23 | (E)-trans-4-(2-(trans-4-butylcyclohexyl)-1,2-difluorovinyl)-1-pentylcyclohexane |
| 24 | (E)-trans-4-(4-(trans-4-(6-undecenyl)cyclohexyl)butyl)-1-(2-oxapentyl)silylcyclohexane |
| 25 | (E)-trans-4-(4-(trans-4-pentadecylcyclohexyl)-3-butenyl)-1-methylsilylethylsilylcyclohexane |
| 26 | 4-ethylsilyl-4'-methyltolan |
| 27 | 4-methylsilyl-4'-methoxytolan |
| 28 | 2,3-difluoro-4-butylsilyl-4'-methyltolan |
| 29 | 4-propylsilylphenyl=4-propooxybenzoate |
| 30 | 4-ethylsilylmethoxyphenyl=trans-4-hexylcyclohexane carboxylate |
| 31 | (E)-trans-4-((trans-4-(3-butenyl)cycolohexyl)methylenoxa)-1-ethyldisilanylcyclohexane |
| 32 | (E)-trans,trans-4-propylsilyl-4'-(1,5-hexadienyl)bicyclohexane |
| 33 | 2-(4-methylsilylpropylpenyl)-5-propylpyrimidine |

EXAMPLE 2

Preparation of 4-(trans-4-(trans-4-propylcyclohexyl) cyclohexyl)-1-ethylbenzene (Compound expressed by the general formula (1) wherein Ra represents C$_3$H$_7$, Rb represents C$_2$H$_5$SiH$_2$, both m and n are 1, o is 0, both A and A$_1$ represent trans-1,4-cyclohexylene, A$_2$ represents 1,4-phenylene, and both Z$_1$ and Z$_2$ represent a covalent bond; Compound No. 34)

THF in an amount of 1200 ml and 20.0 g (55 mmol) of 4-(trans-4-(trans-4-propylcyclohexyl)cyclohexyl)-1-bromobenzene were mixed. Under an atmosphere of nitrogen gas, 41 ml of a solution of n-BuLi (corresponding to 66 mmol) in hexane was added dropwise to the mixture so that the temperature of −50° C. was kept, and the mixture was stirred at the same temperature for 2 hours. Then, the mixture was slowly warmed up and stirred at room temperature for 30 min.

Subsequently, the mixture thus obtained was added dropwise to a solution of 25.0 g (153 mmol) of ethyltrichlorosilane in 50 ml of THF under an atmosphere of nitrogen gas so that the temperature of lower than −50° C. was kept and stirred at the same temperature for 3 hours. Then, the solution was slowly warmed up and stirred at room temperature for 48 hours.

The solvent in the reaction mixture was distilled off under a reduced pressure. A solution of the residue in 300 ml of THF was added dropwise in a suspension of 3.2 g (84 mmol) of LiAlH$_4$ in 50 ml of THF at room temperature in 15 min, and the suspension was stirred at the same temperature for 5 hours. The reaction mixture was poured in 100 ml of a chilled 2N—HCl and extracted with 500 ml of ethyl acetate. The organic layer thus obtained was washed with 6N—HCl (100 ml×3), diluted NaHCO$_3$ (100 ml×2), and water (100 ml×3) in turn, and then dried over anhydrous magnesium sulfate. The solvent was distilled off under a reduced pressure, and the residue was subjected to silica gel column chromatography (eluent: heptane) to obtain 4.4 g of a crude 4-(trans-4-(trans-4-propylcyclohexyl)cyclohexyl)-1-ethylsilylbenzene. This product was recrystallized from a mixed solvent of ethanol/ethyl acetate to obtain 2.9 g (yield: 15.4%) of the subject compound.

This compounds exhibited a liquid crystal phase, and its transition temperatures were as follows:

C lower than room temperature $S_B$ 169.9–171.4 I

Each of the spectral data of the compound well supported its structure.

Mass analysis: 342 (M+)

$^1$H-NMR (CDCl$_3$, TMS internal standard) δ (ppm) 0.80–2.44 (m, 32H) 4.25 (t, 2H) 7.16–7.53 (dd, 4H)

Following compounds (No. 35 to No. 78) are prepared by a method similar to that described in Example 2:

| No. | |
|---|---|
| 35 | 4-methyl-1-(trans-4-(trans-4-ethylsilylcyclohexyl) cyclohexyl)benzene |
| 36 | 4-(trans-4-(trans-4-propylcyclohexyl)cyclohexyl)-1-methylsilylmethoxybenzene |
| 37 | 4-(3-fluoropropyl)-1-(trans-4-(trans-4-butylsilylcyclohexyl) cyclohexyl)benzene |
| 38 | 4-decylsilylethylsilyl-4'-(trans-4-methylsilylcyclohexyl)biphenyl |
| 39 | 4-ethylsilyl-4'-(trans-4-propylcyclohexyl)biphenyl |
| 40 | 4-methylsilylmethyl-4"-icosyl-1,1:4',1"-terphenyl |
| 41 | (E)-trans,trans,trans-4"-(1-butenyl)-4-propylsilyl-1,1':4',1"-tercyclohexane |
| 42 | (E)-4-(trans-4-(trans-4-(3-pentenyl)cyclohexyl)cyclohexyl)-1-methylsilylmethylbenzene |
| 43 | (E)-4-(trans-4-(trans-4-(5-fluoropentenyl)cyclohexyl) cyclohexyl)-1-ethylsilylbenzene |
| 44 | 3-(4-butylsilylphenyl)-3'-(2,2-difluorovinyl) spirobicyclobutane |
| 45 | 3-methyl-1-(trans-4-(4-ethylsilylphenyl)cyclohexyl) bicyclo[1.1.1]pentane |
| 46 | 4-(trans-4-(trans-4-vinylcyclohexyl)cyclohexyl)-1-methylsilylbenzene |
| 47 | (Z)-trans,trans,trans-4"-(2-pentenyl)-4-(3-propenyl)silyl-1,1':4',1"-tercyclohexane |
| 48 | 4-(2(4-butylphenyl)ethyl)-1-(trans-4-methylsilylbutylcyclohexyl)benzene |
| 49 | (E)-(trans-4-(2-(trans-4-methyldisilanylcyclohexyl)vinyl) cyclohexyl)-1-methoxybutylbenzene |

-continued

| No. | |
|---|---|
| 50 | 4-(trans-4-butylcyclohexyl)-1-(2-(4-methylsilylmethoxyphenyl)methylsilyl)benzene |
| 51 | 4-(trans-4-(4-(trans-4-heptasilanyl)butyl)cyclohexyl)-1-methoxyethoxymethylbenzene |
| 52 | (E)-2-fluoro-4-(trans-4-ethylsilylcyclohexyl)-4'-propylstilbene |
| 53 | 4-(trans-4-methylsilylmethylcyclohexyl)-4'-ethyltolan |
| 54 | 4-methylsilyl-2'-fluoro-4'-(trans-4-propylcyclohexyl)tolan |
| 55 | 4-methylsilyl-4'-(2-(trans-4-propylcyclohexyl)ethyl)tolan |
| 56 | 2-fluoro-4-(2-(trans-4-butylsilylcyclohexyl)ethyl)-4-propoxytolan |
| 57 | 4-methylsilylpropylphenyl=trans-4-(trans-4-propylcyclohexyl)cyclohexane carboxylate |
| 58 | 4-methylsilylethoxyphenyl=4-(trans-4-pentylcyclohexyl)benzoate |
| 59 | 4-propylsilylphenyl=2-fluoro-4-(trans-4-ethoxymethylcyclohexyl)benzoate |
| 60 | 4-butoxyphenyl=2-fluoro-4-(2-(trans-4-ethylsilylcyclohexyl)ethyl)benzoate |
| 61 | 4-ethylsilylphenyl=4-((trans-4-heptylcyclohexyl)carboxy)benzoate |
| 62 | (4-(trans-4-ethylsilylcyclohexyl)phenyl)difluoromethyl=4-methoxyphenyl=ester |
| 63 | (2-fluoro-4-(trans-4-butylcyclohexyl)phenyl)difluoromethyl=4-butylsilylphenyl=ether |
| 64 | (E)-4-(trans-4-(trans-4-(1,5-hexadienyl)cyclohexyl)cyclohexyl)-1-butylsilylbenzene |
| 65 | 2-(4-(trans-4-propylcyclohexyl)phenyl)-5-propylsilylpyrimidine |
| 66 | 2-(4'-butoxybiphenyl-4-yl)-5-ethylsilylpyrimidine |
| 67 | 2-(4-methyltrisilanylmethylphenyl)-5-methoxypyrimidine |
| 68 | 4-(trans-4-ethylsilylcyclohexyl)-4'-(trans-4-pentylcyclohexyl)biphenyl |
| 69 | 4-(trans-4-methylsilylmethylcyclohexyl)-4'-(trans-4-methoxymethylcyclohexyl)biphenyl |
| 70 | 4-(trans-4-ethylsilylcyclohexyl)-4'-(trans-4-(5-fluoropentylcyclohexyl)biphenyl |
| 71 | 2-fluoro-4-(trans-4-ethylsilylethylcyclohexyl)-4'-(trans-4-propylcyclohexyl)biphenyl |
| 72 | 4-(2-(4-(trans-4-methoxypropylcyclohexyl)phenyl)ethyl)-1-(trans-4-methylsilylcyclohexyl)benzene |
| 73 | 4-(trans-4-(trans-4-ethylsilylethylcyclohexyl)cyclohexyl)-4'-propylbiphenyl |
| 74 | 4-butylsilypentyl-4'-(2-(trans-4-(trans-4-(9-methyldodecyl)cyclohexyl)cyclohexyl)ethyl)biphenyl |
| 75 | 4-(2-(2-fluoro-4-(trans-4-(trans-4-methoxymethylcyclohexyl)cyclohexyl)phenyl)ethyl)-1-butylsilylbenzene |
| 76 | (E)-4-(trans-4-(trans-4-(1-propenyl)cyclohexyl)cyclohexyl)cyclohexyl)-1-ethylsilylbenzene |
| 77 | trans,trans,trans,trans-4-(2-propenyl)-4'''-vinyl-1,1':4',1":4",1'''-quatercyclohexane |
| 78 | (E)-4-(trans-4-methylsilylcyclohexyl)-4'-(trans-4-(5-fluoro-1-pentenylcyclohexyl)biphenyl |

EXAMPLE 3

Preparation of (trans-4-(trans-4-ethylsilylcyclohexyl) cyclohexyl)-3,4,5-trifluorobenzene (Compound expressed by the general formula (1) wherein Ra represents $C_2H_5SiH_2$, Rb represents F, both m and n are 1, o is 0, both A and $A_I$ represent trans-1,4-cyclohexylene, $A_2$ represents 3,5-difluoro-1,4-phenylene, and both $Z_1$ and $Z_2$ represent a covalent bond; Compound No. 79)

Lithium in an amount of 0.5 g (80 mmol), 30.0 g (80 mmol) of (trans-4-(4-bromocyclohexyl)cyclohexyl)-3,4,5-trifluorobenzene, 1000 ml of THF, and 100 ml of toluene were mixed. Ultrasonic wave was applied to the mixture under an atmosphere of argon gas while keeping the mixture at a temperature of lower than –30° C. for 3 hours.

Then, the mixture was cooled down to a temperature of lower than –60° C., added dropwise to a solution of 32.7 g (200 mmol) of ethyltrichlorosilane in 50 ml of THF so that the temperature of lower than –60° C. was kept, and stirred at the same temperature for 3 hours. Then, the solution was slowly warmed up and stirred at room temperature for 48 hours.

The solvent in the reaction mixture was distilled off under a reduced pressure. A solution of the residue in 350 ml of THF was added dropwise in a suspension of 9.1 g (240 mmol) of $LiAlH_4$ in 100 ml of THF at room temperature in 20 min, and the suspension was stirred at the same temperature for 3 hours. The reaction mixture was poured in 150 ml of chilled 2N—HCl and extracted with 500 ml of ethyl acetate. The organic layer thus obtained was washed with 6N—HCl (100 ml×3), diluted NaHCO3 (100 ml×2), and water (100 ml×3) in turn, and dried over anhydrous magnesium sulfate. The solvent was distilled off under a reduced pressure, and the residue was subjected to silica gel column chromatography (eluent: heptane) to obtain 4.4 g of a crude (trans-4-(trans-4-ethylsilylcyclohexyl) cyclohexyl)-3,4,5-trifluorobenzene. This product was recrystallized from a mixed solvent of ethanol/ethyl acetate to obtain 3.1 g (yield: 10.9%) of the subjective compound.

Each of the spectral data of the compound well supported its structure.

Mass analysis: 354 (M+)

Following compounds (No. 80 to No. 191) are prepared by a method similar to that described in Example 3:

| No. | |
|---|---|
| 80 | 4-cyano-4'-trisilanylbiphenyl |
| 81 | 4-cyano-4'-ethylsilylethylbiphenyl |
| 82 | 4-(trans-4-methylsilylmethylcyclohexyl)benzonitrile |
| 83 | (E)-4-(trans-4-(2-propenylsilyl)cyclohexyl)benzonitrile |
| 84 | (E)-4-(trans-4-(1-propenylsilyl)cyclohexyl)benzonitrile |
| 85 | 2-fluoro-4-(trans-4-methylsilylcyclohexyl)benzonitrile |
| 86 | (trans-4-ethylsilylcyclohexyl)-4-chlorobenzene |
| 87 | (trans-4-methylsilylpropylcyclohexyl)-4-chlorobenzene |
| 88 | (trans-4-ethylsilylbutylcyclohexyl)-4-fluorobenzene |
| 89 | (trans-4-ethylsilylethylcyclohexyl)-4-fluorobenzene |
| 90 | (trans-4-propylsilylpropylcyclohexyl)-3,4-difluorobenzene |
| 91 | (trans-4-pentylsilylmethylcyclohexyl)-3,4,5-trifluorobenzene |
| 92 | (trans-4-methoxymethylsilylcyclohexyl)-3-fluoro-4-trifluoromethoxybenzene |
| 93 | (2-(trans-4-ethylsilylethylcyclohexyl)ethyl)-3,4-difluorobenzene |
| 94 | (2-(trans-4-silylmethoxyethylcyclohexyl)ethyl)-4-trifluorobenzene |
| 95 | (E)-4-ethylsilyl-4'-fluoro-α,β-difluorostilbene |
| 96 | 4-methyltrisilanylmethyl-4'-fluorotolan |
| 97 | 4-cyanophenyl=4-methylsilylbenzoate |
| 98 | 3-fluoro-4-cyanophenyl=4-methylsilylbenzoate |
| 99 | 3,5-difluoro-4-cyanophenyl=4-(3-butenylsilyl)benzoate |
| 100 | 4-fluorophenyl=trans-4-ethylsilylmethylcyclohexane carboxylate |
| 101 | 3,4-difluorophenyl=trans-4-methylsilylmethylcyclohexane carboxylate |
| 102 | 2-(3,4-difluorophenyl)-5-propylsilylpyrimnidine 4-ethylsilylcyclohexyl)cyclohexyl)benzoate |
| 103 | 4-(5-methylsilylmethyldioxane-2-yl)benzonitrile |
| 104 | 4"-methoxyethylsilyl-4-cyanol-1,1':4',1"-terphenyl |
| 105 | 4-(trans-4-ethylsilylcyclohexyl)-4'-fluorobiphenyl |
| 106 | 4-(trans-4-methylsilylcyclohexyl)-3',4'-difluorobiphenyl |
| 107 | 4-(trans-4-ethylsilylcyclohexyl)-3',4'-difluorobiphenyl |
| 108 | 4-(trans-4-butylsilylcyclohexyl)-3',4'-difluorobiphenyl |
| 109 | 4-(trans-4-disilanylmethylcyclohexyl)-3',4'-difluorobiphenyl |
| 110 | 4-(trans-4-methylsilylmethylcyclohexyl)-3',4',5'-trifluorobiphenyl |
| 111 | 4-(trans-4-methylsilylpropylcyclohexyl)-3',4',5'-trifluorobiphenyl |
| 112 | 4-(trans-4-ethylsilylcyclohexyl)-4'-trifluoromethylbiphenyl |
| 113 | 2-fluoro-4-(trans-4-ethylsilylethylcyclohexyl)-3'-fluoro-4'-trifluoromethoxybiphenyl |
| 114 | 4-(trans-4-(trans-4-ethylsilylcyclohexyl)cyclohexyl)benzonitrile |
| 115 | 2-fluoro-4-(trans-4-(trans-4-methylsilylmethylcyclohexyl)cyclohexyl)benzonitrile |
| 116 | 4-(trans-4-(trans-4-(2-propenylsilyl)cyclohexyl)cyclohexyl)benzonitrile |

-continued

| No. | |
|---|---|
| 117 | (trans-4-(trans-4-methylsilylcyclohexyl)cyclohexyl)-4-chlorobenzene |
| 118 | (trans-4-(trans-4-propylsilylmethylcyclohexyl)cyclohexyl)-4-chlorobenzene |
| 119 | (trans-4-(trans-4-butylsilylcyclohexyl)cyclohexyl)-4-fluorobenzene |
| 120 | (trans-4-(trans-4-methylsilylethylcyclohexyl)cyclohexyl)-4-trifluoromethoxybenzene |
| 121 | (trans-4-(trans-4-ethylsilylcyclohexyl)cyclohexyl)-4-trifluoromethoxybenzene |
| 122 | (trans-4-(trans-4-methylsilylcyclohexyl)cyclohexyl)-4-difluoromethoxybenzene |
| 123 | (trans-4-(trans-4-methylsilylcyclohexyl)cyclohexyl)-3,4-difluorobenzene |
| 124 | (trans-4-(trans-4-ethylsilylcyclohexyl)cyclohexyl)-3,4-difluorobenzene |
| 125 | (trans-4-(trans-4-methylsilylmethylcyclohexyl)cyclohexyl)-3,4-difluorobenzene |
| 126 | (trans-4-(trans-4-ethylsilylethylcyclohexyl)cyclohexyl)-3,4-difluorobenzene |
| 127 | (trans-4-(trans-4-propylsilylmethylcyclohexyl)cyclohexyl)-3,4-difluorobenzene |
| 128 | (trans-4-(trans-4-ethylsilylcyclohexyl)cyclohexyl)-3,4,5-trifluorobenzene |
| 129 | (trans-4-(trans-4-butylsilylcyclohexyl)cyclohexyl)-3,4,5-trifluorobenzene |
| 130 | (trans-4-(trans-4-(2-fluoroethylsilyl)cyclohexyl)cyclohexyl)-3-fluoro-4-trifluoromethylbenzene |
| 131 | (trans-4-(trans-4-ethylsilylcyclohexyl)cyclohexyl)-2,3-difluoro-4-difluoromethoxybenzene |
| 132 | 4-(trans-4-butylsilylcyclohexyl)-1-(3,5-difluoro-4-(1,1,2,3,3,3-hexafluoro)phenyl)bicyclo[2,2,2]octane |
| 133 | (trans-4-(trans-4-ethylsilylcyclohexyl)cyclohexyl)-3,5-difluoro-4-difluoromethoxybenzene |
| 134 | (trans-4-(2-(trans-4-ethylsilylmethoxycyclohexyl)ethyl)cyclohexyl)-3,5-difluoro-4-trifluoromethylbenzene |
| 135 | (trans-4-(2-(trans-4-methylsilylpropylcyclohexyl)ethyl)cyclohexyl)-4-difluoromethylbenzene |
| 136 | (trans-4-(2-(trans-4-ethylsilylcyclohexyl)ethyl)cyclohexyl)-3,4-difluorobenzene |
| 137 | (trans-4-(2-(trans-4-butylsilylcyclohexyl)ethyl)cyclohexyl)-3,4,5-trifluorobenzene |
| 138 | 4-(2-(trans-4-hexylsilylcyclohyeyxl)ethyl)-3'-fluoro-4'-difluoromethoxybiphenyl |
| 139 | 4-(2-(trans-4-ethylsilylcyclohexyl)ethyl)-3',4',5'-trifluorobiphenyl |
| 140 | (2-(4-(trans-4-methoxyethylsilylcyclohexyl)phenyl)ethyl)-3,5-difluoro-4-trifluoromethoxybenzene |
| 141 | (2-(4-(trans-4-methylsilylcyclohexyl)phenyl)ethyl)-3-fluoro-4-chlorobenzene |
| 142 | (2-(trans-4-(trans-4-methylsilylmethylcyclohexyl)cyclohexyl)ethyl)-4-trifluoromethoxybenzene |
| 143 | (2-(trans-4-(trans-4-methylsilylmethylcyclohexyl)cyclohexyl)ethyl)-3,4-difluorobenzene |
| 144 | (2-(trans-4-(trans-4-methylsilylpropylcyclohexyl)cyclohexyl)ethyl)-3,4-difluorobenzene |
| 145 | (2-(trans-4-(trans-4-ethylsilylcyclohexyl)cyclohexyl)ethyl)-3,4,5-trifluorobenzene |
| 146 | (2-(trans-4-(trans-4-methylsilylmethylcyclohexyl)cyclohexyl)ethyl)-3,4,5-trifluorobenzene |
| 147 | (2-(trans-4-(trans-4-methylsilylpropylcyclohexyl)cyclohexyl)ethyl)-3,4,5-trifluorobenzene |
| 148 | (2-(trans-4-(trans-4-butylsilylcyclohexyl)cyclohexyl)ethyl)-3-fluoro-4-trifluoromethoxybenzene |
| 149 | 4-(2-(trans-4-(trans-4-pentylsilylcyclohexyl)cyclohexyl)ethyl)-2-fluorobenzonitrile |
| 150 | (trans-4-(2-(trans-4-methylsilylmethylcyclohexyl)vinyl)cyclohexyl)-3,4-difluorobenzene |
| 151 | 4-(trans-4-(2-(trans-4-methylsilylethylcyclohexyl)vinyl)cyclohexyl)-2,6-difluorobenzonitrile |
| 152 | (trans-4-(4-(trans-4-methylsilylpropylcyclohexyl)butyl)cyclohexyl)-4-fluoromethylbenzene |
| 153 | (Z)-(trans-4-(4-(trans-4-methylsilylmethylpropylcyclohexyl)-2-butenyl)cyclohexyl)-3-fluoro-4-difluoromethylbenzene |
| 154 | 4-(trans-4-propylsilylmethylcyclohexyl)-4'-fluorotolan |
| 155 | 3-fluoro-4-cyanophenyl = 4-(trans-4-ethylsilylcyclohexyl)benzoate |
| 156 | 3-fluoro-4-cyanophenyl = 4-(trans-4-ethylsilylethylcyclohexyl)benzoate |
| 157 | 3,5-difluoro-4-cyanophenyl = 2-fluoro-4-(trans-4-methylsilylethoxycyclohexyl)benzoate |
| 158 | (E)-3,5-difluoro-4-cyanophenyl = 2-fluoro-4-(2-(trans-4-(2-propenylsilyl)cyclohexyl)ethyl)benzoate |
| 159 | 4-fluorophenyl = 4-(trans-4-ethylsilylcyclohexyl)benzoate |
| 160 | 3,4,5-trifluorophenyl = 4-(trans-4-ethylsilylcyclohexyl)benzoate |
| 161 | 3,4,5-trifluorophenyl = 4-(trans-4-methyldisilanylmethylcyclohexyl)benzoate |
| 162 | 4-trifluoromethoxyphenyl = 2-fluoro-4-(trans-4-propyldisilanylcyclohexyl)benzoate |
| 163 | 4-fluorophenyl = trans-4-(trans-4-ethylsilylmethylcyclohexyl)cyclohexane carboxylate |
| 164 | 3-fluoro-4-cyanophenyl = trans-4-(trans-4-trisilanylcyclohexyl)cyclohexane carboxylate |
| 165 | 3,4-difluorophenyl = trans-4-(trans-4-methylsilylmethylcyclohexyl)cyclohexane carboxylate |
| 166 | 3,4-difluorophenyl = trans-4-(trans-4-ethylsilylcyclohexyl)cyclohexane carboxylate |
| 167 | 3,4-difluorophenyl = trans-4-(trans-4-methoxyethylsilylcyclohexyl)cyclohexane carboxylate |
| 168 | 3,4,5-trifluorophenyl = trans-4-(trans-4-ethylsilylcyclohexyl)cyclohexane carboxylate |
| 169 | 3,4,5-trifluorophenyl = trans-4-(trans-4-methylsilyloctadecylcyclohexyl)cyclohexane carboxylate |
| 170 | 3-fluoro-4-trifluoromethylphenyl = trans-4-(trans-4-butylsilylcyclohexyl)cyclohexane carboxylate |
| 171 | 3,5-difluoro-4-trifluoromethoxyphenyl = trans-4-(trans-4-methylsilylmethylcyclohexyl)cyclohexane carboxylate |
| 172 | 4-trifluoromethylphenyl = fluoro-4-((trans-4-ethylsilylcyclohexyl)carboxy)benzoate |
| 173 | (4-(trans-4-ethylsilylcyclohexyl)phenyl)difluoromethyl = 3-fluoro-4-chlorophenyl = ether |
| 174 | (4-(trans-4-methylsilylmethylcyclohexyl)phenyl)difluoromethyl = 3-fluoro-4-trifluoromethoxyphenyl = ether |
| 175 | (2-fluoro-4-(trans-4-methoxyethylsilylcyclohexyl)phenyl)difluoromethyl = 3,4,5-trifluorophenyl = ether |
| 176 | 4-(5-(4-butylsilylphenyl)pyrimidine-2-yl))benzonitrile |
| 177 | 2-(4'-fluorobiphenyl-4-yl)-5-ethylsilylethylpyrimidine |
| 178 | 4-(trans-4-(trans-4-ethylsilylcyclohexyl)cyclohyxl)-3',4',5'-trifluorobiphenyl |
| 179 | 4-(trans-4-(trans-4-ethyldisilanylmethylcyclohexyl)cyclohexyl)-4'-(1,1,2,3,3,3-hexafluoropropyl)biphenyl |
| 180 | 4-(trans-4-(trans-4-butylsilylmethylcyclohexyl)cyclohexyl)-3',5'-difluoro-4'-trifluoromethoxybiphenyl |
| 181 | 4-(2-(trans-4-(trans-4-methylsilylcyclohexyl)cyclohexyl)ethyl)-3'-fluoro-4'-trifluoromethylbiphenyl |
| 182 | 4-(2-(trans-4-(trans-4-methylsilylpropylcyclohexyl)cyclohexyl)ethyl)-4'-fluorobiphenyl |
| 183 | (2-(4-(trans-4-(trans-4-methoxyethylsilylcyclohexyl)cyclohexyl)phenyl)ethyl)-4-difluoromethylbenzene |
| 184 | 4-(4-(trans-4-(trans-4-ethylsilylcyclohexyl)cyclohexyl)butyl)-3'-fluoro-4'-difluoromethoxybiphenyl |
| 185 | 4'-cyanobiphenyl-4-yl = trans-4-(trans-4-methylsilylethylcyclohexyl)cyclohexane carboxylate |
| 186 | 4'-cyanobiphenyl-4-yl = 4-(trans-4-methylsilylethylsilylcyclohexyl)benzoate |
| 187 | 3',4',5'-trifluorobiphenyl-4-yl = trans-4(trans-4-butylsilylcyclohexyl)cyclohexane carboxylate |
| 188 | 4'-trifluoromethylbiphenyl-4-yl = trans-4-(trans-4-methylsilylpentylcyclohexyl)cyclohexane carboxylate |
| 189 | 3-fluor-4-fluoromethoxyphenyl = 2-fluoro-4-(trans-4-(trans-4-ethylsilylcyclohexyl)cyclohexyl)benzoate |
| 190 | 4-(trans-4-ethylsilylcyclohexyl)-1-(3,4,5-trifluorophenyl)cyclohexane |
| 191 | 4-(trans-4-(4-methylsilylphenyl)cyclohexyl)-1-pentylcyclohexene |

Examples in which the compounds of the present invention are used as component of liquid crystal compositions are demonstrated below. In each of the use examples, NI means the phase transition temperature (° C.) of a nematic phase to an isotropic phase, $\Delta\epsilon$ the value of dielectric anisotropy, $\Delta n$ the value of optical anisotropy, $\eta$ the viscos

EXAMPLE 4 (USE EXAMPLE 1)

A liquid crystal composition comprising the following cyanophenylcyclohexane type liquid crystalline compounds in the amount shown below

| | |
|---|---|
| 4-(trans-4-propylcyclohexyl)benzonitrile | 24% by weight |
| 4-(trans-4-pentylcyclohexyl)benzonitrile | 36% by weight |
| 4-(trans-4-heptylcyclohexyl)benzonitrile | 25% by weight |
| 4-(trans-4-pentylcyclohexyl)-4'-cyanobiphenyl | 15% by weight | was found to have the physical properties as follows:

NI: 72.4, $\Delta \epsilon$: 11.0, $\Delta n$: 0.137, $\eta$: 26.7, $V_{10}$ (at a cell thickness of 9 μm): 1.78

A nematic liquid crystal composition was obtained by mixing 15% by weight of 4-propylsilyl-4'-butoxybiphenyl (Compound No. 1) to 85% by weight of the liquid crystal composition described above. Physical properties of the nematic liquid crystal composition thus obtained were as follows:

NI: 57.2, $\Delta \epsilon$: 9.6, $\Delta n$: 0.131, $\eta$: 23.6, $V_{10}$ (at a cell thickness of 8.9 μm) : 1.44

While the nematic liquid crystal composition was left in a freezer kept at −20° C., the formation of crystals was not observed even when 60 days passed.

EXAMPLE 5 (USE EXAMPLE 2)

A liquid crystal composition comprising the equal amount of fluorine type liquid crystal compounds; trans-4-(trans-4-ethylcyclohexyl)cyclohexyl-3,4-difluorobenzene, trans-4-(trans-4-propylcyclohexyl)cyclohexyl-3,4-difluorobenzene, and trans-4-(trans-4-pentylcyclohexyl)cyclohexyl-3,4-difluorobenzene had the physical properties as follows:

NI: 112.5, $\Delta \epsilon$: 4.9, $\Delta n$: 0.079, $\eta$: 24.7, $V_{10}$ (at a cell thickness of 8.9 μm): 2.26

A liquid crystal composition was obtained by mixing 20% by weight of 4-(trans-4-(trans-4-propylcyclohexyl) cyclohexyl)-1-ethylsilylbenzene (Compound No. 34) to 80% by weight of the mixture of the liquid crystalline compounds. Physical properties of the liquid crystal composition thus obtained were as follows:

NI: 111.9, $\Delta \epsilon$: 4.1, $\Delta n$: 0.081, $\eta$: 25.4, $V_{10}$ (at a cell thickness of 8.8 μm): 2.60

While the liquid crystal composition was left in a freezer kept at −20° C., the formation of crystals was not observed even when 60 days passed.

EXAMPLE 6 (USE EXAMPLE 3)

Physical properties of the liquid crystal composition of Composition Example 16 were as follows:

NI: 89.0, $\Delta \epsilon$: 7.0, $\Delta n$: 0.162, $\eta$: 14.4, $V_{10}$: 2.11

EXAMPLE 7 (USE EXAMPLE 4)

Physical properties of the liquid crystal composition of Composition Example 17 were as follows:

NI: 84.2, $\Delta \kappa$: 8.7, $\Delta n$: 0.157, $\eta$: 18.4, $V_{10}$: 1.99

EXAMPLE 8 (USE EXAMPLE 5)

Physical properties of the liquid crystal composition of Composition Example 18 were as follows:

NI: 88.7, $\Delta \epsilon$: 30.8, $\Delta n$: 0.148, $\eta$: 86.6, $V_{10}$: 0.86

EXAMPLE 9 (USE EXAMPLE 6)

Physical properties of the liquid crystal composition of Composition Example 19 were as follows:

NI: 93.1, $\Delta \epsilon$: 6.4, $\Delta n$: 0.201, $\eta$: 34.8, $V_{10}$: 2.28

EXAMPLE 10 (USE EXAMPLE 7)

Physical properties of the liquid crystal composition of Composition Example 20 were as follows:

NI: 69.6, $\Delta \epsilon$: 11.4, $\Delta n$: 0.120, $\eta$: 39.3, $V_{10}$: 1.31

EXAMPLE 11 (USE EXAMPLE 8)

Physical properties of the liquid crystal composition of Composition Example 21 were as follows:

NI: 74.6, $\Delta \epsilon$: 7.9, $\Delta n$: 0.138, $\eta$: 17.9, $V_{10}$: 1.77

EXAMPLE 12 (USE EXAMPLE 9)

Physical properties of the liquid crystal composition of Composition Example 22 were as follows:

NI: 72.4, $\Delta \epsilon$: 22.6, $\Delta n$: 0.115, $\eta$: 34.2, $V_{10}$: 1.01

EXAMPLE 13 (USE EXAMPLE 10)

Physical properties of the liquid crystal composition of Composition Example 23 were as follows:

NI: 85.8, $\Delta \epsilon$: 28.1, $\Delta n$: 0.144, $\eta$: 41.3, $V_{10}$: 1.00

EXAMPLE 14 (USE EXAMPLE 11)

Physical properties of the liquid crystal composition of Composition Example 24 were as follows:

NI: 61.1, $\Delta \epsilon$: 9.9, $\Delta n$: 0.112, $\eta$: 25.7, $V_{10}$: 1.36

EXAMPLE 15 (USE EXAMPLE 12)

Physical properties of the liquid crystal composition of Composition Example 25 were as follows:

NI: 65.2, $\Delta \epsilon$: 6.4, $\Delta n$: 0.159, $\eta$: 19.9, $V_{10}$: 1.79

EXAMPLE 16 (USE EXAMPLE 13)

Physical properties of the liquid crystal composition of Composition Example 26 were as follows:

NI: 62.9, $\Delta \epsilon$: 9.3, $\Delta n$: 0.132, $\eta$: 19.1, $V_{10}$: 1.47

EXAMPLE 17 (USE EXAMPLE 14)

Physical properties of the liquid crystal composition of Composition Example 27 were as follows:

NI: 99.2, $\Delta \epsilon$: 4.9, $\Delta n$: 0.093, $\eta$: 24.8, $V_{10}$: 2.24

EXAMPLE 18 (USE EXAMPLE 15)

Physical properties of the liquid crystal composition of Composition Example 28 were as follows:

NI: 85.9, $\Delta \epsilon$: 3.0, $\Delta n$: 0.094, $\eta$: 19.2, $V_{10}$: 2.78

EXAMPLE 19 (USE EXAMPLE 16)

Physical properties of the liquid crystal composition of Composition Example 29 were as follows:

NI: 83.4, $\Delta \epsilon$: 5.7, $\Delta n$: 0.117, $\eta$: 25.5, $V_{10}$: 2.01

EXAMPLE 20 (USE EXAMPLE 17)

Physical properties of the liquid crystal composition of Composition Example 30 were as follows:

NI: 74.0, $\Delta \epsilon$: 8.3, $\Delta n$: 0.085, $\eta$: 26.9, $V_{10}$: 1.61

EXAMPLE 21 (USE EXAMPLE 18)

Physical properties of the liquid crystal composition of Composition Example 31 were as follows:

NI: 88.6, Δ ε: 4.8, Δn: 0.128, η: 20.8, $V_{10}$: 2.34

EXAMPLE 22 (USE EXAMPLE 19)

Physical properties of the liquid crystal composition of Composition Example 32 were as follows:

NI: 91.8, Δ ε: 8.9, Δn: 0.113, η: 33.0, $V_{10}$: 1.77

EXAMPLE 23 (USE EXAMPLE 20)

Physical properties of the liquid crystal composition of Composition Example 33 were as follows:

NI: 86.7, Δ ε: 4.5, Δn: 0.096, η: 15.9, $V_{10}$: 2.40

EXAMPLE 24 (USE EXAMPLE 21)

Physical properties of the liquid crystal composition of Composition Example 34 were as follows:

NI: 90.0, Δ ε: 7.2, Δn: 0.132, η: 33.2, $V_{10}$: 1.92

EXAMPLE 25 (USE EXAMPLE 22)

Physical properties of the liquid crystal composition of Composition Example 35 were as follows:

NI: 69.3, Δ ε: 10.4, Δn: 0.105, η: 33.7, $V_{10}$: 1.33

While each of the liquid crystal compositions shown in Examples 16 to 35 was left in a freezer kept at −20° C., the formation of crystals was not observed with any one of the liquid crystal compositions even when 60 days passed.

Comparative. Example 1

A liquid crystal composition was prepared in the same manner as in Example 4 with the exception that 4-(trans-4-propylcyclohexyl)-1-propyldimethylsilylbenzene (a compound having a trialkylsilyl group) was used as comparative compound in place of 4-propylsilyl-4'-butoxybiphenyl (Compound No. 1). Physical properties of this liquid crystal composition were as follows:

NI: lower than 15° C., Δ ε: 5.0, Δn: 0.095, η: 39.7, $V_{10}$ (at a cell thickness of 8.6 μm): 1.17

This liquid crystal composition was observed under a polarizing microscope to find that the composition contained a portion having a different NI (undissolved portion), and the composition was poor in miscibility.

From this fact, it can be understood that the comparative compound having a trialkylsilyl group is less advantageous both in viscosity and in miscibility compared with the compounds of the present invention having a monoalkylsilyl group.

Comparative Example 2

A liquid crystal composition was prepared in the same manner as in Example 4 with the exception that 4-pentyl-4'-butoxybiphenyl (a compound having no silanediyl group but having a similar structure) was used as comparative compound in place of 4-propylsilyl-4'-butoxybiphenyl (Compound No. 1). Physical properties of this liquid crystal composition were as follows:

NI: 66.7, Δ ε: 10.0, Δn: 0.137, η: 24.2, $V_{10}$ (at a cell thickness of 8.9 μm): 1.67

From this fact, it can be understood that the comparative compound having no silanediyl group is poor both in threshold voltage and in viscosity compared with the compounds of the present invention.

Comparative Example 3

A liquid crystal composition was prepared in the same manner as in Example 5 with the exception that (trans-4-(trans-4-propylcyclohexyl)cyclohexyl)-4-propylbenzene (a compound having no silanediyl group but having a similar structure) was used in place of 4-(trans-4-(trans-4-propylcyclohexyl)cyclohexyl)-1-ethylsilylbenzene (Compound No. 34). Physical properties of this liquid crystal composition were as follows:

NI: 125.7, Δ ε: 4.0, Δn: 0.083, η: 26.2, $V_{10}$ (at a cell thickness of 8.8 μm): 2.79

From this fact, it can be understood that the comparative compound having no silanediyl group is less advantageous both in threshold voltage and in viscosity compared with the compounds of the present invention having the group.

As discussed in the foregoing, any compound of the present invention has a low threshold voltage, is excellent in miscibility, and is improved in viscosity. Accordingly, when the compounds of the present invention are used as component of liquid crystal compositions, liquid crystal compositions having the characteristics described above can be obtained. Besides, novel liquid crystal compositions having desired physical properties can be provided by properly selecting the constituents of the molecule of the compounds, that is, rings, substituents and/or bonding groups.

INDUSTRIAL APPLICABILITY

According to the present invention, organosilicon compounds which are excellent in miscibility with other liquid crystal materials, have a low viscosity, and are improved in threshold voltage; liquid crystal compositions comprising the compounds; and liquid crystal display devices comprising the liquid crystal composition can be provided, and these can widely be employed for display devices of watches, tabletop calculators, word processors, TV sets, or the likes.

We claim:

1. A organosilicon compound expressed by the general formula (1)

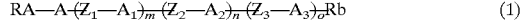

$$\text{RA—A—}(Z_1\text{—}A_1)_m\text{—}(Z_2\text{—}A_2)_n\text{—}(Z_3\text{—}A_3)_o\text{Rb} \qquad (1)$$

wherein at least one of Ra, Rb, $Z_1$, $Z_2$, and $Z_3$ has —$SiH_2$—; Ra represents hydrogen atom or an alkyl group having 1 to 20 carbon atoms; at least one —$CH_2$— in the alkyl group may be replaced by —$SiH_2$—, —O—, —S—, —CO—, —CH=CH—, —C≡C—, or 1,3-cyclobutylene, but in no case are —O— and/or —S— adjacent to each other; at least one hydrogen atom in Ra may be replaced by a halogen atom or CN; Rb represents a group selected from Ra, a halogen atom, or CN; each of A, $A_1$, $A_2$, and $A_3$, represents a divalent cyclic group and independently represents a cycloalkylene having 3 to 10 carbon atoms, cycloalkenylene having 4 to 10 carbon atoms, cycloalkadienylene having 5 to 10 carbon atoms, phenylene, bicycloalkylene having 4 to 10 carbon atoms, or a divalent spiro ring having 7 to 12 carbon atoms; at least one —$CH_2$— in these rings may be replaced by —O—, —S—, or —NH—, and at least one —CH= in these rings may be replaced by —N=, respectively; at least one hydrogen atom on the rings may be replaced by a halogen atom or CN; $Z_1$, $Z_2$ and $Z_3$ independently represent a covalent bond or —$(CH_2)_p$—; at least one —$CH_2$— in the —$(CH_2)_p$— may be replaced by —$SiH_2$—, —O—, —S—, —CO—, —CH=CH—, or —C≡C—, but in no case are —O— and/or —S— adjacent to each other; at least one hydrogen atom in $Z_1$, $Z_2$, and $Z_3$ may be replaced by a halogen atom; p is an integer of 1 to 4; m is 1, and n and o are independently 0 or 1 with the proviso that when both n and o are 0, and both A and $A_1$ are phenylene, then —$CH_2$— in $Z_1$ is not replaced by —$SiH_2$—.

2. The organosilicon compound according to claim 1 wherein and both n and o are 0.

3. The organosilicon compound according to claim 1 wherein n is 1, and o is 0.

4. The organosilicon compound according to claim 1 wherein of n, n, and o are 1.

5. The organosilicon compound according to claim 2 wherein A and $A_1$ are independently a cycloalkylene, cycloalkenylene, or 1,4-phenylene.

6. The organosilicon compound according to claim 3 wherein A, $A_1$ and $A_2$ are independently a cycloalkylene, cycloalkenylene, or 1,4-phenylene.

7. The organosilicon compound according to claim 4 wherein A, $A_1$, $A_2$, and $A_3$ are independently a cycloalkylene, cycloalkenylene, or 1,4-phenylene.

8. A liquid crystal composition comprising at least one organosilicon compound defined in any one of claims 1 to 7.

9. A liquid crystal composition comprising, as a first component, at least one organosilicon compound defined in any one of claims 1 to 7, and comprising, as a second component, at least one compound selected from the group consisting of the compounds expressed by any one of the general formulas (2), (3), and (4)

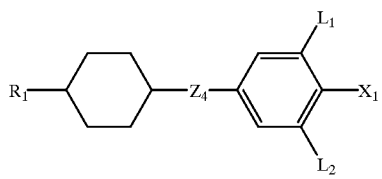
(2)

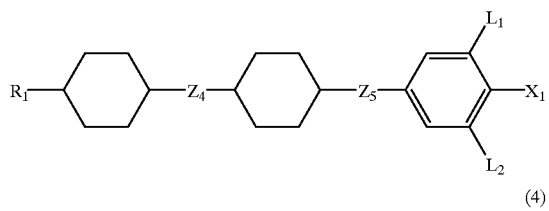
(3)

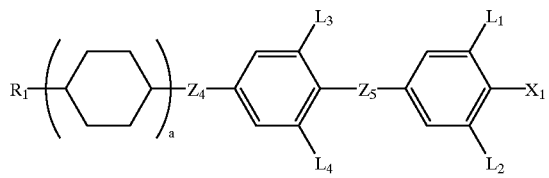
(4)

wherein $R_1$ represents an alkyl group having 1 to 10 carbon atoms; X represents F, Cl, $OCF_3$, $OCF_2H$, $CF_3$, $CF_2H$, or $CFH_2$; $L_1$, $L_2$, $L_3$ and $L_4$ independently represent H or F; $Z_4$ and $Z_5$ independently represent —$(CH_2)_2$—, —CH=CH—, or a covalent bond; and a is 1 or 2.

10. A liquid crystal composition comprising, as a first component, at least one organosilicon compound defined in any one of claims 1 to 7, and comprising, as a second component, at least one compound selected from the group consisting of the compounds expressed by any one of the general formulas (5), (6), (7), (8), and (9)

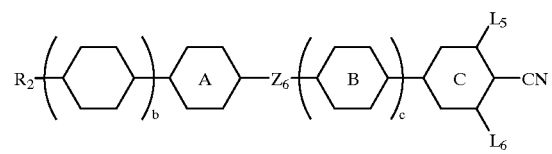
(5)

wherein $R_2$ represents F, an alkyl group having 1 to 10 carbon atoms, or an alkenyl group having 2 to 10 carbon atoms; at least one not-adjacent methylene group (—$CH_2$—) in the alkyl or alkenyl group may be replaced by oxygen atom (—O—); ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —$(CH_2)_2$—, —COO—, or a covalent bond; $L_5$ and $L_6$ independently represent H or F; and b and c are independently 0 or 1,

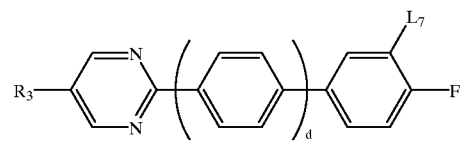
(6)

wherein $R_3$ represents an alkyl group having 1 to 10 carbon atoms; $L_7$ represents H or F; and d is 0 or 1,

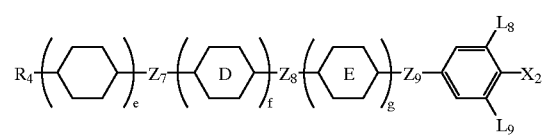
(7)

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or a covalent bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$ provided that when $X_2$ represents $OCF_3$, $OCF_2H$, $CF_3$, $CF_2H$, or $CFH_2$, then both $L_8$ and $L_9$ represent H; and e, f, and g are independently 0 or 1,

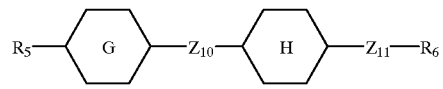
(8)

wherein $R_5$ and $R_6$ independently represent an alkyl group having 1 to 10 carbon atoms or an alkenyl group having 2 to 10 carbon atoms; at least one not-adjacent methylene group (—$CH_2$—) in the alkyl or alkenyl group may be replaced by oxygen atom (—O—); ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents —C≡C—, —COO—, —$(CH_2)_2$—, —CH=CH—C≡C—, or a covalent bond; and $Z_{11}$ represents —COO— or a covalent bond,

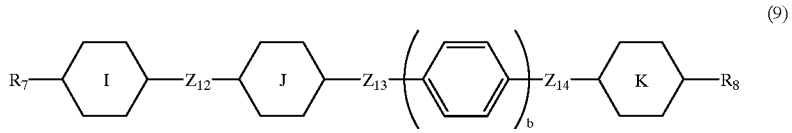

(9)

wherein $R_7$ and $R_8$ independently represent an alkyl group having 1 to 10 carbon atoms or an alkenyl group having 2 to 10 carbon atoms; at least one not-adjacent methylene group (—CH$_2$—) in the alkyl or alkenyl group may be replaced by oxygen atom (—O—); ring I represents trans-1,4-cyclohexylene group, 1,4-phenylene group, or pyrimidine-2,5-diyl group; ring J represents trans-1,4-cyclohexylene group, 1,4-phenylene group at least one hydrogen atom on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —(CH$_2$)$_2$—, or a covalent bond; $Z_{13}$ represents —CH=CH—, —C≡C—, —COO—, or a covalent bond, and h is 0 or 1.

11. A liquid crystal composition comprising, as a first component, at least one organosilicon compound defined in any one of claims 1 to 7, comprising, as a part of a second component, at least one compound selected from the group consisting of the compounds expressed by any one of the general formula (2), (3), and (4)

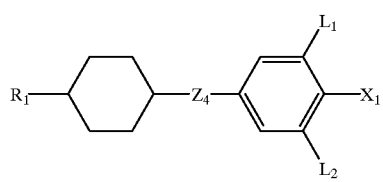

(2)

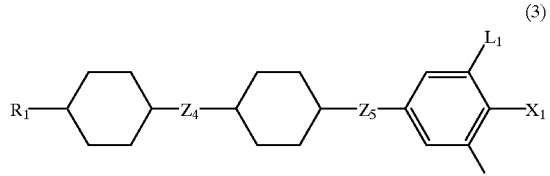

(3)

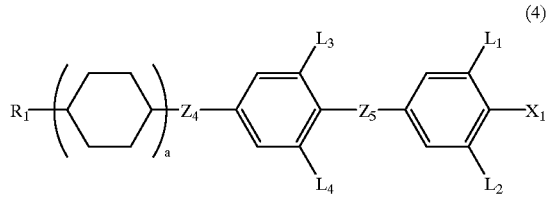

(4)

wherein $R_1$ represents an alkyl group having 1 to 10 carbon atoms; $X_1$ represents F, Cl, OCF$_3$, OCF$_2$H, CF$_3$, CF$_2$H, or CFH$_2$; $L_1$, $L_2$, $L_3$ and $L_4$ independently represent H or F; $Z_4$ and $Z_5$ independently represent —(CH$_2$)$_2$—, —CH=CH—, or a covalent bond; and a is 1 or 2, and comprising, as other part of the second component, at least one compound selected from the group consisting of the compounds expressed by any one the general formulas (5), (6), (7), (8), and (9)

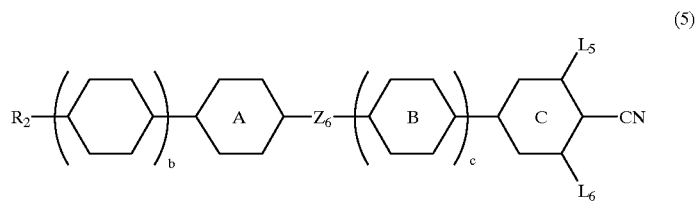

(5)

wherein $R_2$ represents F, an alkyl group having 1 to 10 carbon atoms, or an alkenyl group having 2 to 10 carbon atoms; at least one not-adjacent methylene group (—CH$_2$—) in the alkyl or alkenyl group may be replaced by oxygen atom (—O—); ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —(CH$_2$)$_2$—, —COO—, or a covalent bond; $L_5$ and $L_6$ independently represent H or F; and b and c are independently 0 or 1,

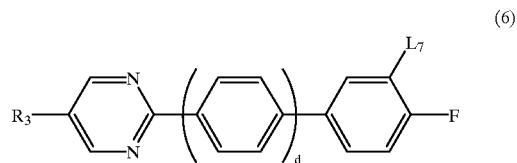

(6)

wherein $R_3$ represents an alkyl group having 1 to 10 carbon atoms; $L_7$ represents H or F; and d is 0 or 1,

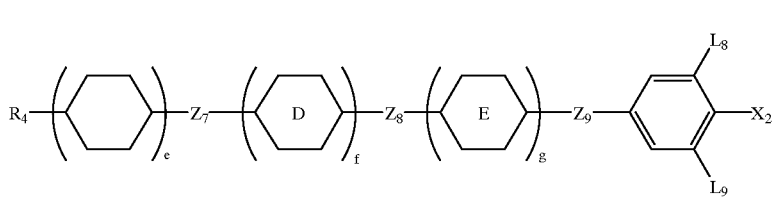

(7)

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or a covalent bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$ provided that when $X_2$ represents $OCF_3$, $OCF_2H$, $CF_3$, $CF_2H$, or $CFH_2$, then both $L_8$ and $L_9$ represent H; and e, f, and g are independently 0 or 1,

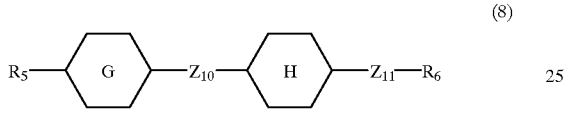

(8)

wherein $R_5$ and $R_6$ independently represent an alkyl group having 1 to 10 carbon atoms or an alkenyl group having 2 to 10 carbon atoms; at least one not-adjacent methylene group (—$CH_2$—) in the alkyl or alkenyl group may be replaced by oxygen atom (—O—); ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents —C≡C—, —COO—, —$(CH_2)_2$—, —CH=CH—C≡C—, or a covalent bond; and $Z_{11}$ represents —COO— or a covalent bond,

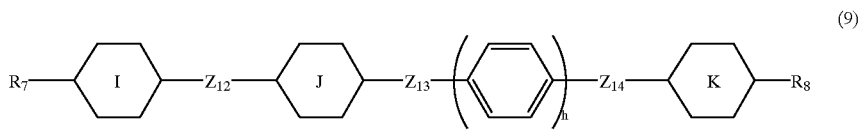

(9)

wherein $R_7$ and $R_8$ independently represent an alkyl group having 1 to 10 carbon atoms or an alkenyl group having 2 to 10 carbon atoms; at least one not-adjacent methylene group (—$CH_2$—) in the alkyl or alkenyl group may be replaced by oxygen atom (—O—); ring I represents trans-1,4-cyclohexylene group, 1,4-phenylene group, or pyrimidine-2,5-diyl group; ring J represents trans-1,4-cyclohexylene group, 1,4-phenylene group at least one hydrogen atom on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —$(CH_2)_2$—, or a covalent group; $Z_{13}$ represents —CH=CH—, —C≡C—, —COO—, or a covalent bond, and h is 0 or 1.

12. A liquid crystal display device comprising the liquid crystal composition defined in claim 8.

13. A liquid crystal display device comprising the liquid crystal composition defined in claim 9.

14. A liquid crystal display device comprising the liquid crystal composition defined in claim 10.

15. A liquid crystal display device comprising the liquid crystal composition defined in claim 11.

* * * * *